US010800826B2

(12) United States Patent
Carrington et al.

(10) Patent No.: US 10,800,826 B2
(45) Date of Patent: Oct. 13, 2020

(54) ANTIBODY PEPTIDE CONJUGATES THAT HAVE AGONIST ACTIVITY AT BOTH THE GLUCAGON AND GLUCAGON-LIKE PEPTIDE 1 RECEPTORS

(71) Applicants: Merck Sharp & Dohme Corp., Rahway, NJ (US); Ambrx, Inc., La Jolla, CA (US)

(72) Inventors: Paul Carrington, Hillsborough, NJ (US); Grigori Ermakov, Santa Clara, CA (US); Robert M. Garbaccio, Lansdale, PA (US); Wolfgang Seghezzi, Mountain View, CA (US); Elisabetta Bianchi, Pomezia (IT); Federica Orvieto, Pomezia (IT); Dennis Gately, San Diego, CA (US); Nick Knudsen, Escondido, CA (US); Anthony Manibusan, San Diego, CA (US)

(73) Assignees: Merck Sharp & Dohme Corp., Rahway, NJ (US); Ambryx, Inc., La Jolla, CA (US)

( * ) Notice: Subject to any disclaimer, the term of this patent is extended or adjusted under 35 U.S.C. 154(b) by 19 days.

(21) Appl. No.: 15/765,505

(22) PCT Filed: Oct. 4, 2016

(86) PCT No.: PCT/US2016/055265
§ 371 (c)(1),
(2) Date: Apr. 3, 2018

(87) PCT Pub. No.: WO2017/062334
PCT Pub. Date: Apr. 13, 2017

(65) Prior Publication Data
US 2019/0071483 A1    Mar. 7, 2019

Related U.S. Application Data

(60) Provisional application No. 62/237,009, filed on Oct. 5, 2015.

(51) Int. Cl.
| | |
|---|---|
| *C07K 14/605* | (2006.01) |
| *C07K 16/26* | (2006.01) |
| *C07K 16/28* | (2006.01) |
| *A61K 47/68* | (2017.01) |
| *A61P 3/10* | (2006.01) |
| *A61K 39/00* | (2006.01) |

(52) U.S. Cl.
CPC ........ *C07K 14/605* (2013.01); *A61K 47/6811* (2017.08); *A61K 47/6843* (2017.08); *A61P 3/10* (2018.01); *C07K 16/26* (2013.01); *C07K 16/2869* (2013.01); *A61K 2039/505* (2013.01); *C07K 2317/75* (2013.01); *C07K 2319/00* (2013.01)

(58) Field of Classification Search
CPC .................. C07K 14/605; A61K 47/6843
See application file for complete search history.

(56) References Cited

U.S. PATENT DOCUMENTS

| | | |
|---|---|---|
| 5,094,848 A | 3/1992 | Brixner et al. |
| 5,621,002 A | 4/1997 | Bosslet et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,677,435 B2 | 1/2004 | Barbas, III et al. |
| 6,759,509 B1 | 7/2004 | King et al. |
| 6,835,807 B1 | 12/2004 | Susaki et al. |
| 7,229,618 B2 | 6/2007 | Johnson et al. |
| 10,550,190 B2 | 2/2020 | Garbaccio |
| 2002/0042539 A1 | 4/2002 | Arstad et al. |
| 2002/0102590 A1 | 8/2002 | Taing et al. |
| 2003/0096743 A1 | 5/2003 | Senter et al. |
| 2003/0130189 A1 | 7/2003 | Senter et al. |
| 2004/0018194 A1 | 1/2004 | Francisco et al. |
| 2004/0052793 A1 | 3/2004 | Carter et al. |
| 2004/0121940 A1 | 6/2004 | De Groot et al. |
| 2004/0219203 A1 | 11/2004 | Griffiths et al. |
| 2006/0122143 A1 | 6/2006 | Boyer et al. |
| 2007/0048773 A1 | 3/2007 | Lee et al. |

(Continued)

FOREIGN PATENT DOCUMENTS

| | | |
|---|---|---|
| WO | WO199813059 A1 | 4/1998 |
| WO | WO2004032828 A2 | 4/2004 |

(Continued)

OTHER PUBLICATIONS

Chabenne, J. et al., A Glucagon Analog Chemically Stabilized for Immediate Treatment of Life-threatening hypoglycemia, Molecular Metabolism, 2014, vol. 3, No. 3, pp. 293-300.

(Continued)

*Primary Examiner* — Gyan Chandra
(74) *Attorney, Agent, or Firm* — David W. Van Goor; Anna Cocuzzo

(57) ABSTRACT

Described are antibody peptide conjugates (APCs) comprising an antibody conjugated to a peptide analog of glucagon, which have been modified to be resistant to cleavage and inactivation by dipeptidyl peptidase IV (DPP-IV) and to increase in vivo half-life of the peptide analog while enabling the peptide analog to have agonist activity at the glucagon (GCG) receptor and the glucagon-like peptide 1 (GLP-1) receptor and the use of such APCs for treatment of metabolic disorders such as diabetes, non-alcoholic fatty liver disease (NAFLD), non-alcoholic steatohepatitis (NASH), and obesity.

10 Claims, 5 Drawing Sheets
Specification includes a Sequence Listing.

(56) References Cited

U.S. PATENT DOCUMENTS

| | | |
|---|---|---|
| 2010/0249072 A1 | 9/2010 | Borch et al. |
| 2012/0058473 A1 | 3/2012 | Yue et al. |
| 2015/0065393 A1 | 3/2015 | Jacobson |
| 2017/0182181 A1 | 6/2017 | Garbaccio |
| 2019/0030171 A1 | 1/2019 | Garbaccio |

FOREIGN PATENT DOCUMENTS

| | | |
|---|---|---|
| WO | 2009058734 A1 | 5/2009 |
| WO | WO2010096142 | 8/2010 |
| WO | WO2014153164 | 8/2010 |
| WO | WO2011116387 A1 | 9/2011 |
| WO | 2014073845 A1 | 5/2014 |
| WO | WO2015006736 | 1/2015 |
| WO | 2015153401 A1 | 10/2015 |
| WO | WO2017062271 A3 | 6/2017 |

OTHER PUBLICATIONS

Alley et al., Contribution of Linker Stability to the Activity of Anticancer Immunoconjugates, Bioconjugate Chem., 2008, pp. 759-765, 19.

Austin et al., Oxidizing Potential of Endosomes and Lysosomes Limits Intracellular Cleavage of Disulfide Based Antibody Drug Conjugates, Proc. Natl. Acad. Sci., USA, 2005, pp. 17987-17992, 102.

Blattler et al., New Heterobifunctional Protein Cross-linking Reagent that forms an Acid Labile Link, Biochem., 1985, pp. 1517-1524, 24.

Carl et al., A Novel Connector Linkage Applicable in Prodrug Design, J. Med. Chem., 1981, pp. 479-480, 24.

Chakravarty et al., Plasmin-activated Prodrugs for Cancer Chemotherapy, J. Med. Chem., 1983, pp. 638-644, 26.

Chari et al., Targeted Delivery of Chemotherapeutics: Tumor-activated Prodrug Therapy, Adv. Drug Delivery Rev., 1998, pp. 89-104, 31.

Co-pending application U.S. Appl. No. 15/765,515, filed Apr. 3, 2018, Philip E. Brandish et al.

De Groot et al., Design, Synthesis, and Biological Evaluation of a Dual Tumor Specific Motive, Molecular Cancer Therapeutics, 2002, pp. 901-911, 1.

De Groot et al., Elongated Multiple Electronic Cascade and Cyclization Spacer Systems in Activatible Anticancer Prodrugs for Enhanced Drug Release, Journal of Organic Chemistry, 2001, pp. 8815-8830, 66.

De Groot et al., Synthesis and Biological Evaluation of Novel Prodrugs of Anthracyclines for Selective Activation by the Tumor-Associated Protease Plasmin, J. Med. Chem., 1999, pp. 5277-5283, 42.

Doronina et al., Enhanced Activity of Monomethylauristatin F through Monoclonal Antibody Delivery, Bioconj. Chem., 2006, pp. 114-124, 17.

Erickson et al., Antibody-Maytansinoid Conjugates are Activated in Targeted Cancer Cells by Lysomomal Degradation, Cancer Research, 2006, pp. 4426-4433, 66.

Graversen, JH, Targeting the Hemoglobin Scavenger receptor CD163 in Macrophages Highly Increases the Anti-Inflammatory Potency of Dexamethasone, The Journal of the American Society of Gene Therapy, 2012, 1550-1558, vol. 20, No. 8.

Hallam, Trevor J. et al., Antibody Conjugates with Unnatural Amino Acids, Molecular Pharmaceutics, 2015, 1848-1862, 12.

Hamann et al., An Anti-MUC1 Antibody Calicheamicin Conjugate for Treatment of Solid Tumors, Bioconj. Chem., 2005, pp. 346-353, 16.

Hashimoto et al., Significance of Cathepsin B Accumulation in Synovial luid of Rheumatoid Arthritis, Biochem Biophys. Res. Commun., 2001, pp. 334-339, 288.

Hong et al., Nucleoside Conjugates as Potential Antitumor Agents, Journal of Medicinal Chemistry, 1979, No. 11, pp. 1428-1432, 22.

Kern, Jeffrey C., Discovery of Pyrophosphate Diesters as Tunable, Soluble, and Bioorthogonal Linkers for Site-Specific Antibody-Drug Conjugates, Journal of the American Chemical Society, 2015, 1430-1445, Vol. 138.

King et al., Monoclonal Antibody Conjugates of Doxorubicin Prepared with Branched Peptide Linkers, J. Med. Chem., 2002, pp. 4336-4343, 45.

Lewis et al., Targeting HER2-Positive Brease Cancer with Trastuzumab-DM1, An Antibody-Cytotoxic Drug conjugate, Cancer Research, 2008, pp. 9280-9290, 68.

NA, Pub Chem Compound Summary, CID21125146, 2007, pp. 1 and 2, NA.

Ostrovskis et al., Application of Metal Free Click Chemistry in Biological Studies, Current Organic Chemistry, 2013, pp. 610-640, 17.

Sinha et al., Plasma Membrane Association of Cathepsin B in Human Prostate Cancer, Prostate, 2001, pp. 172-184, 49.

Widdison et al., Semisynthetic Maytansine Analogues for the Targeted Treatment of Cancer, J. Med. Chem., 2006 pp. 4392-4408, 49.

ANTIBODY PEPTIDE CONJUGATES THAT HAVE AGONIST ACTIVITY AT BOTH THE GLUCAGON AND GLUCAGON-LIKE PEPTIDE 1 RECEPTORS

CROSS REFERENCE TO RELATED APPLICATIONS

This application is a National Stage Application of PCT/US2016/055265 filed Oct. 4, 2016, and claims benefit under 35 U.S.C. 119(e) of U.S. Provisional Application No. 62/237,009, filed Oct. 5, 2015, both of which are incorporated herein in their entities.

BACKGROUND OF THE INVENTION

(1) Field of the Invention

The present invention relates to antibody peptide conjugates (APCs) comprising an antibody conjugated to a peptide analog of glucagon, which have been modified to be resistant to cleavage and inactivation by dipeptidyl peptidase IV (DPP-IV) and to increase in vivo half-life of the peptide analog while enabling the peptide analog to have agonist activity at the glucagon (GCG) receptor and the glucagon-like peptide 1 (GLP-1) receptor and the use of such APCs for treatment of metabolic disorders such as diabetes, non-alcoholic fatty liver disease (NAFLD), non-alcoholic steatohepatitis (NASH), and obesity.

(2) Description of Related Art

Pre-proglucagon is a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of pre-proglucagon, while GLP-1 is produced as a 37-amino acid peptide that corresponds to amino acids 72 through 108 of pre-proglucagon. GLP-1 (7-36) amide or GLP-1 (7-37) acid are biologically potent forms of GLP-1, that demonstrate essentially equivalent activity at the GLP-1 receptor.

During hypoglycemia, when blood glucose levels drop below normal, glucagon signals the liver to break down glycogen and release glucose, causing blood glucose levels to rise toward a normal level. Hypoglycemia is a common side effect of insulin therapy in patients with hyperglycemia (elevated blood glucose levels) due to diabetes. Thus, glucagon's most recognized role in glucose regulation is to counteract the action of insulin and maintain blood glucose levels.

GLP-1 has different biological activities compared to glucagon. Its actions include stimulation of insulin synthesis and secretion, inhibition of glucagon secretion, and inhibition of food intake. GLP-1 has been shown to reduce hyperglycemia in diabetics. Exendin-4, a peptide from lizard venom that shares about 50% amino acid identity with GLP-1, activates the GLP-1 receptor and likewise has been shown to reduce hyperglycemia in diabetics. There is also evidence that GLP-1 and exendin-4 may reduce food intake and promote weight loss, an effect that would be beneficial not only for diabetics but also for patients suffering from obesity. Patients with obesity have a higher risk of diabetes, hypertension, hyperlipidemia, cardiovascular disease, and musculoskeletal diseases.

Glucagon is a peptide hormone structurally related to GLP-1 that is well recognized for its acute ability to increase blood glucose through stimulation of glycogenolysis and gluconeogenesis (Jiang & Zhang, Am. J. Physio.1 Endocrinol. Metab. 284: E671-E678 (2003)). Of lesser appreciation are the chronic effects of glucagon pharmacology characterized by increases in thermogenesis, satiety, lipolysis, fatty acid oxidation, and ketogenesis (Habegger et al., Nat. Rev. Endocrinol. 6: 689-697 (2010)). Repeated administration of glucagon was first reported decades ago to yield improvements in rodent metabolism, accompanied with lower body weight (Salter, Am. J. Clin. Nutr. 8: 535-539 (1960)). Nonetheless, the inherent risk of hyperglycemia, especially in insulin resistant states such T2DM, has complicated the translation of these observations to human study.

The hormone oxyntomodulin (OXM, glucagon-37) is a posttranslational product of preproglucagon processing in the intestine and central nervous system (CNS) and is secreted from L-cells in the gut in response to food intake. Discovered in 1983, OXM has been implicated in the regulation of food intake and energy expenditure (Jarrouse et al., Endocrinol. 115: 102-105 (1984); Schjoldager et al., Eur. J. Clin. Invest., 18: 499-503 (1988)). Central or peripheral administration of OXM in rats causes a decrease in short term food intake with minimal effects on gastric emptying (Dakin et al. Endocrinology, 142: 4244-4250 (2001), Dakin et al. Endocrinology, 145: 2687-2695 (2004)). Repeated intracerebroventricular administration of OXM in rats results in elevated core temperatures and reduced weight gain compared to pair-fed animals, suggesting effects on both caloric intake and energy expenditure (Dakin et al. Am. J. Physiol. Endocrinol. Metab., 283: E1173-E1177 (2002)).

In related studies, peripheral administration of OXM dose-dependently inhibited both fast-induced and dark phase food intake, but unlike GLP-1, had no effect on gastric emptying. OXM also reduced levels of fasting ghrelin and increased c-fos immunoreactivity, in the arcuate nucleus (ARC). Repeated seven-day IP administration of OXM caused a reduction in the rate of body weight gain and adiposity in rats (See Dakin et al. Endocrinology, 145: 2687-2695 (2004)).

Studies of OXM action in mice have demonstrated that although OXM can activate both the glucagon (GCG) and the GLP-1 receptors, the anorectic actions of OXM require only the GLP-1 receptor, as icy OXM inhibits food intake in glucagon receptor knockout mice. However, the anorectic effects of OXM are completely absent in GLP-1 receptor knockout mice. Furthermore, exendin-4, but not OXM, regulates energy expenditure in mice. Hence, OXM appears to be a weak agonist at the GLP-1 receptor, when used in pharmacological concentrations (See Baggio et al., Gastroenterol. 127: 546-58 (2004)). OXM was also found to ameliorate glucose intolerance in mice fed a high fat diet (Dakin et al., Am. J. Physiol. Endocrinol. Metab. 294: E142-E147 (2008) and increase the intrinsic heart rate in mice independent of the GLP-1 receptor (Sowden et al., Am. J. Physiol. Regul. Integr. Comp. Physiol. 292: R962-R970 (2007). OXM has also been shown to differentially affect GLP-1 receptor beta-arrestin recruitment and signaling through Galpha (Jorgensen et al., J. Pharma. Exp. Therapeut. 322: 148-154 (2007)) and to differentially affect hypothalamic neuronal activation following peripheral injection of OXM (Choudhri et al., Biochem. Biophys. Res. Commun. 350: 298-306 (2006)).

In humans, a single 90 minute intravenous infusion of OXM in normal weight healthy subjects reduced hunger scores and food intake at a buffet meal by about 19%. Cumulative twelve-hour caloric intake was reduced by about 11% with no reports of nausea or changes in food palatability (Cohen et al., J. Clin. Endocrinol. Metab., 88: 4696-4701 (2003); Lykkegaard et al., ADA Scientific Sessions, Abstract #1506-P (2003)). More recently, pre-prandial injections of OXM over a four-week period in obese healthy volunteers (BMI about 33) led to a significant reduction of caloric intake on the first day of treatment (about 25%) that was maintained over the course of the study (35% reduction after four weeks) (Wynne et al., Diabetes 54: 2390-2395 (2005)). Robust weight loss was observed at the end of the study in treated subjects (1.9%, placebo-corrected). Plasma levels of OXM were similar to that observed in the infusion study (peak concentration about 950 pM). The absence of any tachyphylaxis and a low incidence of mild and transient nausea (about 3%) despite the relatively high doses necessitated by the poor in vivo stability of OXM (plasma t½<12 minutes) renders this hormone one of the few obesity targets with both human validation and an attractive tolerability profile.

OXM has a very short half-life and is rapidly inactivated by the cell surface dipeptidyl peptidase IV (DPP-IV) (Zhu et al., J. Biol. Chem. 278: 22418-22423 (2002). However, DPP-IV inhibitors are weight-neutral in the clinic, suggesting that supraphysiological levels of OXM (900-1000 pM) may be required to achieve weight loss in humans. OXM peptide analogs for inducing weight loss in humans have been the object of Published International Application Nos. WO03/022304, WO2004/062685, WO2006/134340, and WO2010/096052.

Recently, two independent and simultaneous papers reported the use of relatively balanced GLP-1 receptor/GCG receptor co-agonists as being of enhanced efficacy and safety relative to pure GLP1R agonists in the treatment of rodent obesity, with simultaneous improvement in glycemic control (Day et al., Nat. Chem. Biol. 5: 749-757 (2009); Pocai eta al., Diabetes 58: 2258-2266 (2009)). Of related significance is work with oxyntomodulin (OXM), an endogenous precursor to glucagon, which is secreted postprandially by L-cells of the jejuno-ileum together with GLP-1 (Hoist, Regul. Pept. 93: 45-51 (2000); Drucker, Nat. Clin. Pract. Endocrinol. Metab. 1: 22-31 (2005).

Glucagon peptide analogs and derivatives modified to have various degrees of activity at the GLP-1 receptor and GCG receptor have been disclosed in Published International Application Nos. WO2008/1010017, WO2009/155258, WO2011/075393, WO2012/177444, and WO2012/177443. Some of the disclosed glucagon peptide analogs were reported therein to have activity at both the GLP-1 receptor and GCG receptor; however, there remains a need for co-agonist peptides that have activity or potency at the GLP-1 receptor and GCG receptor.

BRIEF SUMMARY OF THE INVENTION

The invention provides antibody peptide conjugates (APCs) that are agonists of the glucagon (GCG) receptor and the glucagon-like peptide 1 (GLP-1) receptors. Native glucagon normally has about 1% of the activity of native GLP-1 at the GLP-1 receptor. However, the GCG receptor/GLP-1 receptor co-agonist peptides of the invention have activity or potency at the GCG receptor and GLP-1 receptor. In particular aspects, the peptides have an $EC_{50}$ of about 0.007 to about 10.0 nM at the GCG receptor and an $EC_{50}$ of about 0.002 to about 10.0 nM at the GLP-1 receptor. The peptides herein are useful for the treatment of metabolic disorders, such as but not limited to, diabetes (e.g., type 1 diabetes, Type 2 diabetes, or gestational diabetes), non-alcoholic fatty liver disease (NAFLD), non-alcoholic steatohepatitis (NASH), and/or obesity.

The present invention provides an antibody peptide conjugate comprising an antibody having a light chain having the amino acid sequence of SEQ ID NO:64 and a heavy chain having the amino acid sequence of SEQ ID NO:65 conjugated to a peptide having the amino acid sequence

```
                                            (SEQ ID NO: 62)
His-Xaa²-Gln-Gly-Thr-Phe-Thr-Ser-Asp-Tyr-Ser-Lys-

Tyr-Leu-Asp-Xaa¹⁶-Arg-Ala-Ala-Gln-Asp-Phe-Val-Gln-

Trp-Leu-Met-Asp-Thr-Lys-Gln
``` wherein $Xaa^2$ is α-aminoisobutyric acid (aib) or D-Ser; $Xaa^{16}$ is aib; at least one of the amino acids at position 10, 24, or 31 is substituted with a Lys or the amino acids at positions 10 and 24 are each substituted with a Lys; and optionally the peptide comprises up to three additional amino acid substitutions; wherein the heavy chain includes a substitution of the amino acid a position 16, 32, 33, 56, 114, 125, 142, 179, 198, or 211 with a para-acetylphenylalanine (pAcF) or the light chain includes a substitution of the amino acid a position 125 or 142 with a pAcF; wherein the peptide comprises either (i) an aminoxy acid residue covalently linked to the epsilon amino a group of the Lys at position 10, 24, or 31 or (ii) an aminoxy acid residue covalently linked to the epsilon amino a group of the Lys at position 10, 24, or 31 via a polyethylene glycol (PEG) spacer, a γGlu spacer, or a γGlu-γGlu spacer; wherein the pAcF residue is covalently linked to the aminooxy acid residue; and wherein the antibody peptide conjugate is an agonist of the glucagon receptor and the glucagon-like peptide 1 receptor. In particular aspects of the antibody peptide conjugate, the peptide comprises a fatty acid acid covalently linked to the epsilon amino group of the Lys at position 10 via a γGlu-γGlu spacer. In particular aspects of the antibody peptide conjugate, the fatty acid comprises a C14, C15, C16, C17, C18, C19, or C20 fatty acid. In particular aspects of the antibody peptide conjugate, the fatty acid comprises a C14 fatty acid.

In particular aspects of the antibody peptide conjugate, the polyethylene glycol spacer comprises 2, 4, 6, 8, 24, or 36 ethoxy units.

The present invention further provides an antibody peptide conjugate comprising an antibody having a light chain having the amino acid sequence of SEQ ID NO:64 and a heavy chain having the amino acid sequence of SEQ ID NO:65 conjugated to a peptide having the amino acid sequence

```
                                            (SEQ ID NO: 63)
His-Xaa²-Gln-Gly-Thr-Phe-Thr-Ser-Asp-Xaa¹⁰-Ser-

Xaa¹²-Tyr-Leu-Asp-Xaa¹⁶-Arg-Ala-Ala-Xaa²⁰-Asp-Phe-

Val-Xaa²⁴-Xaa²⁵-Xaa²⁶-Xaa²⁷-Xaa²⁸-Xaa²⁹-Lys-Xaa³¹
```

Wherein $Xaa^2$ is α-aminoisobutyric acid (aib) or D-Ser; $Xaa^{16}$ is aib; $Xaa^{31}$ is Lys or Gln when $Xaa^{10}$ or $Xaa^{24}$ is Lys with the proviso that for any peptide only one of $Xaa^{10}$, $Xaa^{24}$, or $Xaa^{31}$ can be Lys; $Xaa^{10}$ is Tyr when $Xaa^{31}$ is Lys, or Lys if neither $Xaa^{24}$ or $Xaa^{31}$ is Lys, or Tyr or Lys if $Xaa^{24}$ is Lys; $X^{12}$ is Lys or aib when $Xaa^{31}$ is Lys, with the proviso that when $Xaa^{12}$ is aib, then either $Xaa^{20}$ or $Xaa^{24}$ is aib and $Xaa^{10}$, $Xaa^{25}$, $Xaa^{26}$, $Xaa^{25}$, $Xaa^{27}$, $Xaa^{28}$, and $Xaa^{29}$ are Tyr, Trp, Leu, Met, Asp, and Thr, respectively; $Xaa^{20}$ is Gln or aib when $Xaa^{24}$ or $Xaa^{31}$ is Lys with the proviso that when $Xaa^{20}$ is aib then $Xaa^{10}$, $Xaa^{24}$, $Xaa^{25}$, $Xaa^{26}$, $Xaa^{25}$, $Xaa^{27}$, $Xaa^{28}$, and $Xaa^{29}$ are Tyr, Gln, Trp, Leu, Met, Asp, and Thr, respectively; $Xaa^{24}$ is Gln when $Xaa^{10}$ is Lys, or Gln or aib when $Xaa^{31}$ is Lys, or Lys when $Xaa^{10}$ and $Xaa^{31}$ are Tyr and Gln, respectively, or Glu when $Xaa^{28}$ is Lys, with the proviso that when $Xaa^{24}$ is aib then $Xaa^{10}$, $Xaa^{25}$, $Xaa^{26}$, $Xaa^{27}$, $Xaa^{28}$, an $Xaa^{29}$ are Tyr, Trp, Leu, Met, Asp, and Thr, respectively; $Xaa^{25}$ is Trp, Gln, Asp, Lys, aib, alpha-methylphenylanine, (αMePhe), alpha-methyl-leucine (αMeLeu), alpha-methyltryptophan (αMeTrp), beta-homo tryptophan (ßhoTrp), 5-hydroxy tryptophane (W(5OH)), ß-3-benzothienyl)-alanine (Bzt), 7-azatryptophan (AzTrp), 2-naphthyl-alanine (2Nap), (3-Pyridyl)alanine (3Pyr), 3-(2-quinoyl)-alanine (3Qui), 4,4'-biphenylalanine (BIP), or N-methyl-tryptophane (Trp(Me)) with the proviso that when $Xaa^{25}$ is Gln, Asp, Lys, aib, αMePhe, αMeLeu, αMeTrp, ßhoTrp, W(5OH), Bzt, AzTrp, 2Nap, 3Pyr, 3-(2-quinoyl)-alanine (3Qui), 4,4'-biphenylalanine (BIP), or N-methyl-tryptophane (Trp(Me)), then $Xaa^{12}$, $Xaa^{20}$, $Xaa^{24}$, $Xaa^{26}$, and $Xaa^{27}$ are Lys, Gln, Gln, Leu, and Met, respectively, and $Xaa^{31}$ is Lys; $Xaa^{26}$ is Leu, aib, or hexafluoroleucine (HFL) with the proviso that when $Xaa^{26}$ is aib or HFL, then $Xaa^{31}$ is Lys and $Xaa^{12}$, $Xaa^{20}$, $Xaa^{24}$, $Xaa^{25}$, and $Xaa^{27}$ are Lys, Gln, Gln, Trp, and Met, respectively; $Xaa^{27}$ is Met, methionine sulfoxide (M(O)), homoleucine (hLeu), or homocyclo-exylalanine (hCha) with the proviso that when $Xaa^{27}$ is M(O), hLeu, or hCha, then $Xaa^{31}$ is Lys and $Xaa^{12}$, $Xaa^{20}$, $Xaa^{24}$, $Xaa^{25}$, $Xaa^{26}$, $Xaa^{28}$, $Xaa^{29}$ are Lys, Gln, Gln, Trp, Leu, Asp, and Thr, respectively; $Xaa^{28}$ is Asp or aib, or Lys when $Xaa^{24}$ is Glu, with the proviso that when $Xaa^{28}$ includes aib then $Xaa^{24}$ is Lys and $Xaa^{10}$, $Xaa^{12}$, $Xaa^{25}$, $Xaa^{26}$, $Xaa^{27}$, $Xaa^{29}$ are Tyr, Lys, Trp, Leu, Met, and Thr, respectively; $Xaa^{29}$ is Thr or aib with the proviso that when $Xaa^{29}$ is aib then $Xaa^{31}$ is Lys and $Xaa^{10}$, $Xaa^{12}$, $Xaa^{25}$, $Xaa^{26}$, $Xaa^{27}$, $Xaa^{28}$ are Tyr, Lys, Trp, Leu, Met, Asp, and Thr, respectively; one of $Lys^{10}$, $Lys^{24}$, or $Lys^{31}$ is covalently linked at its epsilon amino group to an aminooxy acid residue; optionally, $Lys^{10}$ may be covalently linked at its epsilon amino group to a fatty acid if $Lys^{24}$ is covalently linked to aminooxy acid residue; wherein either the light chain includes a substitution of the amino acid at position 125 or 142 with a para-acetylphenylalanine (pAcF) or the heavy chain includes a substitution of the amino acid a position 16, 32, 33, 56, 114, 179, 198, or 211 with a AcF; and wherein the aminooxy acid residue of the peptide is covalently linked to the pAcF residue of the antibody.

In particular aspects of the antibody peptide conjugate, the peptide comprises the $Lys^{10}$, $Lys^{24}$, or $Lys^{31}$ covalently linked at the epsilon amino group directly to the aminooxy acid residue or to the aminooxy acid residue via a polyethylene glycol spacer, γGlu spacer, or γGlu-γGlu spacer.

In particular aspects of the antibody peptide conjugate, the polyethylene glycol spacer comprises 2, 4, 6, 8, 24, or 35 ethoxy units. In particular aspects of the antibody peptide conjugate, the peptide comprises the $Lys^{10}$ covalently linked to a fatty acid acid via a γGlu-γGlu spacer. In particular aspects of the antibody peptide conjugate, the fatty acid comprises a C14, C15, C16, C17, C18, C19, or C20 fatty acid. In particular aspects of the antibody peptide conjugate, the fatty acid comprises a C14 fatty acid.

In particular aspects of the antibody peptide conjugate, the peptide comprises $Lys^{31}$ covalently linked at the epsilon amino group directly to the aminooxy acid residue or to the aminooxy acid residue via a polyethylene glycol spacer, γGlu spacer, or γGlu-γGlu spacer.

In particular aspects of the antibody peptide conjugate, the peptide comprises a Glu at $Xaa^{24}$ and a Lys at $Xaa^{28}$ and a lactam bridge between the Glu and the Lys.

The present invention further provides an antibody peptide conjugate comprising:

an antibody having a light chain having the amino acid sequence of SEQ ID NO:64, SEQ ID NO:71, or SEQ ID NO:72 and a heavy chain having the amino acid sequence of selected from SEQ ID NO:65, SEQ ID NO:66, SEQ ID NO:67, SEQ ID NO:68, SEQ ID NO:69, SEQ ID NO:70, SEQ ID NO:73, SEQ ID NO:74, or SEQ ID NO:75 conjugated to a peptide comprising the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:43, SEQ ID NO:44, SEQ ID NO:45, SEQ ID NO:46, SEQ ID NO:47, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, or SEQ ID NO:61, with the proviso that if the light chain has the amino acid sequence of SEQ ID NO:64 then heavy chain does not have the amino acid sequence of SEQ ID NO:65 and if the light chain has the amino acid sequence of SEQ ID NO:71 or 72 then the heavy chain has the amino acid sequence of SEQ ID NO:65.

The present invention further provides an antibody peptide conjugate comprising an antibody having a light chain having the amino acid sequence of SEQ ID NO:64 and a heavy chain having the amino acid sequence of SEQ ID NO:66 conjugated to a peptide have the amino acid sequence of SEQ ID NO:6, SEQ ID NO:13, SEQ ID NO:58, or SEQ ID NO:60.

The present invention further provides a pharmaceutical composition comprising the antibody peptide conjugate of any one of the previous claims and a pharmaceutically acceptable carrier.

The present invention further provides a kit comprising the pharmaceutical composition and a device for administering the pharmaceutical composition to a patient, optionally, wherein the device comprises a syringe comprising the pharmaceutical composition.

The present invention further provides a method for treating a metabolic disease or disorder in a patient, comprising administering to a patient in need the pharmaceutical composition to treat the metabolic disease or disorder.

The present invention further provides the pharmaceutical composition for use in the treatment of a metabolic disease or disorder.

The present invention further provides the use of the pharmaceutical composition for the manufacture of a medicament to treat the metabolic disease or disorder.

In particular aspects, the metabolic disease or disorder comprises diabetes, non-alcoholic fatty liver disease (NAFLD), non-alcoholic steatohepatitis (NASH), or obesity. In particular aspects the diabetes comprises Type 1, diabetes, Type II diabetes, or gestational diabetes.

The present invention further provides an antibody comprising a light chain having the amino acid sequence of SEQ ID NO:64, SEQ ID NO:71, or SEQ ID NO:72 and a heavy chain having the amino acid sequence of selected from SEQ ID NO:65, SEQ ID NO:66, SEQ ID NO:67, SEQ ID NO:68, SEQ ID NO:69, SEQ ID NO:70, SEQ ID NO:73, SEQ ID NO:74, or SEQ ID NO:75 with the proviso that if the light chain has the amino acid sequence of SEQ ID NO:64 then heavy chain does not have the amino acid sequence of SEQ ID NO:65 and if the light chain has the amino acid sequence of SEQ ID NO:71 or 72 then the heavy chain has the amino acid sequence of SEQ ID NO:65.

The present invention further provides an antibody comprising antibody comprising a light chain having the amino acid sequence of SEQ ID NO:64 and a heavy chain having the amino acid sequence of SEQ ID NO:65; wherein the heavy chain includes a substitution of the amino acid a position 16, 32, 33, 56, 114, 179, 198, or 211 with a para-acetylphenylalanine (pAcF).

The present invention further provides for the use of the antibody for the manufacture of a medicament for the treatment of a metabolic disease or disorder.

In particular aspects, the metabolic disease or disorder comprises diabetes, non-alcoholic fatty liver disease (NAFLD), non-alcoholic steatohepatitis (NASH), or obesity. In particular aspects the diabetes comprises Type 1, diabetes, Type II diabetes, or gestational diabetes.

Definitions

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

As used herein an "effective" amount or a "therapeutically effective amount" of a glucagon peptide refers to a nontoxic but sufficient amount of the peptide to provide the desired effect. For example one desired effect would be the prevention or treatment of hyperglycemia, e.g., as measured by a change in blood glucose level closer to normal, or inducing weight loss/preventing weight gain, e.g., as measured by reduction in body weight, or preventing or reducing an increase in body weight, or normalizing body fat distribution. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route, e.g., subcutaneous, intramuscular, intraspinal, or intravenous.

As used herein, the term "peptide" encompasses a chain of 3 or more amino acids and typically less than 100 amino acids, wherein the amino acids are naturally occurring or coded or non-naturally occurring or non-coded amino acids. Non-naturally occurring amino acids refer to amino acids that do not naturally occur in vivo but which, nevertheless, can be incorporated into the peptide structures described herein. "Non-coded" as used herein refers to an amino acid that is not an L-isomer of any of the following 20 amino acids: Ala, Cys, Asp, Glu, Phe, Gly, His, He, Lys, Leu, Met, Asn, Pro, Gin, Arg, Ser, Thr, Val, Trp, Tyr. "Coded" as used herein refers to an amino acid that is an L-isomer of any of the following 20 amino acids: Ala, Cys, Asp, Glu, Phe, Gly, His, He, Lys, Leu, Met, Asn, Pro, Gin, Arg, Ser, Thr, Val, Trp, Tyr. In some embodiments, the peptides and variant peptides described herein are about the same length as SEQ ID NO: 1 (which is 29 amino acids in length), e.g. 25-35 amino acids in length. Exemplary lengths include 29, 30, 31, 32, 33, 34, 35, 36, 37, 38, 39, 40, 41, 42, 43, 44, 45, 46, 47, 48, 49, or 50 amino acids in length.

Typically, polypeptides and proteins have a polymer length that is greater than that of "peptides."

Amino acid "modification" refers to an insertion, deletion or substitution of one amino acid with another. In some embodiments, the amino acid substitution or replacement is a conservative amino acid substitution, e.g., a conservative substitution of the amino acid at one or more of positions 2, 5, 7, 10, 11, 12, 13, 14, 16, 17, 18, 19, 20, 21, 24, 27, 28 or 29. As used herein, the term "conservative amino acid substitution" is the replacement of one amino acid with another amino acid having similar properties, e.g., size, charge, hydrophobicity, hydrophilicity, and/or aromaticity, and includes exchanges within one of the following five groups:
I. Small aliphatic, nonpolar or slightly polar residues:
Ala, Ser, Thr, Pro, Gly;
II. Polar, negative-charged residues and their amides and esters:
Asp, Asn, Glu, Gin, cysteic acid and homocysteic acid;
III. Polar, positive-charged residues:
His, Arg, Lys; Ornithine (Orn)
IV. Large, aliphatic, nonpolar residues:
Met, Leu, He, Val, Cys, Norleucine (Nle), homocysteine
V. Large, aromatic residues:
Phe, Tyr, Trp, acetyl phenylalanine In some embodiments, the amino acid substitution is not a conservative amino acid substitution, e.g., is a non-conservative amino acid substitution.

As used herein the term "charged amino acid" or "charged residue" refers to an amino acid that comprises a side chain that is negative-charged (i.e., de-protonated) or positive-charged (i.e., protonated) in aqueous solution at physiological pH. For example negative-charged amino acids include aspartic acid, glutamic acid, cysteic acid, homocysteic acid, and homoglutamic acid, whereas positive-charged amino acids include arginine, lysine and histidine. Charged amino acids include the charged amino acids among the 20 coded amino acids, as well as atypical or non-naturally occurring or non-coded amino acids.

As used herein the term "acidic amino acid" refers to an amino acid that comprises a second acidic moiety (other than the carboxylic acid of the amino acid), including for example, a carboxylic acid or sulfonic acid group.

As used herein, the term "acylated amino acid" refers to an amino acid comprising an acyl group which is non-native to a naturally-occurring amino acid, regardless of the means by which it is produced (e.g. acylation prior to incorporating the amino acid into a peptide, or acylation after incorporation into a peptide).

As used herein the term "alkylated amino acid" refers to an amino acid comprising an alkyl group which is non-native to a naturally-occurring amino acid, regardless of the means by which it is produced. Accordingly, the acylated amino acids and alkylated amino acids of the present disclosures are non-coded amino acids.

As used herein, the term "selectivity" of a molecule for a first receptor relative to a second receptor refers to the following ratio: $EC_{50}$ of the molecule at the second receptor divided by the $EC_{50}$ of the molecule at the first receptor. For example, a molecule that has an EC50 of 1 nM at a first receptor and an $EC_{50}$ of 100 nM at a second receptor has 100-fold selectivity for the first receptor relative to the second receptor.

As used herein, "glucagon potency" or "potency compared to native glucagon" of a molecule refers to the inverse ratio of the $EC_{50}$ of the molecule at the glucagon receptor divided by the $EC_{50}$ of native glucagon at glucagon receptor.

As used herein, "GLP-1 potency" or "potency compared to native GLP-1" of a molecule refers to the inverse ratio of the $EC_{50}$ of the molecule at GLP-1 receptor divided by the $EC_{50}$ of native GLP-1 at GLP-1 receptor.

As used herein, the terms "antibody," "immunoglobulin," "immunoglobulins" and "immunoglobulin molecule" are used interchangeably. Each immunoglobulin molecule has a unique structure that allows it to bind its specific antigen, but all immunoglobulins have the same overall structure as described herein. The basic immunoglobulin structural unit is known to comprise a tetramer of subunits. Each tetramer has two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Light chains are classified as either kappa or lambda. Heavy chains are classified as gamma, mu, alpha, delta, or epsilon, and define the antibody's isotype as IgG, IgM, IgA, IgD, and IgE, respectively.

The light and heavy chains are subdivided into variable regions and constant regions (See generally, Fundamental Immunology (Paul, W., ed., 2nd ed. Raven Press, N.Y., 1989), Ch. 7. The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. The terms include naturally occurring forms, as well as fragments and derivatives. Included within the scope of the term are classes of immunoglobulins (Igs), namely, IgG, IgA, IgE, IgM, and IgD. Also included within the scope of the terms are the subtypes of IgGs, namely, IgG1, IgG2, IgG3, and IgG4. The term is used in the broadest sense and includes single monoclonal antibodies (including agonist and antagonist antibodies) as well as antibody compositions which will bind to multiple epitopes or antigens.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. The term "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) Nature, 256:495, or may be made by recombinant DNA methods (See, for example, U.S. Pat. No. 4,816,567; the disclosure of which is incorporated herein by reference).

DETAILED DESCRIPTION OF THE INVENTION

The present disclosures provide antibody peptide conjugates (APCs) in which an antibody is conjugated to peptides that exhibit activity at the GLP-1 receptor (GLP-1) and the glucagon (GCG) receptor. In this regard, the present disclosures provide APCs conjugated to GLP-1 receptor/GCG receptor co-agonist peptides. In exemplary embodiments, the presently disclosed APCs exhibit activity or potency at the GCG receptor and/or the GLP-1 receptors.

In exemplary embodiments, the APCs described herein exhibit other improvements in properties relative to native glucagon or native GLP-1, such as greater stability, greater solubility, a prolonged half-life in circulation, a delayed onset of action, an extended duration of action, a dampened peak (e.g., relatively decreased mean peak plasma concentration), and an improved resistance to proteases, such as DPP-IV.

Glucagon is a peptide hormone structurally related to GLP-1 that is well recognized for its acute ability to increase blood glucose through stimulation of glycogenolysis and gluconeogenesis. While administration of glucagon was first reported over 60 years ago to yield improvements in rodent metabolism, including lowering body weight (Salter, Am. J. Clin. Nutr. 8: 535-539 (1960)) these results have not been translated into the use of glucagon in therapies for a treatment of obesity in humans, particularly due to the inherent risk of hyperglycemia, especially in insulin-resistant type-2 diabetic patients.

The use of GCG receptor/GLP-1 receptor co-agonists as being of enhanced efficacy and safety relative to pure GLP-1 receptor agonists in the treatment of rodent obesity, with simultaneous improvement in glycemic control was disclosed by Day et al. in Nat. Chem. Biol. 5: 749-757 (2009) and Pocai et al. in Diabetes 58: 2258-2266 (2009). Oxyntomodulin (OXM) is an endogenous precursor to glucagon, which is secreted postprandially by L-cells of the jejuno-ileum together with GLP-1 and has been shown to be a balanced co-agonist at the GLP-1 receptor and glucagon receptor albeit of relatively low potency (Hoist, Regul. Pept. 93: 45-51 (2000); Drucker, J. Nat. Clin. Pract. Endocrinol. Metab. 1: 22-31 (2005); Baldissera et al., Regul. Pept. 21: 151-166 (1988); Gros et al., Endocrinol. 133: 631-638 (1993); Pocai et al., op. cit.). A 4-week clinical study in obese subjects demonstrated that repeated subcutaneous administration of OXM was well tolerated and caused significant weight loss, with a concomitant reduction in food intake (Wynne et al., Diabetes 54: 2390-2395 (2005)).

Figure 1:
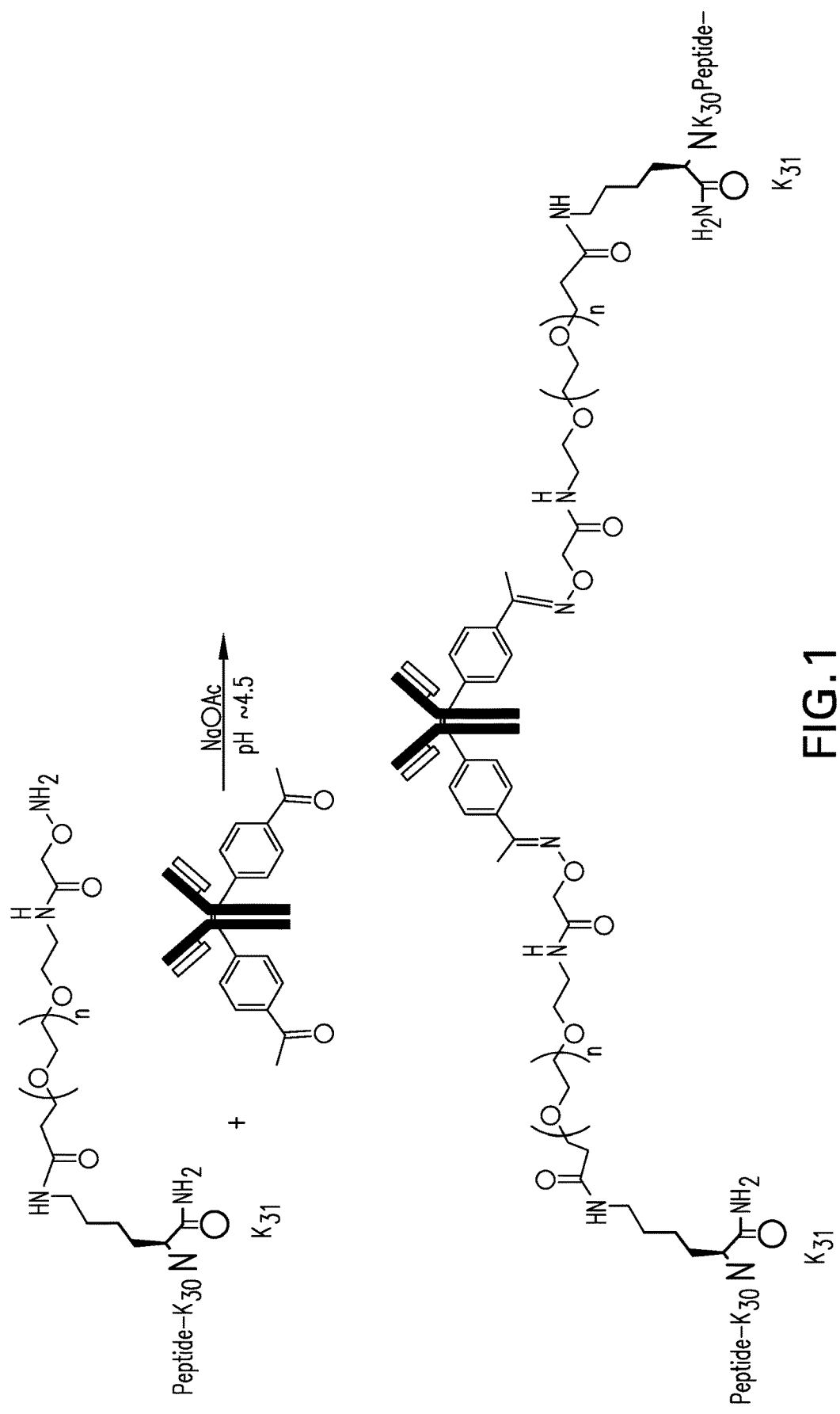
FIG. 1 illustrates the general structure of an antibody peptide conjugate and its synthesis. The antibody is shown with two para-acetylphenylalanine residues conjugated to the heavy chain of the antibody. A peptide comprising an aminooxy functional reactive group conjugated to the lysine residue at position 31 of the peptide via a polyethylene spacer is conjugated to the antibody under conditions appropriate for the $NH_2$ of the aminooxy group to react with the side acetyl group of the paracetylphenylalanine residue in the antibody amino acid sequence to produce an antibody with two peptides conjugated thereto.

Antibodies, such as IgG are "Y"-shaped macromolecules called monomers. A monomer is composed of four glycoprotein chains: two identical heavy chains and two identical light chains. The two heavy chains have a high molecular weight that varies with the class of antibody. The light chains come in two varieties: kappa or lambda and have a lower molecular weight than the heavy chains. The four glycoprotein chains are connected to one another by disulfide (S—S) bonds and non-covalent bonds (see FIG. 1). Additional S—S bonds fold the individual glycoprotein chains into a number of distinct globular domains. The area where the top of the "Y" joins the bottom is called the hinge. This area is flexible to enable the antibody to bind to pairs of epitopes various distances apart on an antigen.

The APCs of the present invention comprises the co-agonist peptide conjugated to an Ambody, which is an antibody derived from Palivizumab that comprises a pAcF residue in the heavy chains. Because each APC is comprised of two identical light chains and two identical heavy chains, each APC of the present invention comprises at least two co-agonist peptides (See FIG. 1).

Table 1 shows exemplary GCG receptor/GLP-1 receptor co-agonist peptides which may be conjugated to the pAcF of an Ambody as disclosed herein to provide an APC as disclosed herein.

TABLE 1

| SEQ ID NO: | # | Peptide Structure |
|---|---|---|
| 1 | 4704 | HXQGTFTSDYSKYLDXRAAQDFVQWLMDTK-K(COCH$_2$ONH$_2$)-CONH$_2$ |
| 2 | 4739 | HXQGTFTSDYSKYLDXRAAQDFVQWLMDTK-K(PEG2-COCH$_2$ONH$_2$)-CONH$_2$ |
| 3 | 4740 | HXQGTFTSDYSKYLDXRAAQDFVQWLMDTK-K(PEG4-COCH$_2$ONH$_2$)-CONH$_2$ |
| 4 | 5058 | HXQGTFTSDYSKYLDXRAAQDFVQWLMDTK-K(PEG6-COCH$_2$ONH$_2$)-CONH$_2$ |
| 5 | 5059 | HXQGTFTSDYSKYLDXRAAQDFVQWLMDTK-K(PEG8-COCH$_2$ONH$_2$)-CONH$_2$ |
| 6 | 5615 | HXQGTFTSDYSKYLDXRAAQDFVQWLMDTK-K(PEG24-COCH$_2$ONH$_2$)-CONH$_2$ |
| 7 | 6115 | HXQGTFTSDYSKYLDXRAAQDFVQWLMDTK-K(PEG36-COCH$_2$ONH$_2$)-CONH$_2$ |
| 8 | 5275 | HXDGTFTSDYSKYLDXRAAQDFVQWLMDTK-K(PEG4-COCH$_2$ONH$_2$)-CONH$_2$ |
| 9 | 5048 | HsQGTFTSDYSKYLDXRAAQDFVQWLMDTK-K(PEG2-COCH$_2$ONH$_2$)-CONH$_2$ |
| 10 | 5049 | HsQGTFTSDYSKYLDXRAAQDFVQWLMDTK-K(PEG4-COCH$_2$ONH$_2$)-CONH$_2$ |
| 11 | 5050 | HsQGTFTSDYSKYLDXRAAQDFVQWLMDTK-K(PEG6-COCH$_2$ONH$_2$)-CONH$_2$ |
| 12 | 5051 | HsQGTFTSDYSKYLDXRAAQDFVQWLMDTK-K(PEG8-COCH$_2$ONH$_2$)-CONH$_2$ |
| 13 | 6114 | HsQGTFTSDYSKYLDXRAAQDFVQWLMDTK-K(PEG24-COCH$_2$ONH$_2$)-CONH$_2$ |
| 14 | 4840 | HXQGTFTSDYSKYLDXRAAQDFV-K(COCH$_2$ONH$_2$)-WLMDTKQ-COOH |

TABLE 1-continued

| SEQ ID NO: | # | Peptide Structure |
|---|---|---|
| 15 | 4841 | HXQGTFTSDYSKYLDXRAAQDFV-K(PEG2-COCH$_2$ONH$_2$)-WLMDTKQ-COOH |
| 16 | 4842 | HXQGTFTSDYSKYLDXRAAQDFV-K(PEG4-COCH$_2$ONH$_2$)-WLMDTKQ-COOH |
| 17 | 5009 | HXQGTFTSDYSKYLDXRAAQDFV-K(PEG6-COCH$_2$ONH$_2$)-WLMDTKQ-COOH |
| 18 | 5010 | HXQGTFTSDYSKYLDXRAAQDFV-K(PEG8-COCH$_2$ONH$_2$)-WLMDTKQ-COOH |
| 19 | 5799 | HXQGTFTSDYSKYLDXRAAXDFV-K(PEG4-COCH$_2$ONH$_2$)-WLMXTKQ-COOH |
| 20 | 5052 | HsQGTFTSDYSKYLDXRAAQDFV-K(PEG2-COCH$_2$ONH$_2$)-WLMDTKQ-COOH |
| 21 | 5053 | HsQGTFTSDYSKYLDXRAAQDFV-K(PEG4-COCH$_2$ONH$_2$)-WLMDTKQ-COOH |
| 22 | 5314 | HsQGTFTSDYSKYLDXRAAQDFV-K(PEG2-COCH$_2$ONH$_2$)-WLMDT-CONH$_2$ |
| 23 | 5420 | HsQGTFTSDYSKYLDXRAAQDFV-K(PEG4-COCH$_2$ONH$_2$)-WLMDT-CONH$_2$ |
| 24 | 5798 | HXQGTFTSDYSKYLDXRAAQDFVEWLMKTK-K(PEG4-COCH$_2$ONH$_2$)-CONH$_2$ (lactam bridge between E and K) |
| 25 | 5759 | HXQGTFTSDYSKYLDXRAAQDFVQ-Bzt-LMDTK-K(PEG4-COCH$_2$ONH$_2$)-CONH$_2$ |
| 26 | 5760 | HXQGTFTSDYSKYLDXRAAQDFVQ-AzTrp-LMDTK-K(PEG4-COCH$_2$ONH$_2$)-CONH$_2$ |
| 27 | 5761 | HXQGTFTSDYSKYLDXRAAQDFVQ-2Nap-LMDTK-K(PEG4-COCH$_2$ONH$_2$)-CONH$_2$ |
| 28 | 5762 | HXQGTFTSDYSKYLDXRAAQDFVQ-3Pyr-LMDTK-K(PEG4-COCH$_2$ONH$_2$)-CONH$_2$ |
| 29 | 5763 | HXQGTFTSDYSKYLDXRAAQDFVQWLMDXK-K(PEG4-COCH$_2$ONH$_2$)-CONH$_2$ |
| 30 | 5764 | HXQGTFTSDYSKYLDXRAAQDFVQWL-M(O)-DTK-K(PEG4-COCH$_2$ONH$_2$)-CONH$_2$ |
| 31 | 5765 | HXQGTFTSDYSKYLDXRAAQDFVQWL-hLeu-DTK-K(PEG4-COCH$_2$ONH$_2$)-CONH$_2$ |
| 32 | 5766 | HXQGTFTSDYSKYLDXRAAQDFVQWL-hCha-DTK-K(PEG4-COCH$_2$ONH$_2$)-CONH$_2$ |
| 33 | 6052 | HXQGTFTSDYSKYLDXRAAQDFVQ-3Qui-LMDTK-K(PEG4-COCH$_2$ONH$_2$)-CONH$_2$ |
| 34 | 6053 | HXQGTFTSDYSKYLDXRAAQDFVQ-Bip-LMDTK-K(PEG4-COCH$_2$ONH$_2$)-CONH$_2$ |
| 35 | 6062 | HXQGTFTSDYSKYLDXRAAQDFVQ-Trp(Me)-LMDTK-K(PEG4-COCH$_2$ONH$_2$)-CONH$_2$ |
| 36 | 6376 | HXQGTFTSDYSKYLDXRAAQDFVQWXMDTK-K(PEG4-COCH$_2$ONH$_2$)-CONH$_2$ |
| 37 | 6377 | HXQGTFTSDYSKYLDXRAAQDFVQW-HFL-MDTK-K(PEG4-COCH$_2$ONH$_2$)-CONH$_2$ |
| 38 | 6378 | HXQGTFTSDYSKYLDXRAAQDFVQ-W(5OH)-LMDTK-K(PEG4-COCH$_2$ONH$_2$)-CONH$_2$ |
| 39 | 6379 | HXQGTFTSDYSKYLDXRAAQDFVQ-Lys-LMDTK-K(PEG4-COCH$_2$ONH$_2$)-CONH$_2$ |
| 40 | 6380 | HXQGTFTSDYSKYLDXRAAQDFVQ-Gln-LMDTK-K(PEG4-COCH$_2$ONH$_2$)-CONH$_2$ |
| 41 | 6381 | HXQGTFTSDYSKYLDXRAAQDFVQ-Asn-LMDTK-K(PEG4-COCH$_2$ONH$_2$)-CONH$_2$ |
| 42 | 6382 | HXQGTFTSDYSKYLDXRAAQDFVQ-αMePhe-LMDTK-K(PEG4-COCH$_2$ONH$_2$)-CONH$_2$ |
| 43 | 6383 | HXQGTFTSDYSKYLDXRAAQDFVQXLMDTK-K(PEG4-COCH$_2$ONH$_2$)-CONH$_2$ |
| 44 | 6384 | HXQGTFTSDYSKYLDXRAAQDFVQ-αMeLeu-LMDTK-K(PEG4-COCH$_2$ONH$_2$-CONH2 |
| 45 | 6385 | HXQGTFTSDYSKYLDXRAAQDFVQ-αMeTrp-LMDTK-K(PEG4-COCH$_2$ONH$_2$)-CONH$_2$ |
| 46 | 6386 | HXQGTFTSDYSKYLDXRAAQDFVQ-βhoTrp-LMDTK-K(PEG4-COCH$_2$ONH$_2$)-CONH$_2$ |
| 47 | 4699 | HXQGTFTSD-K(COCH$_2$ONH$_2$)-SKYLDXRAAQDFVQWLMDTKQ-COOH |
| 48 | 4700 | HXQGTFTSD-K(γE-COCH$_2$ONH$_2$)-SKYLDXRAAQDFVQWLMDTKQ-COOH |
| 49 | 4701 | HXQGTFTSD-K(γEγE-COCH$_2$ONH$_2$)-SKYLDXRAAQDFVQWLMDTKQ-COOH |
| 50 | 4702 | HXQGTFTSD-K(Peg2-COCH$_2$ONH$_2$)-SKYLDXRAAQDFVQWLMDTKQ-COOH |
| 51 | 4703 | HXQGTFTSD-K(Peg4-COCH$_2$ONH$_2$)-SKYLDXRAAQDFVQWLMDTKQ-COOH |
| 52 | 4896 | HXQGTFTSD-K(γEγE-Palm)SKYLDXRAAQDFV-K(COCH$_2$ONH$_2$)-WLMDTKQ-COOH |
| 53 | 4952 | HXQGTFTSD-K(γEγE-Palm)-SKYLDXRAAQDFV-K(PEG2-COCH$_2$ONH$_2$)-WLMDTKQ-COOH |

TABLE 1-continued

| SEQ ID NO: | # | Peptide Structure |
|---|---|---|
| 54 | 4953 | HXQGTFTSD-K(γEγE-Palm)-SKYLDXRAAQDFV-K(PEG4-COCH$_2$ONH$_2$)-WLMDTKQ-COOH |
| 55 | 5866 | HSQGTFTSDYSKYLSDRAAQDFVQWLMDTK-K(PEG4-COCH$_2$ONH$_2$)-CONH$_2$ |
| 56 | 6541 | HXQGTFTSDYSKYLDXRAAQDFVXWLMXTK-K(PEG24-COCH$_2$ONH$_2$)-CONH$_2$ |
| 57 | 6542 | HXQGTFTSDYSXYLDXRAAQDFVXWLMXTK-K(PEG24-COCH$_2$ONH$_2$)-CONH$_2$ |
| 58 | 6543 | HXQGTFTSDYSKYLDXRAAXDFVQWLMXTK-K(PEG24-COCH$_2$ONH$_2$)-CONH$_2$ |
| 59 | 6544 | HXQGTFTSDYSXYLDXRAACDFVQWLMXTK-(PEG24-COCH$_2$ONH$_2$)-CONH$_2$ |
| 60 | 6545 | HXQGTFTSDYSKYLDXRAAXDFVK(PEG24-COCH$_2$ONH$_2$)-WLMXTKQ-COOH |
| 61 | 6546 | HXQGTFTSDYSXYLDXRAAXDFVK(PEG24-COCH$_2$ONH$_2$)-WLMXTKQ-COOH |

X = α-aminobutyric acid (Aib); s = D-Ser; β-(3-benzothienyl)-alanine; AzTrp = 7 Azatryptophan; 2Nap = 2-naphthylalanine; 3Pyr = (3-Pyridyl)alanine; M(O) = methionine sulfoxide; hLeu = homoleucine; hCha = homocycloexylalanine; 3Qui = 3-(2quinoyl)-alanine; Bip = 4,4'-biphenylalanine; Trp(Me) = N-methyl-tryptophane; HFL = hexafluoroleucine; W(5OH) = 5-hydroxy tryptophan; αMePhe = alpha-methylphenylalanine; αMeLeu = alpha-methyl-leucine; αMeTrp = alpha-methyltryptophan; βhoTrp = beta homo tryptophan; γE = gamma glutamic acid; PEG = polyethylene glycol, wherein the interger indicates the number of ethylene units; Palm = palmitoyl (C15-CO-)

The Ambody is a derivative of palivizumab in which an amino acid at position 16, 32, 33, 56, 114, 179, 198, or 211 of the heavy chain is replaced with the non-natural amino acid para-acetylphenylalanine (pAcF) or an amino acid at position 125 or 142 of the light chain is replaced with pAcF. In particular embodiments, the light chain has the amino acid sequence shown in SEQ ID NO:64, SEQ ID NO:71, or SEQ ID NO:72 and the heavy chain has the amino acid shown in SEQ ID NO:65 or the amino acid sequence in SEQ ID NO:65 wherein the amino acid at position 16, 32, 33, 56, 114, 179, 198, or 211 has been replaced with pAcF with the proviso that if the light chain has the amino acid sequence of SEQ ID NO:71 or SEQ ID NO:72 then the heavy chain has the amino acid sequence shown in SEQ ID NO:65, or if the light chain has the amino acid sequence of SEQ ID NO:64 then the heavy chain has the amino acid sequence of SEQ ID NO:65 wherein at least one of positions 16, 32, 33, 56, 114, 179, 198, or 211 has been replaced with the non-natural amino acid pAcF. Amino acid sequences for each of the aforementioned heavy chains having a substitution of pAcF for the amino acid at position 16, 32, 33, 56, 114, 179, 198, or 211 are shown by SEQ ID NO:66, 67, 68, 69, 70, 73, 74, or 75, respectively.

Para-acetylphenylalanine has the structure

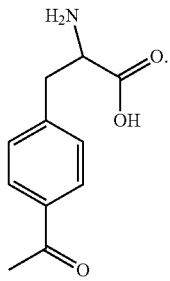

In a particular aspect, the pAcF residue of the ambody may be conjugated to the peptide via the aminooxy residue, which is directly conjugated to the epsilon amino group of a Lys residue of the peptide, in a linkage having the structure

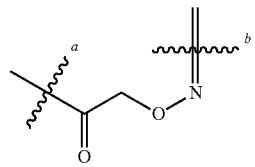 [SMILES: *C(=O)CON=*]

wherein the bond between the epsilon amino group of the Lys residue and the aminooxy residue is indicated by wavy line a and the bond between amino group of the aminooxy residue and the pAcF is indicated by wavy line b.

In a particular aspect, the pAcF residue of the ambody may be conjugated to the peptide via aminooxy residue, which is conjugated to the epsilon amino group of a Lys residue of the peptide via an amino polyethylene glycol spacer, in a linkage having the structure

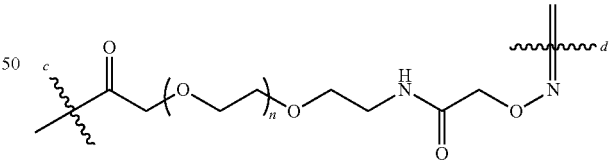

wherein the bond between the epsilon amino group of the Lys residue and the amino polyethylene gycol spacer is indicated by wavy line c and the bond between amino group of the aminooxy residue and the pAcF is indicated by wavy line d and wherein n is 1, 3, 5, 7, 23, or 35.

In a particular aspect, the pAcF residue of the ambody may be conjugated to the peptide via aminooxy residue, which is conjugated to the epsilon amino group of a Lys residue of the peptide via an amino polyethylene glycol spacer (Peg2), in a linkage having the structure

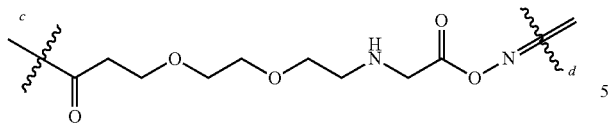

wherein the bond between the epsilon amino group of the Lys residue and the amino polyethylene gycol spacer is indicated by wavy line c and the bond between amino group of the aminooxy residue and the pAcF is indicated by wavy line d.

In a particular aspect, the pAcF residue of the ambody may be conjugated to the peptide via aminooxy residue, which is conjugated to the epsilon amino group of a Lys residue of the peptide via an amino polyethylene glycol spacer (Peg4), in a linkage having the structure

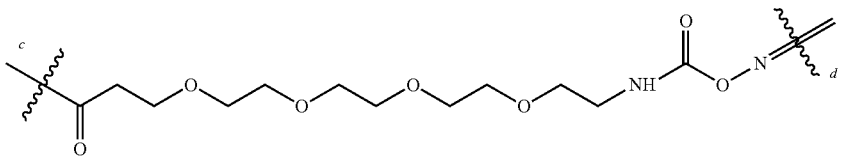 [SMILES: *C(=O)CCOCCOCCOCCOCCNC(=O)ON=*]

wherein the bond between the epsilon amino group of the Lys residue and the amino polyethylene gycol spacer is indicated by wavy line c and the bond between amino group of the aminooxy residue and the pAcF is indicated by wavy line d.

In a particular aspect, the pAcF residue of the ambody may be conjugated to the peptide via aminooxy residue, which is conjugated to the epsilon amino group of a Lys residue of the peptide via an amino polyethylene glycol spacer (Peg8), in a linkage having the structure

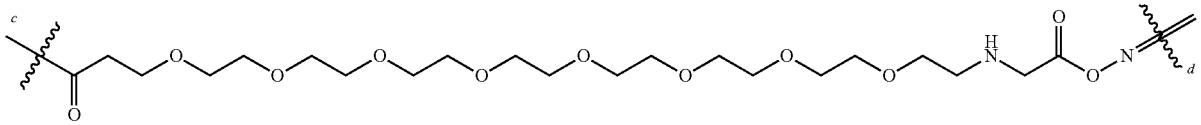 [SMILES: *C(=O)CCOCCOCCOCCOCCOCCOCCOCCOCCNCC(=O)ON=*]

wherein the bond between the epsilon amino group of the Lys residue and the amino polyethylene gycol spacer is indicated by wavy line c and the bond between amino group of the aminooxy residue and the pAcF is indicated by wavy line d.

In a particular aspect, the pAcF residue of the ambody may be conjugated to the peptide via aminooxy residue, which is conjugated to the epsilon amino group of a Lys residue of the peptide via an amino polyethylene glycol spacer (Peg24), in a linkage having the structure

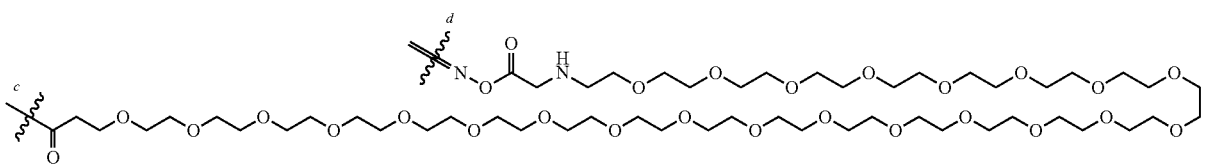 [SMILES: *C(=O)CCOCCOCCOCCOCCOCCOCCOCCOCCOCCOCCOCCOCCOCCOCCOCCOCCOCCOCCOCCOCCOCCOCCOCCOCCNCC(=O)ON=*]

wherein the bond between the epsilon amino group of the Lys residue and the amino polyethylene gycol spacer is indicated by wavy line c and the bond between amino group of the aminooxy residue and the pAcF is indicated by wavy line d.

In a particular aspect, the pAcF residue of the ambody may be conjugated to the peptide via aminooxy residue, which is conjugated to the epsilon amino group of a Lys residue of the peptide via an amino polyethylene glycol spacer (Peg36), in a linkage having the structure

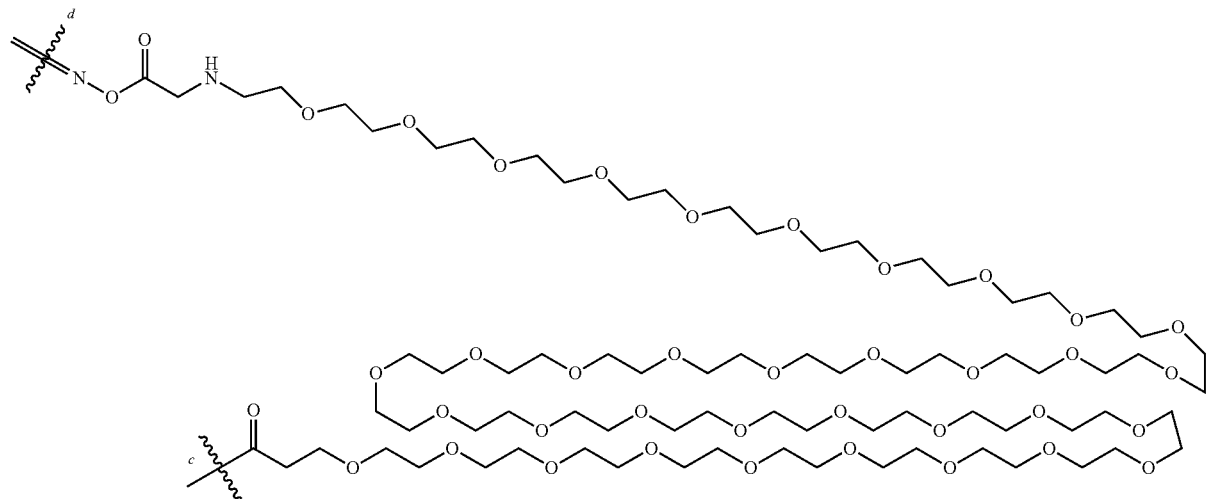 [SMILES: *C(=O)CCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCNCC(=O)ON=*]

wherein the bond between the epsilon amino group of the Lys residue and the amino polyethylene gycol spacer is indicated by wavy line c and the bond between amino group of the aminooxy residue and the pAcF is indicated by wavy line d.

In a particular aspect, the pAcF residue of the ambody may be conjugated to the peptide via aminooxy residue, which is conjugated to the epsilon amino group of a Lys residue of the peptide via a gamma-Glu (γE) spacer, in a linkage having the structure

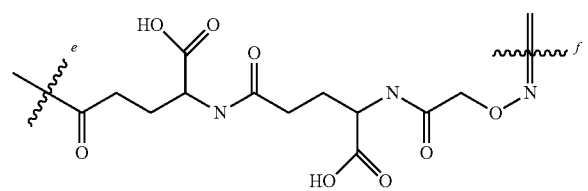 [SMILES: *C(=O)CCC(NC(=O)CCC(NC(=O)CON=*)C(=O)O)C(=O)O]

wherein the bond between the epsilon amino group of the Lys residue and the γE spacer is indicated by wavy line e and the bond between amino group of the aminooxy residue and the pAcF is indicated by wavy line f and wherein n is 1, 3, 5, 7, 23, or 37.

In a particular aspect, the pAcF residue of the ambody may be conjugated to the peptide via aminooxy residue, which is conjugated to the epsilon amino group of a Lys residue of the peptide via a gamma-Glu-gamma-Glu (γEyE) spacer, in a linkage having the structure

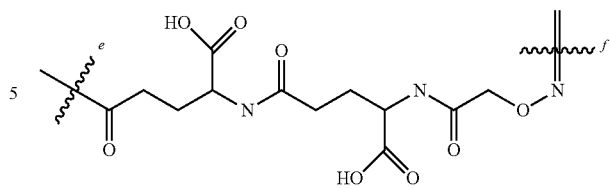

wherein the bond between the epsilon amino group of the Lys residue and the γEyE spacer is indicated by wavy line e and the bond between amino group of the aminooxy residue and the pAcF is indicated by wavy line f and wherein n is 1, 3, 5, 7, 23, or 37.

The ambodies may be modified to include a pAcF residue using the orthoganol tRNA technology disclosed in for example U.S. Pat. Nos. 7,045,337; 7,632,924; and 7,723,070, each incorporated herein by reference in its entirety. U.S. Published Application No. 20100093082 and Thildeaux et al., PloSOne 5(6): e11263 (2010), each incorporated herein by reference in its entirety, disclose use of orthoganol tRNA technology in vertebrete cells to produce proteins that include a pAF residue.

In general, a prokaryote or vertebrate host cell is transformed with nucleic acid molecules encoding an orthogonal tRNA-tRNA synthetase pair wherein the tRNA is preferentially charged with an unnatural amino acid (e.g., pAcF) and the tRNA recognizes a selector codon (e.g., amber codon). The host is then transformed with nucleic acid molecules encoding the heavy and light chains of the antibody with one or more selector codons at preselected locations within the nucleic acid sequence encoding the heavy or light chains. During translation of mRNA transcribed from the nucleic acid molecules, the host cell inserts an unnatural amino acid wherever in the mRNA sequence there is a selector codon. For example, if the mRNA encoding the heavy chain includes one selector codon, a heavy chain molecule will be produced that includes pAcF inserted at the location encoded by the selector codon. Assembly of the heavy chain molecules and the light chain molecules into an antibody molecule results in an antibody that has two pAcF residues.

Pharmaceutical Compositions

Further provided are pharmaceutical compositions, which comprise a therapeutically effective amount of one or more of the antibody peptide conjugates disclosed herein for the treatment of a metabolic disorder in an individual. Such disorders include, but are not limited to, obesity, metabolic syndrome or syndrome X, type II diabetes, complications of diabetes such as retinopathy, hypertension, dyslipidemias, cardiovascular disease, gallstones, osteoarthritis, and certain forms of cancers. The obesity-related disorders herein are associated with, caused by, or result from obesity.

"Obesity" is a condition in which there is an excess of body fat. The operational definition of obesity is based on the Body Mass Index (BMI), calculated as body weight per height in meters squared (kg/m2). "Obesity" refers to a condition whereby an otherwise healthy subject has a Body Mass Index (BMI) greater than or equal to 30 kg/m2, or a condition whereby a subject with at least one co-morbidity has a BMI greater than or equal to 27 kg/m2. An "obese subject" is an otherwise healthy subject with a Body Mass Index (BMI) greater than or equal to 30 kg/m2 or a subject with at least one co-morbidity with a BMI greater than or equal to 27 kg/m2. A "subject at risk for obesity" is an otherwise healthy subject with a BMI of 25 kg/m2 to less than 30 kg/m2 or a subject with at least one co-morbidity with a BMI of 25 kg/m2 to less than 27 kg/m2.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m2. In Asian countries, including Japan, an "obese subject" refers to a subject with at least one obesity-induced or obesity-related co-morbidity that requires weight reduction or that would be improved by weight reduction, with a BMI greater than or equal to 25 kg/m2. In Asian countries, a "subject at risk of obesity" is a subject with a BMI of greater than 23 kg/m2 to less than 25 kg/m2.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, non-alcoholic fatty liver disease (NAFLD), non-alcoholic steatohepatitis (NASH), fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "diabetes," as used herein, includes both insulin-dependent diabetes mellitus (IDDM, also known as type I diabetes) and non-insulin-dependent diabetes mellitus (NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

U.S. Pat. No. 6,852,690, which is incorporated herein by reference in its entirety, discloses methods for enhancing metabolism of nutrients comprising administering to a non-diabetic patient a formulation comprising a nutritively effective amount of one or more nutrients or any combination thereof and one or more insulinotropic peptides. The co-agonist peptides disclosed herein are insulinotropic and can be administered to patients with a disturbed glucose metabolism such as insulin resistance but no overt diabetes, as well as patients who for any reason cannot receive nutrition through the alimentary canal. Such patients include surgery patients, comatose patients, patients in shock, patients with gastrointestinal disease, patients with digestive hormone disease, and the like. In particular, obese patients, atherosclerotic patients, vascular disease patients, patients with gestational diabetes, patients with liver disease such as liver cirrhosis, patients with acromegaly, patients with glucocorticoid excess such as cortisol treatment or Cushings disease, patients with activated counterregulatory hormones such as would occur after trauma, accidents and surgery and the like, patients with hypertriglyceridemia and patients with chronic pancreatitis can be readily and suitably nourished according to the invention without subjecting the patient to hypo- or hyperglycemia. In particular, the administration to such a patient aims to provide a therapy to as rapidly as possible deliver the nutritional and caloric requirements to the patient while maintaining his plasma glucose below the so-called renal threshold of about 160 to 180 milligrams per deciliter of glucose in the blood. Although normal patients not having glucose levels just below the renal threshold can also be treated according to the invention as described above, patients with disturbed glucose metabolism such as hyperglycemic patients whose plasma glucose level is just above the renal threshold also find the therapy suitable for their condition. In particular, such patients who have a degree of hyperglycemia below the renal threshold at intermittent intervals can receive a combination treatment of nutrients plus insulinotropic peptides according to any of the following regimens. Normal patients not suffering from such hyperglycemia can also be treated using the peptide analogs disclosed herein.

The antibody peptide conjugates disclosed herein may be used in a pharmaceutical composition when combined with a pharmaceutically acceptable carrier. Such compositions comprise a therapeutically-effective amount of one or more of the antibody peptide conjugates disclosed herein and a pharmaceutically acceptable carrier. Such a composition may also be comprised of (in addition to the co-agonist peptides disclosed herein and a carrier) diluents, fillers, salts, buffers, stabilizers, solubilizers, and other materials well known in the art. Compositions comprising the co-agonist peptides disclosed herein can be administered, if desired, in the form of salts provided the salts are pharmaceutically acceptable. Salts may be prepared using standard procedures known to those skilled in the art of synthetic organic chemistry.

The term "individual" is meant to include humans and companion or domesticated animals such as dogs, cats, horses, and the like. Therefore, the compositions comprising a compound as disclosed herein are also useful for treating or preventing obesity and obesity-related disorders in cats and dogs. As such, the term "mammal" includes companion animals such as cats and dogs.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or prodrug formulations. It will be understood that, as used herein, references to the OXM analogs disclosed herein are meant to also include the pharmaceutically acceptable salts.

As utilized herein, the term "pharmaceutically acceptable" means a non-toxic material that does not interfere with the effectiveness of the biological activity of the active ingredient(s), approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils. The characteristics of the carrier will depend on the route of administration. The antibody peptide conjugates disclosed herein may be in multimers (for example, heterodimers or homodimers) or complexes with itself or other peptides. As a result, pharmaceutical compositions of the invention may comprise one or more antibody peptide conjugates disclosed herein in such multimeric or complexed form.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially, or simultaneously.

The pharmacological composition can comprise one or more antibody peptide conjugates disclosed herein; one or more antibody peptide conjugates disclosed herein and one or more other agents for treating a metabolic disorder; or the pharmacological composition comprising the one or more antibody peptide conjugates disclosed herein can be used concurrently with a pharmacological composition comprising an agent for treating a metabolic disorder. Such disorders include, but are not limited to, obesity, metabolic syndrome or syndrome X, type II diabetes, complications of diabetes, hypertension, dyslipidemias, cardiovascular disease, gallstones, osteoarthritis, and certain forms of cancers.

When the pharmacological composition comprises another agent for treating a metabolic disorder or the treatment includes a second pharmacological composition comprising an agent for treating a metabolic disorder, the agent includes, but are not limited to, cannabinoid (CB1) receptor antagonists, glucagon like peptide 1 (GLP-1) receptor agonists, glucagon receptor antagonists, lipase inhibitors, leptin, tetrahydrolipstatin, 2-4-dinitrophenol, acarbose, sibutramine, phentamine, fat absorption blockers, simvastatin, mevastatin, ezetimibe, atorvastatin, sitagliptin, metformin, orlistat, Qnexa, topiramate, naltrexone, bupriopion, phentermine, losartan, losartan with hydrochlorothiazide, and the like.

Examples of other active ingredients that may be administered separately or in the same pharmaceutical composition in combination with a co-agonist peptide as described herein include, but are not limited to:

(1) other dipeptidyl peptidase-IV (DPP-4) inhibitors (e.g., sitagliptin, alogliptin, linagliptin, vildagliptin, saxagliptin and omarigliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); (3) insulin or insulin analogs (e.g., insulin detemir, insulin glulisine, insulin degludec, insulin glargine, insulin lispro and inhalable formulations of each);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., such as those disclosed in WO 98/04528, WO 99/01423, WO 00/39088, and WO 00/69810);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof);

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g.,lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators;

(21) other agonists of the G-protein-coupled receptors: (i) GPR-109, (ii) GPR-119 (e.g., MBX2982 and PSN821), and (iii) GPR-40 (e.g., TAK875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)methoxy)phenyl)iso, 5-(4-((3-(2-methyl-6-(3-hydroxypropoxy)pyridine-3-yl)-2-methylphenyl)methoxy)phenyl)isothiazole-3-ol 1-oxide, and 5-[4-[[3-[4-(3-aminopropoxy)-2,6-dimethylphenyl]phenyl]methoxy]phenyl]isothiazole-3-ol 1-oxide);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, PF-04971729, remogliflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof, and

(37) FGF-21 and analogs and derivatives thereof;

(38) FGF21 mimetics such as agonist antibodies that binds the ß-Klotho and FCFR1c complex.

Of particular interest are metformin hydrochloride, pioglitazone, rosiglitazone, simvastatin, atorvastatin, or a sulfonylurea.

Antiobesity compounds that can be combined with the antibody peptide conjugates as disclosed herein include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CB1 receptor inverse agonists and antagonists (such as rimonabant and taranabant); $\beta_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see Chaki et al., "Recent advances in feeding suppressing agents: potential therapeutic strategy for the treatment of obesity," Expert Opin. Ther. Patents, 11: 1677-1692 (2001); Spanswick and Lee, "Emerging antiobesity drugs," Expert Opin. Emerging Drugs, 8: 217-237 (2003); Fernandez-Lopez, et al., "Pharmacological Approaches for the Treatment of Obesity," Drugs, 62: 915-944 (2002); and Gadde, et al., "Combination pharmaceutical therapies for obesity," Exp. Opin. Pharmacother., 10: 921-925 (2009).

In another aspect of the invention, a pharmaceutical composition is disclosed which comprises one or more of the following agents:

(a) an antibody peptide conjugate as disclosed herein;

(b) one or more compounds selected from the group consisting of:

(1) other dipeptidyl peptidase-IV (DPP-4) inhibitors;

(2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ dual agonists, such as ZYH1, YYH2, chiglitazar, GFT505, muraglitazar, aleglitazar, sodelglitazar, and naveglitazar, (2) PPARα agonists, such as fenofibric acid derivatives (e.g., gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors, such as ISI-113715, and TTP814;

(3) sulfonylurea and non-sulfonylurea insulin secretagogues, (e.g., tolbutamide, glyburide, glipizide, glimepiride, mitiglinide, and meglitinides, such as nateglinide and repaglinide);

(4) α-glucosidase inhibitors (e.g., acarbose, voglibose and miglitol);

(5) glucagon receptor antagonists;

(6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA: cholesterol acyltransferase inhibitors (e.g., avasimibe);

(7) HDL-raising drugs, such as niacin or a salt thereof and extended-release versions thereof; MK-524A, which is a combination of niacin extended-release and the DP-1 antagonist MK-524; and nicotinic acid receptor agonists;

(8) antiobesity compounds;

(9) agents intended for use in inflammatory conditions, such as aspirin, non-steroidal anti-inflammatory drugs (NSAIDs), glucocorticoids, and selective cyclooxygenase-2 (COX-2) inhibitors;

(10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers);

(11) glucokinase activators (GKAs) (e.g., AZD6370);

(12) inhibitors of 11β-hydroxysteroid dehydrogenase type 1 (e.g., such as those disclosed in U.S. Pat. No. 6,730, 690; WO 03/104207; and WO 04/058741);

(13) inhibitors of cholesteryl ester transfer protein (CETP), (e.g., torcetrapib and MK-0859);

(14) inhibitors of fructose 1,6-bisphosphatase (e.g., such as those disclosed in U.S. Pat. Nos. 6,054,587; 6,110, 903; 6,284,748; 6,399,782; and 6,489,476);

(15) inhibitors of acetyl CoA carboxylase-1 or 2 (ACC1 or ACC2);

(16) AMP-activated Protein Kinase (AMPK) activators;

(17) agonists of the G-protein-coupled receptors: (i) GPR-109, (ii) GPR-119 (e.g., MBX2982, and PSN821), and (iii) GPR-40 (e.g., TAK875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)methoxy)phenyl)iso, 5-(4-((3-(2-methyl-6-(3-hydroxypropoxy)pyridine-3-yl)-2-methylphenyl)methoxy)phenyl)isothiazole-3-ol 1-oxide, and 5-[4-[[3-[4-(3-aminopropoxy)-2,6-dimethylphenyl]phenyl]methoxy]phenyl]isothiazole-3-ol 1-oxide);

(18) SSTR3 antagonists (e.g., such as those disclosed in WO 2009/011836);

(19) neuromedin U receptor agonists (e.g., such as those disclosed in WO2009/042053, including, but not limited to, neuromedin S (NMS));

(20) inhibitors of stearoyl-coenzyme A delta-9 desaturase (SCD);

(21) GPR-105 antagonists (e.g., such as those disclosed in WO 2009/000087);

(22) inhibitors of glucose uptake, such as sodium-glucose transporter (SGLT) inhibitors and its various isoforms, such as SGLT-1; SGLT-2 (e.g., ASP1941, TS071, B110773, tofogliflozin, LX4211, canagliflozin, dapagliflozin and remogliflozin; and SGLT-3);

(23) inhibitors of acyl coenzyme A:diacylglycerol acyltransferase 1 and 2 (DGAT-1 and DGAT-2);

(24) inhibitors of fatty acid synthase;

(25) inhibitors of acyl coenzyme A:monoacylglycerol acyltransferase 1 and 2 (MGAT-1 and MGAT-2);

(26) agonists of the TGR5 receptor (also known as GPBAR1, BG37, GPCR19, GPR131, and M-BAR);

(28) bromocriptine mesylate and rapid-release formulations thereof; and

(29) IL-1b antibodies (e.g., XOMA052, and canakinumab);

(30) FGF-21 or analog or derivative;

(31) FGF21 mimetics such as agonist antibodies that binds the ß-Klotho and FCFR1c complex; and (c) a pharmaceutically acceptable carrier.

When an antibody peptide conjugate of the present invention is used contemporaneously with one or more other drugs, peptides, or proteins, a pharmaceutical composition containing such other drugs, peptides, or proteins in addition to the an antibody peptide conjugate of the present invention may be provided. Accordingly, the pharmaceutical compositions of the present invention include those that also contain one or more other active ingredients, in addition to a co-agonist peptide of the present invention.

Methods of administrating the pharmacological compositions comprising the an antibody peptide conjugate disclosed herein to an individual include, but are not limited to, intradermal, intramuscular, intraperitoneal, intravenous, subcutaneous, intranasal, epidural, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Intraventricular injection may be facilitated by an intraventricular catheter attached to a reservoir (for example, an Ommaya reservoir). Pulmonary administration may also be employed by use of an inhaler or nebulizer, and formulation with an aerosolizing agent. It may also be desirable to administer the one or more antibody peptide conjugates disclosed herein locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the antibody peptide conjugates disclosed herein including, but not limited to, encapsulation in liposomes, microparticles, microcapsules; minicells; polymers; capsules; tablets; and the like. In one embodiment, the antibody peptide conjugates disclosed herein may be delivered in a vesicle, in particular a liposome. In a liposome, the antibody peptide conjugates disclosed herein are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the antibody peptide conjugates disclosed herein can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (for example, the brain), thus requiring only a fraction of the systemic dose. See, for example, Goodson, In: *Medical Applications of Controlled Release*, 1984. (CRC Press, Bocca Raton, Fla.).

The amount of the compositions comprising one or more of the antibody peptide conjugates disclosed herein which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the composition with which to treat each individual patient. Initially, the attending physician will administer low doses of the composition and observe the patient's response. Larger doses of the composition may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. However, suitable dosage ranges for intravenous administration of the compositions comprising the one or more antibody peptide conjugates disclosed herein are generally about 5-500 micrograms (µg) of active compound per kilogram (Kg) body weight. Suitable dosage ranges for intranasal administration are generally about 0.01 pg/kg body weight to 1 mg/kg body weight.

Effective doses may be extrapolated from dose-response curves derived from in vitro or animal model test systems. Suppositories generally contain active ingredient in the range of 0.5% to 10% by weight; oral formulations preferably contain 10% to 95% active ingredient. Ultimately the attending physician will decide on the appropriate duration of therapy using compositions comprising the one or more co-agonist peptides disclosed herein of the present invention. Dosage will also vary according to the age, weight and response of the individual patient.

Further provided is a pharmaceutical pack or kit, comprising one or more containers filled with one or more of the ingredients of the pharmaceutical compositions and/or antibody peptide conjugates disclosed herein. Optionally associated with such container(s) may be a notice in the form prescribed by a governmental agency regulating the manufacture, use or sale of pharmaceuticals or biological products, which notice reflects approval by the agency of manufacture, use or sale for human administration.

The following examples are intended to promote a further understanding of the present invention.

Example 1

The peptides shown in Table 1 were synthesized by solid phase using Fmoc/t-Bu chemistry on a peptide multisynthesizer Symphony (Protein Technologies Inc.) on a Rink-amide PEG-PS resin, Champion (Biosearch Technologies, 150 μmol scale, loading 0.28 mmol/g) All the amino acids were dissolved at a 0.3 M concentration in DMF. The acylation reactions were performed for 45 min with 5-fold excess of activated amino acid over the resin free amino groups. The amino acids were activated with equimolar amounts of HATU (O-(7-azabenzotriazol-1-yl)-N, N,N',N'-tetramethyluronium hexafluorophosphate) solution 0.3 M in DMF, and a 2-fold molar excess of DIEA (N,N-diisopropylethylamine), solution 2M in NMP.

The side chain protecting groups were: tert-butyl for Ser, D-Ser, Thr and Tyr; trityl for Asn, Gln and His; tert-butoxycarbonyl for Lys, Trp; and, 2,2,4,6,7-pentamethyldihydrobenzofuran-5-sulfonyl for Arg; The N-terminal residue was acylated as Boc-His(Trt)-OH. To produce sequences having the C-terminal Gln-OH, sequence ID 14-21, 47-54 and 60-61, the Rink-amide PEG-PS resin was acylated with Fmoc-Glu-OtBu activated with equimolar amounts of HATU (O-(7-azabenzotriazol-1-yl)-N,N,N',N'-tetramethyluronium hexafluorophosphate) solution 0.3 M in DMF, and a 2-fold molar excess of DIEA (N,N-diisopropylethylamine), solution 2M in NMP. The lysine derivatized with the spacer residue and aminoxy functionality is incorporated either as Fmoc-Lys(Alloc)-OH (Alloc=allyloxycarbonyl) or Fmoc-Lys(Dde)-OH, Dde=[1-(4,4-dimethyl-2,6-dioxocyclohex-1-ylidene)ethyl]. The following no natural aminoacids: Fmoc-β-(3-benzothienyl)-alanine, Fmoc-L-7 Azatryptophan, Fmoc-L-2-naphthylalanine, Fmoc-L-(3-Pyridyl) alanine, Fmoc-L-methionine sulfoxide, Fmoc-L-homoleucine, Fmoc-L-homocycloexylalanine, Fmoc-L-3-(2quinoyl)-alanine, Fmoc-L-4,4'-biphenylalanine, Fmoc-L-N-methyl-tryptophane, Fmoc-L-hexafluoroleucine, Fmoc-L-5-hydroxy tryptophan, Fmoc-L-alpha-methylphenylalanine, Fmoc-L-alpha-methyl-leucine, Fmoc-L-alpha-methyltryptophan, Fmoc-L-β-homotryptophan where incorporated by manual coupling, using HOAt (Hydroxybenzoazatriazole) and DIC (N,N'-diisopropylcarbodiimide) as activators. At the end of the peptide assembly on solid phase, the Alloc protecting group was removed from either Lys31 or Lys24 or Lys10 with Pd(PPh$_3$)$_4$ and PhSiH$_3$, while the Dde protecting group was removed by treatment with a solution 2% of NH$_2$NH$_2$ in DMF. The side chain derivatization was performed by manual coupling of Bis-Boc aminoxy acetic acid or the appropriate PEG spacer residue and the Bis-Boc aminoxy acetic acid using HOAt and DIC as activators (4 fold excess for 4 hours). The amino PEG spacers are shown in Table 2.

TABLE 2

| Spacer NO: | Name | Spacers |
|---|---|---|
| 1 | PEG2 | H$_2$N-CH$_2$CH$_2$-O-CH$_2$CH$_2$-C(O)OH |
| 2 | PEG4 | H$_2$N-(CH$_2$CH$_2$O)$_3$-CH$_2$CH$_2$-C(O)OH |
| 3 | PEG6 | H$_2$N-(CH$_2$CH$_2$O)$_5$-CH$_2$CH$_2$-C(O)OH |
| 4 | PEG8 | H$_2$N-(CH$_2$CH$_2$O)$_7$-CH$_2$CH$_2$-C(O)OH |
| 5 | PEG24 | H$_2$N-(CH$_2$CH$_2$O)$_{23}$-CH$_2$CH$_2$-C(O)OH |
| 6 | PEG36 | H$_2$N-(CH$_2$CH$_2$O)$_{35}$-CH$_2$CH$_2$-C(O)OH |

For SEQ ID NO.52, 53, and 54, the Lys at position 24 was protected by the orthogonal Alloc (allyloxycarbonyl) group, while the Lys at position 10 was protected with Dde [1-(4, 4-dimethyl-2,6-dioxocyclohex-1-ylidene)ethyl] group. At the end of the peptide assembly on solid phase, the Dde protecting group was removed by treatment with a solution 2% of NH$_2$NH$_2$ in DMF and 200 molar excess of allyl alcohol and derivatization was performed by manual coupling of two Fmoc-Glu-OtBu residues and palmitic acid, activated with DIC and HOAt. After Lys10 derivatization, the Alloc protecting group was removed from Lys24 with Pd(PPh$_3$)$_4$ and PhSiH$_3$ and the side chain was assembled by manual coupling of Bis-Boc aminoxyacetic acid (SEQ ID NO. 51), Fmoc-N-amido-dPEG$_2$-acid and Bis-Boc aminoxyacetic acid (SEQ ID NO. 52), Fmoc-N-amido-dPEG$_4$-acid and Bis-Boc aminoxyacetic acid (SEQ ID NO. 54), activated with DIC and HOAt.

For SEQ ID NO:47, 48, 49, 50, and 51, Lys10 was derivatized with Bis-Boc aminoxyacetic acid, Fmoc-Glu-OtBu and Bis-Boc aminoxyacetic acid, two Fmoc-Glu-OtBu residues and Bis-Boc aminoxyacetic acid, Fmoc-N-amido-dPEG$_2$-acid and Bis-Boc aminoxyacetic acid, Fmoc-N-amido-dPEG$_4$-acid and Bis-Boc aminoxyacetic acid respectively. For SEQ ID NO.24, E24 and K28 were incorporated as Fmoc-L-glutamic acid 5-allyl ester and Fmoc-Lys(Alloc)-OH respectively, while K31 was orthogonally protected with ivDde [Fmoc-N$^\varepsilon$-1-(4,4-dimethyl-2,6-dioxocyclohex-1-ylidene)-3-methylbutyl-L-lysine]. The Alloc protective group was removed as previously described and lactam bridge was performed between E24 and K28, using Pyclock [(6-Chlorobenzotriazol-1-yloxy)tripyrrolidinophosphonium hexafluorophosphate], HOAt and DIPEA as activators. After lactam formation, the ivDde group on K31 was removed by treatment with a solution 2% of NH$_2$NH$_2$ in DMF and the side chain was assembled by manual coupling of Fmoc-N-amido-dPEG4-acid and Bis-Boc aminoxyacetic acid, activated with DIC and HOAt.

For various sequences, the following amino acid analogs were incorporated into the peptide at position 25 or 27.

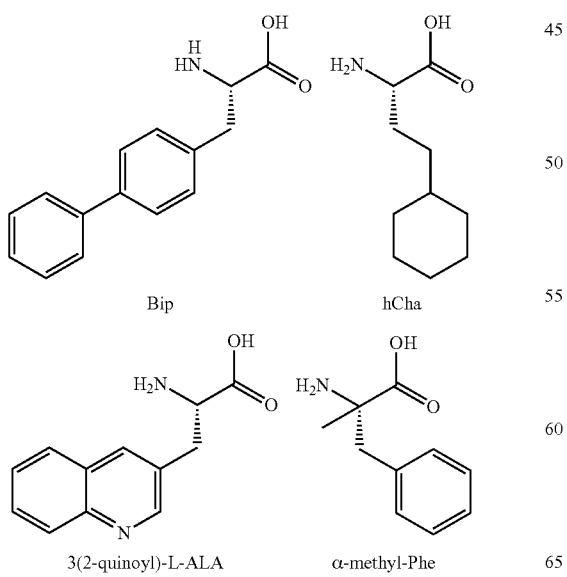

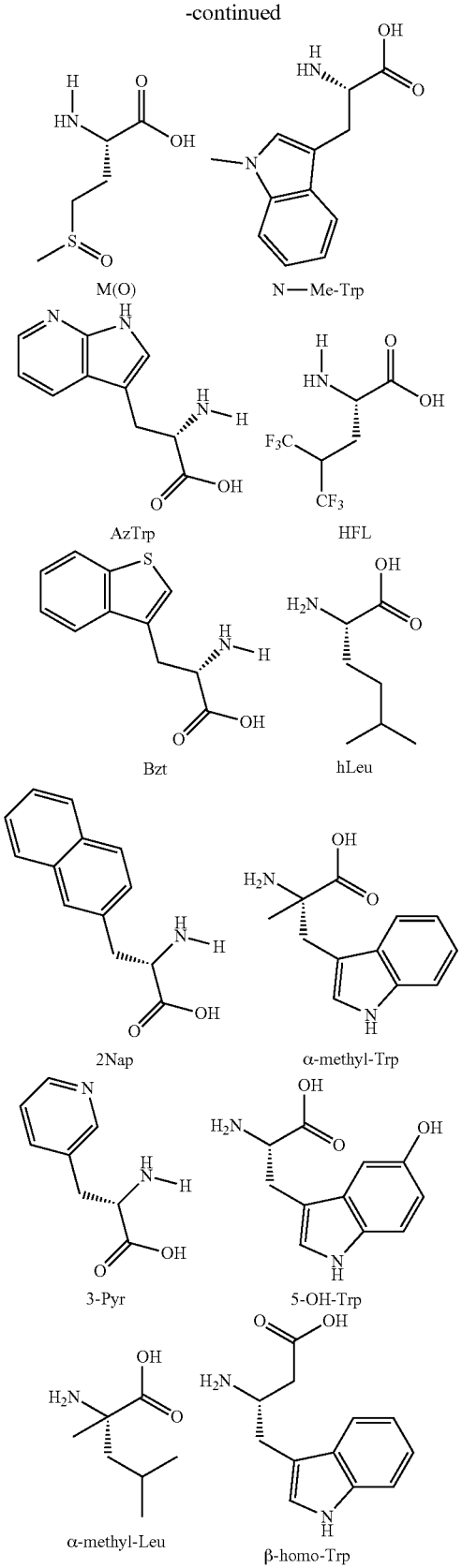

At the end of the synthesis, the dry peptide-resins were individually treated with 25 mL of the cleavage mixture, 88% TFA, 5% phenol, 2% triisopropylsilane and 5% water for 1.5 hours at room temperature. Each resin was filtered and the volume of the solution was reduced then added to cold methyl-t-butyl ether with 10% of aminoxy acetic acid. After centrifugation, the peptide pellets were washed with fresh cold methyl-t-butyl ether containing 10% of aminoxy acetic acid. The process was repeated twice. Final pellets were dried, resuspended in $H_2O$, 20% acetonitrile, and lyophilized.

The crude peptides (140 mg in 3 ml of DMSO) were purified by reverse-phase HPLC using preparative Waters) (Bridge C18 (50×150 mm, 5 µm, 100 Å) and using as eluents (A) 0.1% TFA in water and (B) 0.1% TFA in acetonitrile.

Analytical HPLC was performed on a Acquity UPLC Waters Chromatograph with a BEH130 C18 or BEH300 C4 Acquity Waters 2.1×100 mm, 1.7 µm, at 45° C., using H2O, 0.1% TFA (A) and CH3CN, 0.1% TFA (B) as solvents. The peptides were characterized by electrospray mass spectrometry on an Acquity SQ Detector.

Analytical Characterization of Peptides:

The purified peptide SEQ ID NO:1 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MH+ found: 3722.7 Da; Mw expected: 3723.09 Da).

The purified peptide SEQ ID NO:2 was characterized on an Acquity UPLC Waters Chromatograph, with BEH130 C18 Acquity Waters 2.1×100 mm, 1.7 µm, at 45° C., using H2O, 0.1% TFA (A) and $CH_3CN$, 0.1% TFA (B) as solvents and by electrospray mass spectrometry on an Acquity SQ Detector. (MW found: 3867.0 Da; MW expected: 3868.25 Da).

The purified peptide SEQ ID NO:3 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents. The peptides were characterized by electrospray mass spectrometry on an Acquity SQ Detector (MW found: 3970.5 Da; MW expected: 3970.38).

The purified peptide SEQ ID NO:4 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MW found: 4058.1 Da; MW expected: 4058.48 Da).

The purified peptide SEQ ID NO:5 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MW found: 4146.6 Da; MW expected: 4146.59 Da).

The purified peptide SEQ ID NO:6 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MW found: 4852.8 Da; MW expected: 4851.53 Da).

The purified peptide SEQ ID NO:7 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MW found: 5381.6 Da; MW expected: 5380.06 Da).

The purified peptide SEQ ID NO:8 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MW found: 3957.2 Da; Mw expected: 3957.34 Da).

The purified peptide SEQ ID NO:9 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MW found: 3869.7 Da; MW expected: 3870.22 Da).

The purified peptide SEQ ID NO:10 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MW found: 3972.6 Da; MW expected: 3972.35 Da).

The purified peptide SEQ ID NO:11 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MW found: 4060.2 Da; MW expected: 4060.46 Da).

The purified peptide SEQ ID NO:12 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MW found: 4148.4 Da; Mw expected: 4147.4 Da).

The purified peptide SEQ ID NO:13 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MW found: 4854.0 Da; Mw expected: 4853.4 Da).

The purified peptide SEQ ID NO:14 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MW found: 3723.0 Da; MW expected: 3724.07 Da).

The purified peptide SEQ ID NO:15 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents and by electrospray mass spectrometry on a Acquity SQ Detector. (MW found: 3868.8 Da; MW expected: 3869.23 Da).

The purified peptide SEQ ID NO:16 was characterized on an Acquity UPLC Waters Chromatograph, with BEH130 C18 Acquity Waters 2.1×100 mm, 1.7 µm, at 45° C., using $H_2O$, 0.1% TFA (A) and $CH_3CN$, 0.1% TFA (B) as solvents. The peptide was characterized by electrospray mass spectrometry on an Acquity SQ Detector. (MW found: 3970.8 Da; MW expected: 3971.36 Da).

The purified peptide SEQ ID NO:17 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 4059.6 Da; MW expected: 4059.47 Da).

The purified peptide SEQ ID NO:18 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 4146.6 Da; MW expected: 4147.57 Da).

The purified peptide SEQ ID NO:19 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3898.5 Da; MW expected: 3898.35 Da).

The purified peptide SEQ ID NO:20 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3871.9 Da; MW expected: 3871.2 Da).

The purified peptide SEQ ID NO:21 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3972.0 Da; MW expected: 3973.33 Da).

The purified peptide SEQ ID NO:22 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3613.8 Da; MW expected: 3613.92 Da).

The purified peptide SEQ ID NO:23 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: Da; MW expected: 3716.05 Da).

The purified peptide SEQ ID NO:24 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3967.5 Da; MW expected: 3966.43 Da).

The purified peptide SEQ ID NO:25 was characterized on an Acquity UPLC Waters Chromatograph, with BEH 300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3988.2 Da; MW expected: 3987.43 Da).

The purified peptide SEQ ID NO:26 was characterized on an Acquity UPLC Waters Chromatograph, with BEH 300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3971.1 Da; MW expected: 3971.37 Da).

The purified peptide SEQ ID NO:27 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3981.9 Da; MW expected: 3981.4 Da).

The purified peptide SEQ ID NO:28 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3932.7 Da; MW expected: 3932.33 Da).

The purified peptide SEQ ID NO:29 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3954.6 Da; MW expected: 3954.38 Da).

The purified peptide SEQ ID NO:30 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3987.0 Da; MW expected: 3986.38 Da).

The purified peptide SEQ ID NO:31 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3966.6 Da; MW expected: 3966.35 Da).

The purified peptide SEQ ID NO:32 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 4007.1 Da; MW expected: 4006.43 Da).

The purified peptide SEQ ID NO:33 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3983.7 Da; MW expected: 3982.39 Da).

The purified peptide SEQ ID NO:134 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 4008.6 Da; MW expected: 4007.4 Da).

The purified peptide SEQ ID NO:35 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3984.1 Da; MW expected: 3984.4 Da).

The purified peptide SEQ ID NO:36 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3943.2 Da; MW expected: 3943.31 Da).

The purified peptide SEQ ID NO:37 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 4079.4 Da; MW expected: 4079.3 Da).

The purified peptide SEQ ID NO:38 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3987.0 Da; MW expected: 3987.36 Da).

The purified peptide SEQ ID NO:39 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3913.5 Da; MW expected: 3913.32 Da).

The purified peptide SEQ ID NO:40 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3912.9 Da; MW expected: 3913.28 Da).

The purified peptide SEQ ID NO:41 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3899.7 Da; MW expected: 3898.27 Da).

The purified peptide SEQ ID NO:42 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3946.2 Da; MW expected: 3946.3 Da).

The purified peptide SEQ ID NO:43 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3869.7 Da; MW expected: 3870.26 Da).

The purified peptide SEQ ID NO:44 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3911.7 Da; MW expected: 3912.34 Da).

The purified peptide SEQ ID NO:45 was characterized on an Acquity UPLC Waters Chromatograph, with BEH300 C4 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3984.5 Da; MW expected: 3985.39 Da).

The purified peptide SEQ ID NO:46 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3689.1 Da; MW expected: 3689.03 Da).

The purified peptide SEQ ID NO:47 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3819.0 Da; MW expected: 3818.14 Da).

The purified peptide SEQ ID NO:48 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3947.4 Da; MW expected: 3947.26 Da).

The purified peptide SEQ ID NO:49 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3834.6 Da; MW expected: 3834.19 Da).

The purified peptide SEQ ID NO:50 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 3936.3 Da; MW expected: 3936.32 Da).

The purified peptide SEQ ID NO:51 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 4184.7 Da; MW expected: 4185.7 Da).

The purified peptide SEQ ID NO:52 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 4330.8 Da; MW expected: 4330.87 Da).

The purified peptide SEQ ID NO:53 was characterized on an Acquity UPLC Waters Chromatograph, with BEH130 C18 Acquity Waters 2.1×100 mm, 1.7 µm, at 45° C., using H$_2$O, 0.1% TFA (A) and CH$_3$CN, 0.1% TFA (B) as solvents and by electrospray mass spectrometry on a Acquity SQ Detector. (MW found: 4431.6 Da; MW expected: 4433.06 Da).

The purified peptide SEQ ID NO:54 was characterized on an Acquity UPLC Waters Chromatograph, with BEH130 C18 Acquity Waters 2.1×100 mm, 1.7 µm, at 45° C., using H2O, 0.1% TFA (A) and CH$_3$CN, 0.1% TFA (B) as solvents. The peptides were characterized by electrospray mass spectrometry on a Acquity SQ Detector (MW found: 3974 Da; MW expected: 3970.38 Da).

The purified peptide SEQ ID NO:55 was characterized on an Acquity UPLC Waters Chromatograph, with BEH130 C18 Acquity Waters 2.1×100 mm, 1.7 µm, at 45° C., using H2O, 0.1% TFA (A) and CH$_3$CN, 0.1% TFA (B) as solvents. The peptides were characterized by electrospray mass spectrometry on a Acquity SQ Detector (MW found: 3974.6 Da; MW expected: 3974.32 Da).

The purified peptide SEQ ID NO:56 was characterized on an Acquity UPLC Waters Chromatograph, with BEH130 C18 Acquity Waters 2.1×100 mm, 1.7 µm, at 45° C., using H2O, 0.1% TFA (A) and CH$_3$CN, 0.1% TFA (B) as solvents. The peptides were characterized by electrospray mass spectrometry on a Acquity SQ Detector (MW found: 4777.6 Da; MW expected: 4778.49 Da).

The purified peptide SEQ ID NO:57 was characterized on an Acquity UPLC Waters Chromatograph, with BEH130 C18 Acquity Waters 2.1×100 mm, 1.7 µm, at 45° C., using H2O, 0.1% TFA (A) and CH$_3$CN, 0.1% TFA (B) as solvents. The peptides were characterized by electrospray mass spectrometry on a Acquity SQ Detector (MW found: 4734.4 Da; MW expected: 4735.42 Da).

The purified peptide SEQ ID NO:58 was characterized on an Acquity UPLC Waters Chromatograph, with BEH130 C18 Acquity Waters 2.1×100 mm, 1.7 μm, at 45° C., using H2O, 0.1% TFA (A) and CH3CN, 0.1% TFA (B) as solvents. The peptides were characterized by electrospray mass spectrometry on a Acquity SQ Detector (MW found: 4777.3 Da; MW expected: 4778.49 Da).

The purified peptide SEQ ID NO:59 was characterized on an Acquity UPLC Waters Chromatograph, with BEH130 C18 Acquity Waters 2.1×100 mm, 1.7 μm, at 45° C., using H2O, 0.1% TFA (A) and CH3CN, 0.1% TFA (B) as solvents. The peptides were characterized by electrospray mass spectrometry on a Acquity SQ Detector (MW found: 4734.3 Da; MW expected: 4735.42 Da).

The purified peptide SEQ ID NO:60 was characterized on an Acquity UPLC Waters Chromatograph, with BEH130 C18 Acquity Waters 2.1×100 mm, 1.7 μm, at 45° C., using H2O, 0.1% TFA (A) and CH3CN, 0.1% TFA (B) as solvents. The peptides were characterized by electrospray mass spectrometry on a Acquity SQ Detector (MW found: 4778.5 Da; MW expected: 4779.47 Da).

The purified peptide SEQ ID NO:61 was characterized on an Acquity UPLC Waters Chromatograph, with BEH130 C18 Acquity Waters 2.1×100 mm, 1.7 μm, at 45° C., using H2O, 0.1% TFA (A) and CH3CN, 0.1% TFA (B) as solvents. The peptides were characterized by electrospray mass spectrometry on a Acquity SQ Detector (MW found: 4735.3 Da; MW expected: 4736.4 Da).

Example 2

Site specific conjugation using oxime chemistry was used to make the antibody peptide conjugates. The antibodies comprising para-acetyl phenylalanine (pAcF) were produced using The antibodies comprising pAcF were purified from clarified cell culture media by affinity chromatograph (AbSolute protein A, NovaSep) followed by cation exchange chromatography (SP 650S, Tosoh Biosciences).

The antibodies comprising pAcF were buffer exchanged into 50 mM sodium acetate; 200 mM glycine; 2.5% trehalose; 0-20% DMSO, pH 4.0-4.5 and concentrated to 1-20 mg/mL. 60 mM acetic hydrazide and 10-15 molar equivalents of peptide comprising aminooxy were added and reacted for 16-72 hours at 28-30° C. The reaction was monitored by LCMS. The antibody conjugates (APCs) were purified over a SP 650S column (Tosoh Biosciences) to remove excess reagents. The conjugates were buffer exchanged into 50 mM Histidine; 100 mM NaCl; 2.5% Trehalose; pH 6.0, 0.22 μm filtered, and stored at 4° C.

Conjugation Analysis.

Conjugation efficiencies and drug to antibody ratio (DAR) values were determined by LC-MS intact mass. The APCs were applied over a PLRP-S, 8 μm, 1000 Å column, 2.1×150 mm (Agilent) at 80° C. and eluted with a linear gradient from 25% B to 55% B over 20 minutes (A: Water, 0.05% TFA; B: Acetonitrile, 0.04% TFA). The mass spectra were obtained on an Agilent 6510 Q-Tof mass spectrometer with MassHunter software and deconvoluted using BioConfirm. DAR values were determined with relative peak abundances of the masses correlating to conjugated antibody.

Additionally, APCs were also analyzed by size-exclusion chromatography for monomer content. Purified APCs were applied onto a Tosoh G3000SWx1 5 μm column, 7.8×300 mm (Tosoh) using 0.2M potassium phosphate, 0.25M potassium chloride, 10% IPA pH 6.0 as the mobile phase. Target monomer content for the APCs was >95%.

Activity Measurement for APCs (cAMP)

APCs were received as aqueous solutions formulated in 50 mM L-histidine, 100 mM NaCl, 2.5% trehalose, pH 6.0. They were serially diluted in the same formulation buffer to generate 10 point titrations. The APC solutions were then transferred into 384-well assay plates (150 nl/well) using Echo (Labcyte). Assay ready frozen cells expressing human GLP-1R, human GCGR, mouse GLP1R and mouse GCGR were suspended in growth media consisting of DMEM medium (GIBCO), 10% FBS (GIBCO), 1×NEAA(GIBCO), 1× P/S (GIBCO), 200 ug/ml Hygromycin (GIBCO) and 10 ug/ml Blasticidin (GIBCO). Cells were then diluted in assay buffer consisting of PBS (GIBCO), 7.5% BSA (Perkin Elmer), 100 uM RO 20-1724 (Sigma), with or without 20% human (MP Biomedical) or mouse serum (Bioreclamation). The cell suspensions (15 ul) were then added to the assay plates containing the peptide solutions (30,000 cells/well for human GCGR, mouse GCGR, mouse GLP1R and 10,000 cells/well for human GLP1R). The assay plates were incubated for 1 hour at room temperature in the dark. Production of cAMP was determined using HitHunter™ cAMPXS kit (DiscoverX) following manufacturer protocol. The plates were incubated overnight at room temperature in the dark. Luminescence was measured using an EnVision Multilabel plate reader (Perkin Elmer). Native GLP-1 and Glucagon (Bachem) are used as control peptides. EC50 values were calculated using a 4 parameter logistic fit based on the Levenberg-Marquardt algorithm. Results are shown in Table 3.

TABLE 3

Measured Activities

| mAb | pAcF position* | Peptide Number | Human GCGR (nM) | Human GCGR 20% serum (nM) | Human GLP1R (nM) | Human GLP1R 20% serum (nM) |
|---|---|---|---|---|---|---|
| Ambody | HS32 | 4702 | IA | IA | ~31 | ~39 |
| Ambody | HS32 | 4704 | 1.67 | 2.98 | 4.6 | 2.8 |
| Ambody | HS32 | 4739 | 4.4 | 6.6 | 6.7 | 6.5 |
| Ambody | HS32 | 4740 | 3.8 | 4 | 3.8 | 5.7 |
| Ambody | HS32 | 4840 | 4.6 | 7.2 | 8.4 | 8.2 |
| Ambody | HS32 | 4841 | 2.9 | ~4.1 | 8.8 | 7.1 |
| Ambody | HS32 | 4842 | 4.5 | 4.9 | 7 | 6.2 |
| Ambody | HS32 | 4953 | 0.33 | 1.20 | 0.40 | 0.74 |
| Ambody | HS32 | 5009 | 3.1 | 3.6 | 3.5 | 5.3 |
| Ambody | HS32 | 5009 | ~3.1 | ~3.6 | ~3.5 | ~5.3 |
| Ambody | HS32 | 5010 | ~3.7 | ~3.9 | ~4.3 | 6.1 |
| Ambody | HS32 | 5048 | 3.10 | 3.4 | 7.1 | 7.4 |
| Ambody | HS32 | 5049 | 3.6 | 4.2 | 9.8 | 8.6 |
| Ambody | HS32 | 5050 | 4.4 | 4.0 | 10.5 | 8.5 |
| Ambody | HS32 | 5051 | 4.5 | 4.4 | 11 | 9.9 |
| Ambody | HS32 | 5052 | 1.6 | 1.8 | 16 | 13 |
| Ambody | HS32 | 5053 | 2.4 | 3.8 | 10.6 | 8.4 |
| Ambody | HS32 | 5058 | 2.5 | 2.8 | 1.7 | 2.3 |
| Ambody | HS32 | 5059 | 3.9 | 4.0 | 4.0 | 3.3 |
| Ambody | HS32 | 5275 | ~90 | >100 | 5.7 | 5.2 |
| Ambody | HS32 | 5307 | 2.4 | 3.5 | 6.5 | 5.4 |
| Ambody | HS32 | 5314 | 4.0 | 6.5 | 18.4 | 11.4 |
| Ambody | HS32 | 5420 | 3.7 | 7.2 | 9.7 | 8.8 |
| Ambody | HS32 | 5615 | 3.7 | 5.1 | 5.3 | 4.6 |
| Ambody | HS32 | 6115 | 2.64 | 4.05 | 3.34 | 3.36 |
| Ambody | HQ16 | 4740 | 7.2 | 8.0 | 2.7 | 3.3 |
| Ambody | HG33 | 4740 | 4.2 | 5.0 | 3.4 | 3.2 |
| Ambody | HD56 | 4740 | 5.6 | 9.1 | 1.9 | 2.2 |
| Ambody | HA114 | 4740 | 14.3 | 13.9 | 4.3 | 5.0 |
| Ambody | LK125 | 4740 | 54.8 | 65.9 | 9.4 | 10.4 |
| Ambody | LE142 | 4740 | 23.3 | 33.5 | 5.3 | 5.8 |
| Ambody | HS179 | 4740 | 40.5 | 49.4 | 7.6 | 7.7 |
| Ambody | HT198 | 4740 | 70.6 | 40 | 23.9 | 25.1 |
| Ambody | HN211 | 4740 | 28.8 | 31.3 | 7.9 | 7.1 |

TABLE 3-continued

| | | | Measured Activities | | | |
|---|---|---|---|---|---|---|
| mAb | pAcF position* | Peptide Number | Human GCGR (nM) | Human GCGR 20% serum (nM) | Human GLP1R (nM) | Human GLP1R 20% serum (nM) |
| Ambody | HD56 | 4740 | 10.61 | 10.39 | 4.56 | 3.36 |
| Ambody | HA114 | 4740 | 10 | 10.00 | 4.83 | 4.06 |
| Ambody | LE142 | 4740 | 36 | 38.66 | 7.77 | 7.07 |
| Ambody | HT198 | 5615 | 3.66 | 5.06 | 5.27 | 4.59 |
| Ambody | LK125 | 5615 | 7.35 | 9.95 | 5.10 | 5.41 |
| Ambody | HQ16 | 5615 | 4.16 | 5.64 | 6.58 | 5.51 |
| Ambody | HG33 | 4740 | 2.56 | 3.83 | 4.67 | 4.03 |
| Ambody | HA114 | 4740 | 9.07 | 11.50 | 5.50 | 5.06 |
| Ambody | LE142 | 5615 | 7.64 | 7.80 | 5.18 | 5.30 |
| Ambody | LK125 | 5615 | 4.79 | 8.50 | 6.43 | 6.60 |
| Ambody | HS32 | 5759 | 5.27 | 5.15 | 4.92 | 4.47 |
| Ambody | HS32 | 5760 | 3.22 | 3.44 | 3.62 | 2.85 |
| Ambody | HS32 | 5763 | 5.70 | 6.01 | 4.56 | 3.94 |
| Ambody | HS32 | 5764 | 6.23 | 5.38 | 8.19 | 5.40 |
| Ambody | HS32 | 5765 | 6.71 | 7.03 | 18.59 | 5.50 |
| Ambody | HS32 | 5761 | 2.85 | 4.83 | 5.31 | 4.92 |
| Ambody | HS32 | 5762 | 2.40 | 3.74 | 4.55 | 4.29 |
| Ambody | HS32 | 5762 | 2.40 | 3.74 | 4.55 | 4.29 |
| Ambody | HS32 | 5766 | 6.30 | 7.84 | 5.40 | 4.99 |
| Ambody | HS32 | 5799 | 2.86 | 5.44 | 5.25 | 4.70 |
| Ambody | HS32 | 5798 | 5.94 | 5.54 | 4.84 | 5.59 |
| Ambody | HS32 | 5866 | 3.50 | 4.32 | 4.82 | 4.39 |
| Ambody | HS32 | 6052 | 2.42 | 3.50 | 5.73 | 5.11 |
| Ambody | HS32 | 6053 | 3.99 | 4.57 | 4.73 | 4.13 |
| Ambody | HS32 | 6062 | 3.73 | 4.04 | 3.53 | 3.53 |
| Ambody | HS32 | 6376 | 9.86 | 10.4 | 6.73 | 6.27 |
| Ambody | HS32 | 6377 | 27.00 | 27.2 | 19.34 | 15.84 |
| Ambody | HS32 | 6378 | 6.01 | 6.5 | 8.06 | 6.61 |
| Ambody | HS32 | 6379 | 6.82 | 7.6 | 5.75 | 5.64 |
| Ambody | HS32 | 6380 | 3.56 | 3.99 | 4.03 | 3.17 |
| Ambody | HS32 | 6381 | 6.48 | 5.41 | 4.84 | 3.95 |
| Ambody | HS32 | 6382 | 4.10 | 4.15 | 4.27 | 3.54 |
| Ambody | HS32 | 6383 | 5.30 | 5.04 | 4.91 | 4.06 |
| Ambody | HS32 | 6384 | 3.40 | 3.90 | 4.69 | 4.18 |
| Ambody | HS32 | 6385 | 2.40 | 2.37 | 3.08 | 2.52 |
| Ambody | HS32 | 6541 | 25.06 | 16.36 | 5.63 | 5.17 |
| Ambody | HS32 | 6542 | 200.00 | >200 | 5.51 | 4.64 |
| Ambody | HS32 | 6543 | 7.34 | 8.73 | 5.30 | 4.64 |
| Ambody | HS32 | 6544 | 200.00 | >200 | 4.56 | 4.27 |
| Ambody | HS32 | 6545 | 5.59 | 5.49 | 3.65 | 4.02 |
| Ambody | HS32 | 6546 | 105.90 | 91.11 | 4.18 | 3.86 |

IA = inactive

*pAcF position - H or L is for heavy chain or light chain, followed by the amino acid replaced by the pAcF and its position in the amino acid sequence In Vivo Efficacy Model Male diet-induced obese (DIO) mice, which at 4-week-old were fed with high fat (60% kcal) diet D12492 to induce obesity. Mice were singly housed, acclimated and given free access to D12492 and water. Mice were divided into groups of sixteen mice per group based on initial average body weight. Each group of mice was intravenously injected once at day 0 with a dose of Antibody peptide conjugate (APC). The APCs studied were Ambody-HS32pAcF-Pep4740 @ 3 mg/kg, Ambody-HS32pAcF-Pep4704 @ 3 and 10 mg/kg, Ambody-HS32pAcF-Pep5615 @ 3 and 10 mg/kg. The administered doses used 50 Mm Histidine, 100 Mm NaCl, pH 6.0, 2.5% Trehalose as formulation buffer to make the doses. Body weight, food intake and were measured daily during treatment.

Figure 2:
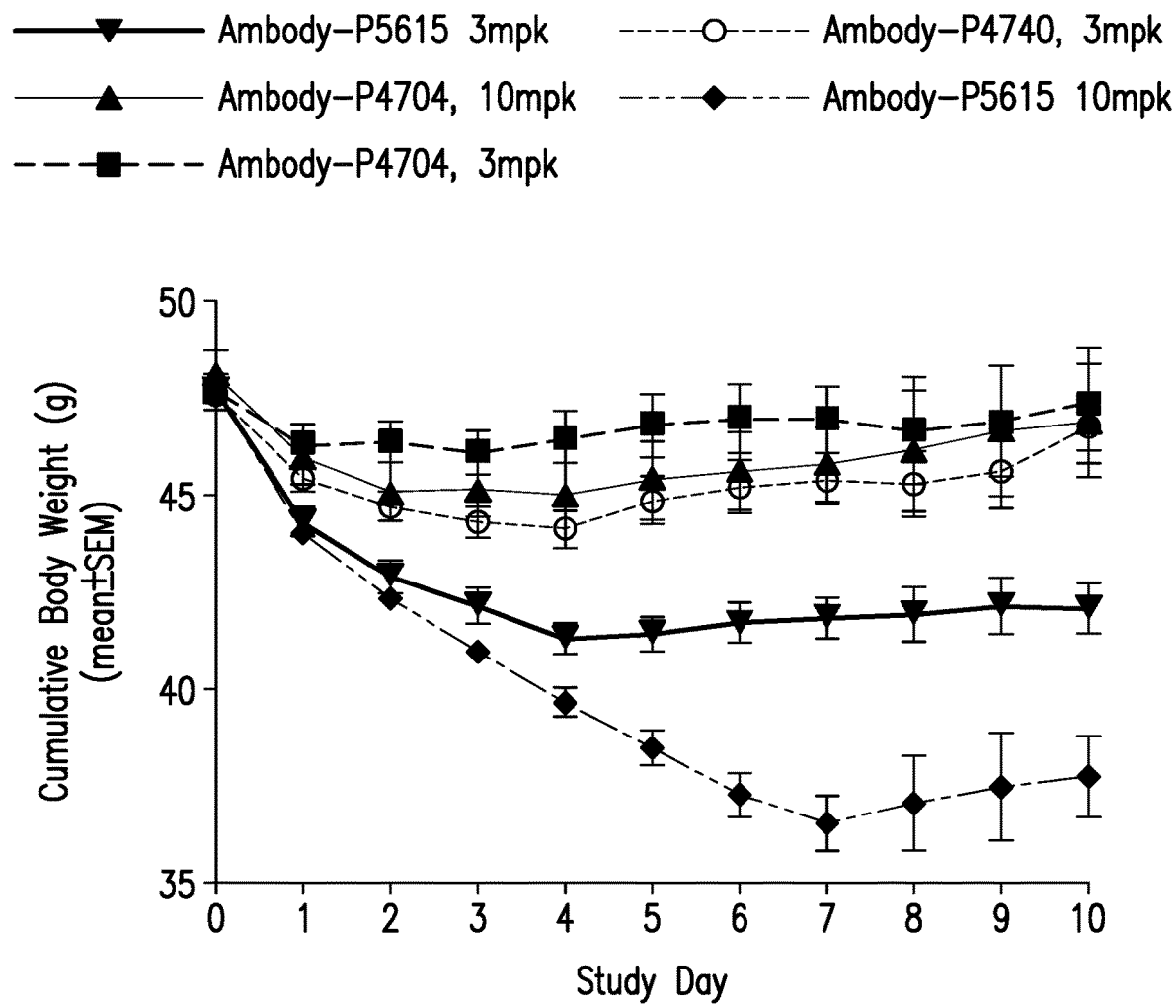
FIG. 2 shows a graph of the cumulative weight change (grams) of diet-induced obese (DIO) mice treated with Ambody-P4740 @ 3 mg/kg, Ambody-P4704 @ 3 and 10 mg/kg, Ambody-P5615 @ 3 and 10 mg/kg, single dose via tail vein injection on day 0.

The in vivo effects of Ambody-HS32pAcF-Pep4704, Ambody-HS32pAcF-Pep5615 of the invention were tested in diet-induced obese (DIO) mice that were maintained on a high fat diet for 20 weeks and had an initial body weight of about 48 grams. Mice were administered intravenously once at day 0. The APCs in this study included Ambody-HS32pAcF-Pep4740 at a dose of 3 mg/kg as a positive control. The Ambody-HS32pAcF-Pep4704 and Ambody-HS32pAcF-Pep5615 were administered at doses of 3 and 10 mg/kg, respectively. Cumulative body weight change (grams) was measured each day of the study except on day 3. Results are shown in FIG. 2 and are expressed as mean±SEM.

The Ambody-HS32pAcF-Pep5615 (Ambody-P5615) tested in this study demonstrated a significant ($p<0.0001$ vs Ambody-HS32pAcF-Pep4740 (Ambody-P4740), 1 way ANOVA) weight loss over the course of the study compared to the Ambody-HS32pAcF-Pep4740 treated groups of mice. On day 10 of the study, mice that were administered 3 mg/kg of the Ambody-HS32pAcF-Pep5615 (Ambody-P5615) exhibited an approximate weight loss of 5 grams, while a dose of 10 mg/kg of the Ambody-HS32pAcF-Pep5615 (Ambody-P5615) led to a body weight loss of 10.3 grams. Mice that were administered 3 mg/kg of the Ambody-HS32pAcF-Pep4740 (Ambody-P4740) exhibited weight loss of 0.92 grams. Mice that were administered 3 mg/kg and 10 mg/kg of the Ambody-HS32pAcF-Pep4704 (Ambody-P4704) exhibited approximately 0.55 grams and 1.0 grams of weight loss, respectively.

Figure 3:
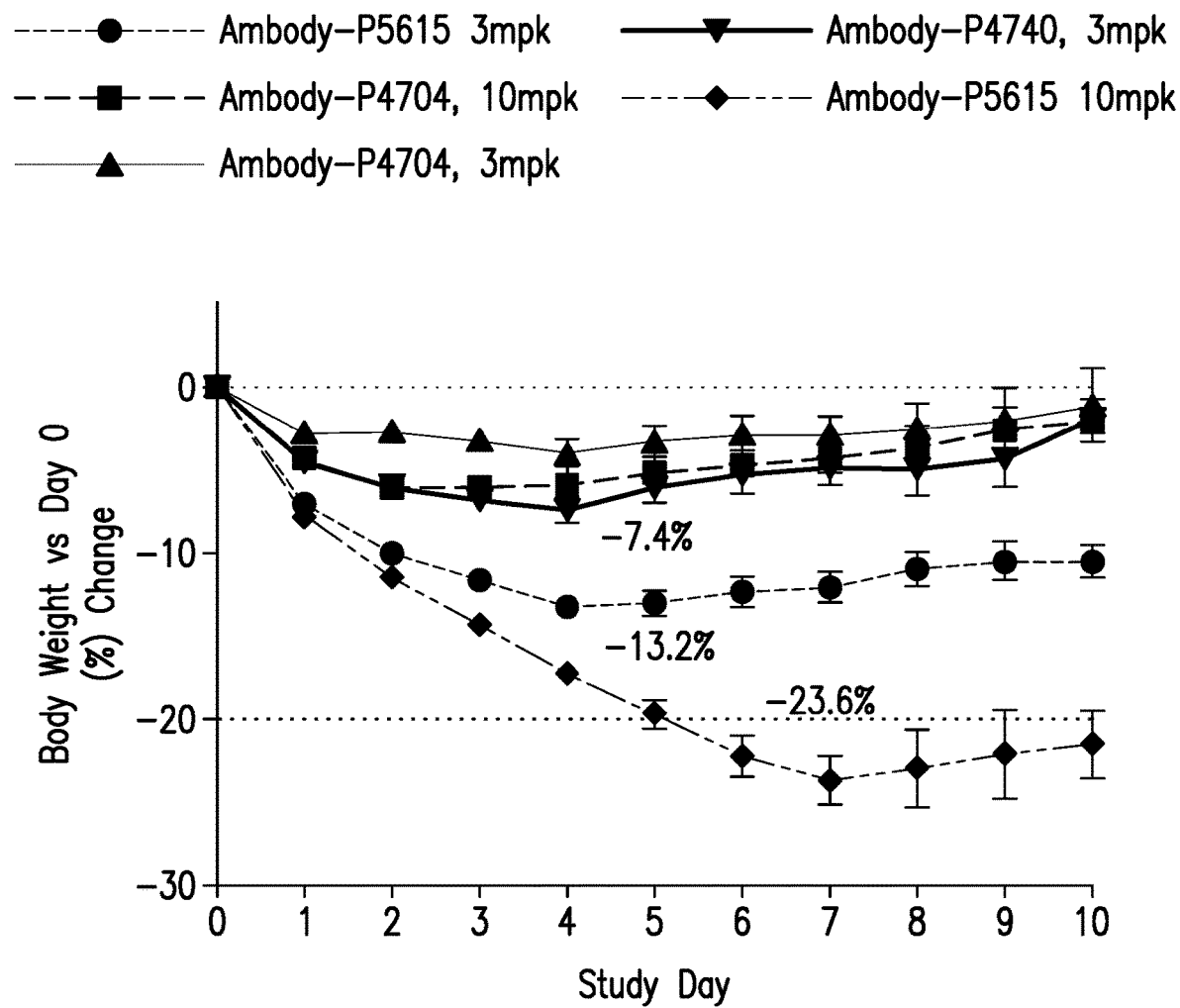
FIG. 3 shows a graph of the cumulative body weight change (%) relative to Ambody-P4740, a control group of DIO mice treated with a single IV dose of an Ambody-P4704, Ambody-P5615.

Body weight change is expressed as percent relative to Ambody-HS32pAcF-Pep4740 (FIG. 3). Mice administered a dose of 3 mg/kg the Ambody-HS32pAcF-Pep4740 (Ambody-P4740) exhibited approximately 1.9% weight loss at day 10 compared to mice administered with a dose of 3 mg/kg and 10 mg/kg the Ambody-HS32pAcF-Pep5615 (Ambody-P5615), who exhibited weight loss of approximately 10.5% or 21.5% respectively. Mice administered with a dose of 3 mg/kg the Ambody-HS32pAcF-Pep4704 (Ambody-P4704) exhibited weight loss of approximately 1.1%, while mice administered with a dose 10 mg/kg the Ambody-HS32pAcF-Pep4704 (Ambody-P4704) exhibited weight loss of approximately 2.0%.

Figure 4:
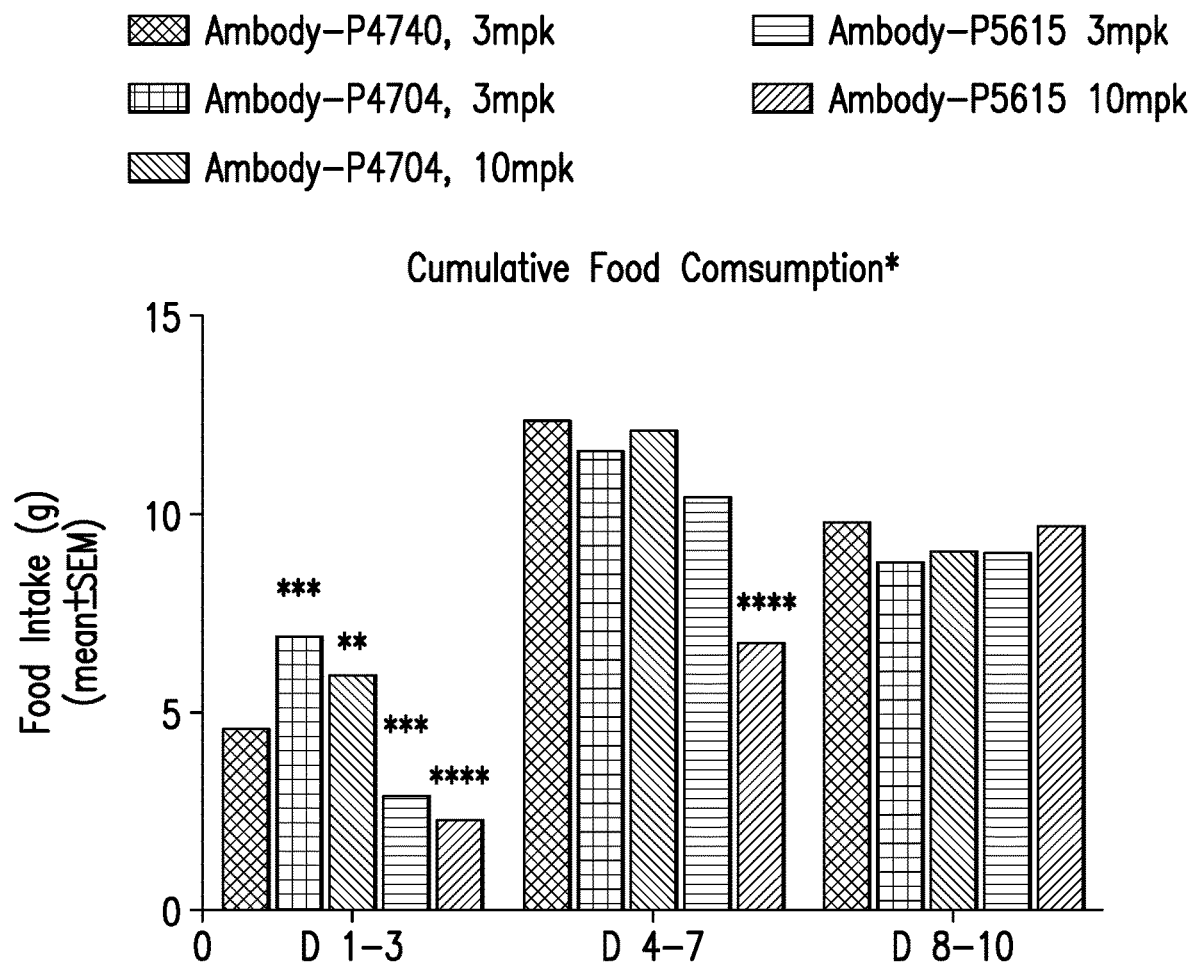
FIG. 4 shows a graph of the cumulative change in food intake of DIO mice treated with Ambody-P4740 @ 3 mg/kg, Ambody-P4704 @ 3 and 10 mg/kg, Ambody-P5615 @ 3 and 10 mg/kg, single dose via tail vein at day 0.

As shown in FIG. 4, DIO mice that were administered with Ambody-HS32pAcF-Pep4704, exhibited a significant less reduction in cumulative food intake after the first 3 days of dosing compare to Ambody-HS32pAcF-Pep4740 (Ambody-P4740) ($p<0.005$ *$p<0.001$****$p<0.0001$ vs Pep4740, 1way ANOVA, Newman-Keuls multiple comparisons). Mice that were administered with Ambody-HS32pAcF-Pep5615 (Ambody-P5615) exhibited a significant suppression of food intake at first 3 days. On day 4 to 7, there were no significant changes in food intake except the mice administered Ambody-HS32pAcF-Pep5615 (Ambody-P5615) at the 10 mg/kg. Day 8 through day 10, there were no changes in food intake.

In Vivo Plasma Exposure of APC Constructs

In vivo plasma exposure was monitored during the efficacy evaluation of APCs in DIO mice (mouse model and efficacy evaluation described under 'In vivo efficacy model section'). All groups received an intravenous single bolus dose at day 0 of APC. The APCs studied were Ambody-HS32pAcF-Pep4740 @ 3 mg/kg, Ambody-HS32pAcF-Pep4704 @ 3 and 10 mg/kg, Ambody-HS32pAcF-Pep5615 @ 3 and 10 mg/kg. The administered doses used 50 Mm Histidine, 100 Mm NaCl, pH 6.0, 2.5% Trehalose as formulation buffer to make the doses. Whole blood was collected on Day 1, 3, 7 and 10 in test tubes pretreated with dipotassium-EDTA and processed to plasma by centrifugation (4000 g, 2-8° C.). Plasma concentration was measured by conjugate immunoassay as described below.

Quantitation of Circulating APC Compounds in Mouse Serum (Conjugate Immunoassay)

A two site sandwich immunoassay was set up to quantitate the APCs on the Meso Scale Discovery (MSD) assay platform (Meso Scale Discovery). MSD Streptavidin Gold Multi-Array 96-Well Plate was blocked with 150 µL of 5% BSA in PBS and incubated overnight at 4° C. at 50 rpm shaking. The plate was washed 3 times using 200 µL of Wash Buffer (PBS with 0.05% Tween 20) and was coated with capture antibody (Merck & Co., Inc., Biotinylated Mouse×[GCG_H] mAb, TC140.20F1.C1 IgG2b/Kappa) using a volume of 25 µL per well at 2 µg/mL in Assay Buffer (0.5% BSA [wt/v], 0.05% Tween 20 [v/v], 0.25% CHAPS [wt/v], 5 mM EDTA in PBS) and incubated for 1 hour at room temperature at 600 rpm. The plate was washed 3 times with Wash Buffer and 25 µL of MSD Diluent 4 was added into each well. Then 25 µL of calibrators, controls, and samples were added into designated wells. The APC calibrators were made for each APC as an eight-point curve starting at 500 ng/mL and by serially diluting 1:4 to 0.12 ng/mL at point 7. Calibrator point 8 was 2% mouse plasma in Assay Buffer for assay background. The serum samples were diluted at a minimum of 1:50 with Assay Buffer. The plate was then placed on a plate shaker for 2 hours at room temperature at 600 rpm. Following a wash step as described before, 25 µL of the detector antibody (Mouse anti-Hu IgG4, Southern Biotech Clone HP6025, conjugated with MSD ST-label ruthenium tris-bipyridine chelate according to manufacturer's protocol) was added at a concentration of 1 µg/mL in Assay Buffer. Following a one hour incubation at room temperature at 600 rpm, the plate was washed as described above and processed in MSD Meso Sector S 600 instrument to measure electrochemiluminescence signal according to manufacturer's protocol.

Figure 5:
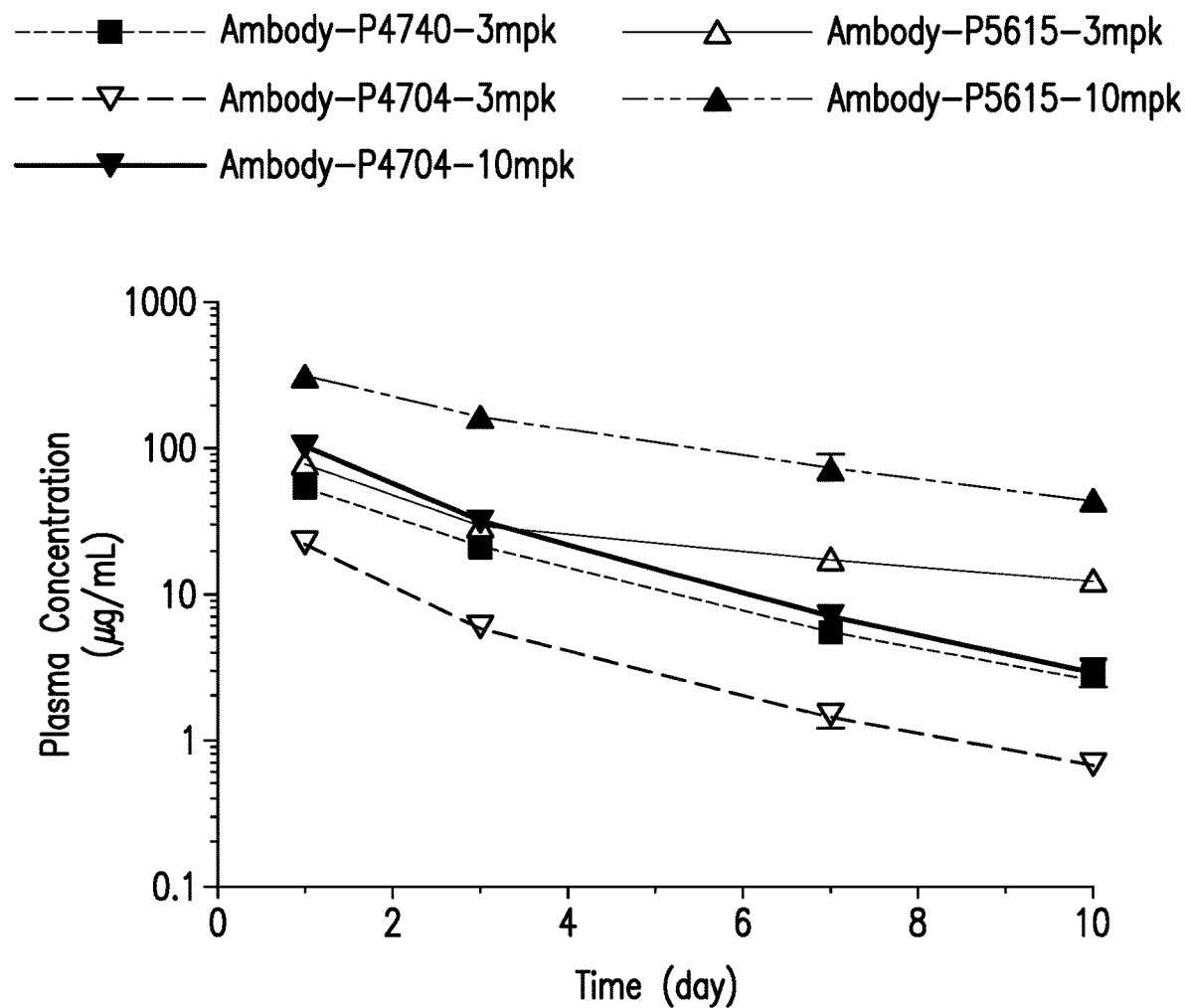
FIG. 5 shows the plasma concentration in DIO mice treated with Ambody-4740 @ 3 mg/kg, Ambody-4704 @ 3 and 10 mg/kg, Ambody-5615 @ 3 and 10 mg/kg, single dose via tail vein at day 1, 3, 7 and 10. Values are mean±SD, n=4.

FIG. 5 demonstrates the impact of spacer design on circulatory stability of the conjugated APC. At comparable doses, Ambody-HS32pAcF-Pep5615 (Ambody-5615) had the highest plasma exposure followed by Ambody-HS32pAcF-Pep4740 (Ambody-4740) and then Ambody-HS32pAcF-Pep4704 (Ambody-4704). The results show that by increasing the length of the spacer for linking the peptide to the antibody, the serum half-life of the peptide could be extended or enhanced.

TABLE 4

ANTIBODY SEQUENCES

| SEQ ID NO: | Description | Amino Acid Sequence |
|---|---|---|
| 64 | Palivizumab Light Chain | DIQMTQSPSTLSASVGDRVTITCKCQLSVGYMEIWYQQKPGKAPKLL IYDTSKLASGVPSRFSGSGSGTEFTLTISSLQPDDFATYYCFQGSGY PFTFGGGTKLEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC |
| 65 | Antibody Heavy Chain | QVTLRESGPALVKPTQTLTLTCTFSGFSLSTSGMSVGWIRQPPGKAL EWLADIWWDDKKDYNPSLKSRLTISKDTSKNQVVLKVTNMDPADTAT YYCARSMITNWYFDVWGAGTTVTVSSASTKGPSVFPLAPCSRSTSES TAALGCLVKDYFPEPVTVSWNSGALTSGVHTFPAVLQSSGLYSLSSV VTVPSSSLGTKTYTCNVDHKPSNTKVDKRVESKYGPPCPPCPAPEFE GGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLP SSIEKTISKAKGQPREPQVYTLPPSQEEMTKNQVSLTCLVKGFYPSD IAVEWESNGQPENNYKTTPPVLDSDGSFFLYSRLTVDKSRWQEGNVF SCSVMHEALHNHYTQKSLSLSLG |
| 66 | Ambody Heavy Chain HS32 X at 32 = pAcF | QVTLRESGPALVKPTQTLTLTCTFSGFSLSTXGMSVGWIRQPPGKAL EWLADIWWDDKKDYNPSLKSRLTISKDTSKNQVVLKVTNMDPADTAT YYCARSMITNWYFDVWGAGTTVTVSSASTKGPSVFPLAPCSRSTSES TAALGCLVKDYFPEPVTVSWNSGALTSGVHTFPAVLQSSGLYSLSSV VTVPSSSLGTKTYTCNVDHKPSNTKVDKRVESKYGPPCPPCPAPEFE GGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLP SSIEKTISKAKGQPREPQVYTLPPSQEEMTKNQVSLTCLVKGFYPSD IAVEWESNGQPENNYKTTPPVLDSDGSFFLYSRLTVDKSRWQEGNVF SCSVMHEALHNHYTQKSLSLSLG |
| 67 | Ambody Heavy Chain HQ16 X at 16 = pAcF | QVTLRESGPALVKPTXTLTLTCTFSGFSLSTSGMSVGWIRQPPGKAL EWLADIWWDDKKDYNPSLKSRLTISKDTSKNQVVLKVTNMDPADTAT YYCARSMITNWYFDVWGAGTTVTVSSASTKGPSVFPLAPCSRSTSES TAALGCLVKDYFPEPVTVSWNSGALTSGVHTFPAVLQSSGLYSLSSV VTVPSSSLGTKTYTCNVDHKPSNTKVDKRVESKYGPPCPPCPAPEFE GGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLP SSIEKTISKAKGQPREPQVYTLPPSQEEMTKNQVSLTCLVKGFYPSD IAVEWESNGQPENNYKTTPPVLDSDGSFFLYSRLTVDKSRWQEGNVF SCSVMHEALHNHYTQKSLSLSLG |
| 68 | Ambody Heavy Chain HG33 X at 33 = pAcF | QVTLRESGPALVKPTQTLTLTCTFSGFSLSTSXMSVGWIRQPPGKAL EWLADIWWDDKKDYNPSLKSRLTISKDTSKNQVVLKVTNMDPADTAT YYCARSMITNWYFDVWGAGTTVTVSSASTKGPSVFPLAPCSRSTSES TAALGCLVKDYFPEPVTVSWNSGALTSGVHTFPAVLQSSGLYSLSSV VTVPSSSLGTKTYTCNVDHKPSNTKVDKRVESKYGPPCPPCPAPEFE GGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLP SSIEKTISKAKGQPREPQVYTLPPSQEEMTKNQVSLTCLVKGFYPSD IAVEWESNGQPENNYKTTPPVLDSDGSFFLYSRLTVDKSRWQEGNVF SCSVMHEALHNHYTQKSLSLSLG |

TABLE 4-continued

ANTIBODY SEQUENCES

| SEQ ID NO: | Description | Amino Acid Sequence |
|---|---|---|
| 69 | Ambody Heavy Chain HD56 X at 56 = pAcF | QVTLRESGPALVKPTQTLTLTCTFSGFSLSTSGMSVGWIRQPPGKAL EWLADIWWXDKKDYNPSLKSRLTISKDTSKNQVVLKVTNMDPADTAT YYCARSMITNWYFDVWGAGTTVTVSSASTKGPSVFPLAPCSRSTSES TAALGCLVKDYFPEPVTVSWNSGALTSGVHTFPAVLQSSGLYSLSSV VTVPSSSLGTKTYTCNVDHKPSNTKVDKRVESKYGPPCPPCPAPEFE GGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLP SSIEKTISKAKGQPREPQVYTLPPSQEEMTKNQVSLTCLVKGFYPSD IAVEWESNGQPENNYKTTPPVLDSDGSFFLYSRLTVDKSRWQEGNVF SCSVMHEALHNHYTQKSLSLSLG |
| 70 | Ambody Heavy Chain HT114 X at 114 = pAcF | QVTLRESGPALVKPTQTLTLTCTFSGFSLSTSGMSVGWIRQPPGKAL EWLADIWWDDKKDYNPSLKSRLTISKDTSKNQVVLKVTNMDPADTAT YYCARSMITNWYFDVWGAGXTVTVSSASTKGPSVFPLAPCSRSTSES TAALGCLVKDYFPEPVTVSWNSGALTSGVHTFPAVLQSSGLYSLSSV VTVPSSSLGTKTYTCNVDHKPSNTKVDKRVESKYGPPCPPCPAPEFE GGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLP SSIEKTISKAKGQPREPQVYTLPPSQEEMTKNQVSLTCLVKGFYPSD IAVEWESNGQPENNYKTTPPVLDSDGSFFLYSRLTVDKSRWQEGNVF SCSVMHEALHNHYTQKSLSLSLG |
| 71 | Ambody Light Chain LK125 X at 125 = pAcF | DIQMTQSPSTLSASVGDRVTITCKCQLSVGYMHWYQQKPGKAPKLLI YDTSKLASGVPSRFSGSGSGTEFTLTISSLQPDDFATYYCFQGSGYP FTFGGGTKLEIKRTVAAPSVFIPPPSDEQLXSGTASVVCLLNNFYPR EAKVQWKVDNALQSGNSQESVTEQDSKDSTYSLSSTLTLSKADYEKH KVYACEVTHQGLSSPVTKSFNRGEC |
| 72 | Ambody Light Chain LE142 X at 142 = pAcF | DIQMTQSPSTLSASVGDRVTITCKCQLSVGYMHWYQQKPGKAPKLLI YDTSKLASGVPSRFSGSGSGTEFTLTISSLQPDDFATYYCFQGSGYP FTFGGGTKLEIKRTVAAPSVFIPPPSDEQLKSGTASVVCLLNNFYPR XAKVQWKVDNALQSGNSQESVTEQDSKDSTYSLSSTLTLSKADYEKH KVYACEVTHQGLSSPVTKSFNRGEC |
| 73 | Ambody Heavy Chain HS179 X at 179 = pAcF | QVTLRESGPALVKPTQTLTLTCTFSGFSLSTSGMSVGWIRQPPGKAL EWLADIWWDDKKDYNPSLKSRLTISKDTSKNQVVLKVTNMDPADTAT YYCARSMITNWYFDVWGAGTTVTVSSASTKGPSVFPLAPCSRSTSES TAALGCLVKDYFPEPVTVSWNSGALTSGVHTFPAVLQXSGLYSLSSV VTVPSSSLGTKTYTCNVDHKPSNTKVDKRVESKYGPPCPPCPAPEFE GGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLP SSIEKTISKAKGQPREPQVYTLPPSQEEMTKNQVSLTCLVKGFYPSD IAVEWESNGQPENNYKTTPPVLDSDGSFFLYSRLTVDKSRWQEGNVF SCSVMHEALHNHYTQKSLSLSLG |
| 74 | Ambody Heavy Chain HT198 X at 198 = pAcF | QVTLRESGPALVKPTQTLTLTCTFSGFSLSTSGMSVGWIRQPPGKAL EWLADIWWDDKKDYNPSLKSRLTISKDTSKNQVVLKVTNMDPADTAT YYCARSMITNWYFDVWGAGTTVTVSSASTKGPSVFPLAPCSRSTSES TAALGCLVKDYFPEPVTVSWNSGALTSGVHTFPAVLQSSGLYSLSSV VTVPSSSLGXKTYTCNVDHKPSNTKVDKRVESKYGPPCPPCPAPEFE GGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLP SSIEKTISKAKGQPREPQVYTLPPSQEEMTKNQVSLTCLVKGFYPSD IAVEWESNGQPENNYKTTPPVLDSDGSFFLYSRLTVDKSRWQEGNVF SCSVMHEALHNHYTQKSLSLSLG |
| 75 | Ambody Heavy Chain HN211 X at 211 = pAcF | QVTLRESGPALVKPTQTLTLTCTFSGFSLSTSGMSVGWIRQPPGKAL EWLADIWWDDKKDYNPSLKSRLTISKDTSKNQVVLKVTNMDPADTAT YYCARSMITNWYFDVWGAGTTVTVSSASTKGPSVFPLAPCSRSTSES TAALGCLVKDYFPEPVTVSWNSGALTSGVHTFPAVLQSSGLYSLSSV VTVPSSSLGTKTYTCNVDHKPSXTKVDKRVESKYGPPCPPCPAPEFE GGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLP SSIEKTISKAKGQPREPQVYTLPPSQEEMTKNQVSLTCLVKGFYPSD IAVEWESNGQPENNYKTTPPVLDSDGSFFLYSRLTVDKSRWQEGNVF SCSVMHEALHNHYTQKSLSLSLG |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

SEQUENCE LISTING

```
<160> NUMBER OF SEQ ID NOS: 75

<210> SEQ ID NO 1
<211> LENGTH: 31
<212> TYPE: PRT
<213> ORGANISM: Artificial Sequence
<220> FEATURE:
<223> OTHER INFORMATION: Peptide 4704
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys conjugated to COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 1

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Met Asp Thr Lys Lys
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Peptide 4739
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG2-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 2

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Met Asp Thr Lys Lys
            20                  25                  30

<210> SEQ ID NO 3
<211> LENGTH: 31
<212> TYPE: PRT
```

```
<213> ORGANISM: Artificial Sequence
<220> FEATURE:
<223> OTHER INFORMATION: Peptide 4740
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 3

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Met Asp Thr Lys Lys
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Peptide 5058
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG6-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 4

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Met Asp Thr Lys Lys
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Peptide 5059
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG8-COCH2ONH2
```

```
<220> FEATURE:
<221> NAME/KEY: MISC_FEATURE
<222> LOCATION: (31)..(31)
<223> OTHER INFORMATION: C-terminal amide

<400> SEQUENCE: 5

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Met Asp Thr Lys Lys
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Peptide 5615
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG24-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 6

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Met Asp Thr Lys Lys
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Peptide 6115
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG36-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 7

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Met Asp Thr Lys Lys
            20                  25                  30

<210> SEQ ID NO 8
```

-continued

```
<211> LENGTH: 31
<212> TYPE: PRT
<213> ORGANISM: Artificial Sequence
<220> FEATURE:
<223> OTHER INFORMATION: Peptide 5275
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 8

His Xaa Asp Gly Thr Phe Thr Ser Asp Tyr Ser Lys Tyr Leu Asp Xaa
  1               5                  10                  15

Arg Ala Ala Gln Asp Phe Val Gln Trp Leu Met Asp Thr Lys Lys
             20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Peptide 5048
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG2-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 9

His Xaa Gln Gly Thr Phe Thr Ser Asp Tyr Ser Lys Tyr Leu Asp Xaa
  1               5                  10                  15

Arg Ala Ala Gln Asp Phe Val Gln Trp Leu Met Asp Thr Lys Lys
             20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Peptide 5049
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
```

```
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 10

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Met Asp Thr Lys Lys
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Peptide 5050
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG6-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 11

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Met Asp Thr Lys Lys
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Peptide 5051
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG8-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 12

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Met Asp Thr Lys Lys
            20                  25                  30
```

<210> SEQ ID NO 13
<211> LENGTH: 31
<212> TYPE: PRT
<213> ORGANISM: Artificial Sequence
<220> FEATURE:
<223> OTHER INFORMATION: Peptide 6114
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG8-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 13

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Met Asp Thr Lys Lys
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Peptide 4840
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to COCH2ONH2

<400> SEQUENCE: 14

His Xaa Gln Gly Thr Phe Thr Ser Asp Tyr Ser Lys Tyr Leu Asp Xaa
1               5                   10                  15

Arg Ala Ala Gln Asp Phe Val Lys Trp Leu Met Asp Thr Lys Gln
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Peptide 4841
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG2-COCH2ONH2

-continued

```
<400> SEQUENCE: 15

His Xaa Gln Gly Thr Phe Thr Ser Asp Tyr Ser Lys Tyr Leu Asp Xaa
1               5                   10                  15

Arg Ala Ala Gln Asp Phe Val Lys Trp Leu Met Asp Thr Lys Gln
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Peptide 4842
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG4-COCH2ONH2

<400> SEQUENCE: 16

His Xaa Gln Gly Thr Phe Thr Ser Asp Tyr Ser Lys Tyr Leu Asp Xaa
1               5                   10                  15

Arg Ala Ala Gln Asp Phe Val Lys Trp Leu Met Asp Thr Lys Gln
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Peptide 5009
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG6-COCH2ONH2

<400> SEQUENCE: 17

His Xaa Gln Gly Thr Phe Thr Ser Asp Tyr Ser Lys Tyr Leu Asp Xaa
1               5                   10                  15

Arg Ala Ala Gln Asp Phe Val Lys Trp Leu Met Asp Thr Lys Gln
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: Peptide 5010
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
```

```
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG8-COCH2ONH2

<400> SEQUENCE: 18

His Xaa Gln Gly Thr Phe Thr Ser Asp Tyr Ser Lys Tyr Leu Asp Xaa
1               5                   10                  15

Arg Ala Ala Gln Asp Phe Val Lys Trp Leu Met Asp Thr Lys Gln
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: Peptide 5799
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (20)..(20)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG4-COCH2ONH2
<220> FEATURE:
<221> NAME/KEY: MISC_FEATURE
<222> LOCATION: (28)..(28)
<223> OTHER INFORMATION: Xaa is alpha-aminoisobutyric acid (Aib)

<400> SEQUENCE: 19

His Xaa Gln Gly Thr Phe Thr Ser Asp Tyr Ser Lys Tyr Leu Asp Xaa
1               5                   10                  15

Arg Ala Ala Xaa Asp Phe Val Lys Trp Leu Met Xaa Thr Lys Gln
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Peptide 5052
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG2-COCH2ONH2

<400> SEQUENCE: 20

His Xaa Gln Gly Thr Phe Thr Ser Asp Tyr Ser Lys Tyr Leu Asp Xaa
1               5                   10                  15

Arg Ala Ala Gln Asp Phe Val Lys Trp Leu Met Asp Thr Lys Gln
            20                  25                  30
```

```
<210> SEQ ID NO 21
<211> LENGTH: 31
<212> TYPE: PRT
<213> ORGANISM: artificial sequence
<220> FEATURE:
<223> OTHER INFORMATION: Peptide 5053
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG4-COCH2ONH2

<400> SEQUENCE: 21

His Xaa Gln Gly Thr Phe Thr Ser Asp Tyr Ser Lys Tyr Leu Asp Xaa
1               5                   10                  15

Arg Ala Ala Gln Asp Phe Val Lys Trp Leu Met Asp Thr Lys Gln
            20                  25                  30

<210> SEQ ID NO 22
<211> LENGTH: 29
<212> TYPE: PRT
<213> ORGANISM: Artificial Sequence
<220> FEATURE:
<223> OTHER INFORMATION: Peptide 5314
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG2-COCH2ONH2
<220> FEATURE:
<221> NAME/KEY: MISC_FEATURE
<222> LOCATION: (29)..(29)
<223> OTHER INFORMATION: C-terminal amide

<400> SEQUENCE: 22

His Xaa Gln Gly Thr Phe Thr Ser Asp Tyr Ser Lys Tyr Leu Asp Xaa
1               5                   10                  15

Arg Ala Ala Gln Asp Phe Val Lys Trp Leu Met Asp Thr
            20                  25

<210> SEQ ID NO 23
<211> LENGTH: 29
<212> TYPE: PRT
<213> ORGANISM: Artificial sequence
<220> FEATURE:
<223> OTHER INFORMATION: Peptide 5420
<220> FEATURE:
<221> NAME/KEY: MISC_FEATURE
<222> LOCATION: (2)..(2)
<223> OTHER INFORMATION: Xaa is D-Serine
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG4-COCH2ONH2
<220> FEATURE:
```

```
<221> NAME/KEY: MISC_FEATURE
<222> LOCATION: (29)..(29)
<223> OTHER INFORMATION: C-terminal amide

<400> SEQUENCE: 23

His Xaa Gln Gly Thr Phe Thr Ser Asp Tyr Ser Lys Tyr Leu Asp Xaa
1               5                   10                  15

Arg Ala Ala Gln Asp Phe Val Lys Trp Leu Met Asp Thr
            20                  25

<210> SEQ ID NO 24
<211> LENGTH: 31
<212> TYPE: PRT
<213> ORGANISM: Artificial sequence
<220> FEATURE:
<223> OTHER INFORMATION: Peptide 5798
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(28)
<223> OTHER INFORMATION: lactam bridge between E24 and K28
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 24

His Xaa Gln Gly Thr Phe Thr Ser Asp Tyr Ser Lys Tyr Leu Asp Xaa
1               5                   10                  15

Arg Ala Ala Gln Asp Phe Val Glu Trp Leu Met Lys Thr Lys Lys
            20                  25                  30

<210> SEQ ID NO 25
<211> LENGTH: 31
<212> TYPE: PRT
<213> ORGANISM: Artificial sequence
<220> FEATURE:
<223> OTHER INFORMATION: Peptide 5759
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is beta-(3-benzothienyl)-alanine (Bzt)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 25

His Xaa Gln Gly Thr Phe Thr Ser Asp Tyr Ser Lys Tyr Leu Asp Xaa
```

```
                1               5                  10                  15
Arg Ala Ala Gln Asp Phe Val Gln Xaa Leu Met Asp Thr Lys Lys
                20                  25                  30

<210> SEQ ID NO 26
<211> LENGTH: 31
<212> TYPE: PRT
<213> ORGANISM: Artificial sequence
<220> FEATURE:
<223> OTHER INFORMATION: Peptide 5760
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is 7 Azatryptophan (AzTrp)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 26

His Xaa Gln Gly Thr Phe Thr Ser Asp Tyr Ser Lys Tyr Leu Asp Xaa
1               5                  10                  15
Arg Ala Ala Gln Asp Phe Val Gln Xaa Leu Met Asp Thr Lys Lys
                20                  25                  30

<210> SEQ ID NO 27
<211> LENGTH: 31
<212> TYPE: PRT
<213> ORGANISM: Artificial sequence
<220> FEATURE:
<223> OTHER INFORMATION: Peptide 5761
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is 2-naphthylalanine (2Nap)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 27

His Xaa Gln Gly Thr Phe Thr Ser Asp Tyr Ser Lys Tyr Leu Asp Xaa
1               5                  10                  15
Arg Ala Ala Gln Asp Phe Val Gln Xaa Leu Met Asp Thr Lys Lys
                20                  25                  30

<210> SEQ ID NO 28
```

-continued

```
<211> LENGTH: 31
<212> TYPE: PRT
<213> ORGANISM: Artificial sequence
<220> FEATURE:
<223> OTHER INFORMATION: Peptide 5762
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is (3-Pyridyl)alanine (3Pyr)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 28

His Xaa Gln Gly Thr Phe Thr Ser Asp Tyr Ser Lys Tyr Leu Asp Xaa
1               5                   10                  15

Arg Ala Ala Gln Asp Phe Val Gln Xaa Leu Met Asp Thr Lys Lys
            20                  25                  30

<210> SEQ ID NO 29
<211> LENGTH: 31
<212> TYPE: PRT
<213> ORGANISM: Artificial sequence
<220> FEATURE:
<223> OTHER INFORMATION: Peptide 5763
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 29

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Met Asp Xaa Lys Lys
            20                  25                  30

<210> SEQ ID NO 30
<211> LENGTH: 31
<212> TYPE: PRT
<213> ORGANISM: Artificial sequence
<220> FEATURE:
<223> OTHER INFORMATION: peptide 5764
<220> FEATURE:
<221> NAME/KEY: MISC_FEATURE
```

```
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (27)..(27)
<223> OTHER INFORMATION: Xaa is methionine sulfoxide (M(O))
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 30

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Xaa Asp Thr Lys Lys
            20                  25                  30

<210> SEQ ID NO 31
<211> LENGTH: 31
<212> TYPE: PRT
<213> ORGANISM: Artificial sequence
<220> FEATURE:
<223> OTHER INFORMATION: Peptide 5765
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (27)..(27)
<223> OTHER INFORMATION: Xaa is homoleucine (hLeu)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 31

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Xaa Asp Thr Lys Lys
            20                  25                  30

<210> SEQ ID NO 32
<211> LENGTH: 31
<212> TYPE: PRT
<213> ORGANISM: Artificial sequence
<220> FEATURE:
<223> OTHER INFORMATION: Peptide 5766
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
```

```
<221> NAME/KEY: MISC_FEATURE
<222> LOCATION: (27)..(27)
<223> OTHER INFORMATION: Xaa is homocycloexylalanine (hCha)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 32

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Xaa Asp Thr Lys Lys
            20                  25                  30

<210> SEQ ID NO 33
<211> LENGTH: 31
<212> TYPE: PRT
<213> ORGANISM: Artificial sequence
<220> FEATURE:
<223> OTHER INFORMATION: Peptide 6052
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is 3-(2quinoyl)-alanine (3Qui)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 33

His Xaa Gln Gly Thr Phe Thr Ser Asp Tyr Ser Lys Tyr Leu Asp Xaa
1               5                   10                  15

Arg Ala Ala Gln Asp Phe Val Gln Xaa Leu Met Asp Thr Lys Lys
            20                  25                  30

<210> SEQ ID NO 34
<211> LENGTH: 31
<212> TYPE: PRT
<213> ORGANISM: Artificial sequence
<220> FEATURE:
<223> OTHER INFORMATION: peptide 6053
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is 4'-biphenylalanine (Bip)
<220> FEATURE:
<221> NAME/KEY: MISC_FEATURE
<222> LOCATION: (31)..(31)
<223> OTHER INFORMATION: Lys is conjugated to PEG4-COCH2ONH2
```

<220> FEATURE:
<221> NAME/KEY: MISC_FEATURE
<222> LOCATION: (31)..(31)
<223> OTHER INFORMATION: C-terminal amide

<400> SEQUENCE: 34

His Xaa Gln Gly Thr Phe Thr Ser Asp Tyr Ser Lys Tyr Leu Asp Xaa
1               5                   10                  15

Arg Ala Ala Gln Asp Phe Val Gln Xaa Leu Met Asp Thr Lys Lys
            20                  25                  30

<210> SEQ ID NO 35
<211> LENGTH: 31
<212> TYPE: PRT
<213> ORGANISM: Artificial sequence
<220> FEATURE:
<223> OTHER INFORMATION: Peptide 6062
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is N-methyl-tryptophane (Trp(Me))
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 35

His Xaa Gln Gly Thr Phe Thr Ser Asp Tyr Ser Lys Tyr Leu Asp Xaa
1               5                   10                  15

Arg Ala Ala Gln Asp Phe Val Gln Xaa Leu Met Asp Thr Lys Lys
            20                  25                  30

<210> SEQ ID NO 36
<211> LENGTH: 31
<212> TYPE: PRT
<213> ORGANISM: Artificial sequence
<220> FEATURE:
<223> OTHER INFORMATION: Peptide 6376
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (26)..(26)
<223> OTHER INFORMATION: Xaa is Trp(Me)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 36

His Xaa Gln Gly Thr Phe Thr Ser Asp Tyr Ser Lys Tyr Leu Asp Xaa
1               5                   10                  15

Arg Ala Ala Gln Asp Phe Val Gln Trp Xaa Met Asp Thr Lys Lys
            20                  25                  30

<210> SEQ ID NO 37
<211> LENGTH: 31
<212> TYPE: PRT
<213> ORGANISM: Artificial sequence
<220> FEATURE:
<223> OTHER INFORMATION: Peptide 6377
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is hexafluoroleucine (HFL)
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 37

His Xaa Gln Gly Thr Phe Thr Ser Asp Tyr Ser Lys Tyr Leu Asp Xaa
1               5                   10                  15

Arg Ala Ala Gln Asp Phe Val Gln Trp Xaa Met Asp Thr Lys Lys
            20                  25                  30

<210> SEQ ID NO 38
<211> LENGTH: 31
<212> TYPE: PRT
<213> ORGANISM: Artificial sequence
<220> FEATURE:
<223> OTHER INFORMATION: Peptide 6378
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is 5-hydroxy tryptophan (W(5OH))
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 38

His Xaa Gln Gly Thr Phe Thr Ser Asp Tyr Ser Lys Tyr Leu Asp Xaa
1               5                   10                  15

Arg Ala Ala Gln Asp Phe Val Gln Xaa Leu Met Asp Thr Lys Lys
            20                  25                  30

<210> SEQ ID NO 39
<211> LENGTH: 31
<212> TYPE: PRT
<213> ORGANISM: Artificial sequence
<220> FEATURE:
<223> OTHER INFORMATION: Peptide 6379
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 39

His Xaa Gln Gly Thr Phe Thr Ser Asp Tyr Ser Lys Tyr Leu Asp Xaa
1               5                   10                  15

Arg Ala Ala Gln Asp Phe Val Gln Lys Leu Met Asp Thr Lys Lys
            20                  25                  30

<210> SEQ ID NO 40
<211> LENGTH: 31
<212> TYPE: PRT
<213> ORGANISM: Artificial sequence
<220> FEATURE:
<223> OTHER INFORMATION: Peptide 6380
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 40

His Xaa Gln Gly Thr Phe Thr Ser Asp Tyr Ser Lys Tyr Leu Asp Xaa
1               5                   10                  15

Arg Ala Ala Gln Asp Phe Val Gln Gln Leu Met Asp Thr Lys Lys
            20                  25                  30

<210> SEQ ID NO 41
<211> LENGTH: 31
<212> TYPE: PRT
<213> ORGANISM: Artificial sequence
<220> FEATURE:
<223> OTHER INFORMATION: Peptide 6381
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:

```
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG4-COCH2ONH2

<400> SEQUENCE: 41

His Xaa Gln Gly Thr Phe Thr Ser Asp Tyr Ser Lys Tyr Leu Asp Xaa
1               5                   10                  15

Arg Ala Ala Gln Asp Phe Val Gln Asn Leu Met Asp Thr Lys Lys
            20                  25                  30

<210> SEQ ID NO 42
<211> LENGTH: 31
<212> TYPE: PRT
<213> ORGANISM: Artificial sequence
<220> FEATURE:
<223> OTHER INFORMATION: Peptide 6383
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is alpha-methylphenylalanine (aMePhe)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 42

His Xaa Gln Gly Thr Phe Thr Ser Asp Tyr Ser Lys Tyr Leu Asp Xaa
1               5                   10                  15

Arg Ala Ala Gln Asp Phe Val Gln Xaa Leu Met Asp Thr Lys Lys
            20                  25                  30

<210> SEQ ID NO 43
<211> LENGTH: 31
<212> TYPE: PRT
<213> ORGANISM: Artificial sequence
<220> FEATURE:
<223> OTHER INFORMATION: Peptide 6383
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide
```

<400> SEQUENCE: 43

His Xaa Gln Gly Thr Phe Thr Ser Asp Tyr Ser Lys Tyr Leu Asp Xaa
1               5                   10                  15

Arg Ala Ala Gln Asp Phe Val Gln Xaa Leu Met Asp Thr Lys Lys
            20                  25                  30

<210> SEQ ID NO 44
<211> LENGTH: 31
<212> TYPE: PRT
<213> ORGANISM: Artificial sequence
<220> FEATURE:
<223> OTHER INFORMATION: Peptide 6384
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is alpha-methyl-leucine (aMeLeu)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 44

His Xaa Gln Gly Thr Phe Thr Ser Asp Tyr Ser Lys Tyr Leu Asp Xaa
1               5                   10                  15

Arg Ala Ala Gln Asp Phe Val Gln Xaa Leu Met Asp Thr Lys Lys
            20                  25                  30

<210> SEQ ID NO 45
<211> LENGTH: 31
<212> TYPE: PRT
<213> ORGANISM: Artificial sequence
<220> FEATURE:
<223> OTHER INFORMATION: peptide 6385
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is alpha-methyltryptophan (aMeTrp)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 45

His Xaa Gln Gly Thr Phe Thr Ser Asp Tyr Ser Lys Tyr Leu Asp Xaa
1               5                   10                  15

Arg Ala Ala Gln Asp Phe Val Gln Xaa Leu Met Asp Thr Lys Lys

-continued

```
<210> SEQ ID NO 46
<211> LENGTH: 31
<212> TYPE: PRT
<213> ORGANISM: Artificial sequence
<220> FEATURE:
<223> OTHER INFORMATION: Peptide 6386
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (25)..(25)
<223> OTHER INFORMATION: Xaa is beta homo tryptophan (bhoTrp)
<220> FEATURE:
<221> NAME/KEY: MISC_FEATURE
<222> LOCATION: (31)..(31)
<223> OTHER INFORMATION: Lys is conjugated to PEG4-COCH2ONH2

<400> SEQUENCE: 46

His Xaa Gln Gly Thr Phe Thr Ser Asp Tyr Ser Lys Tyr Leu Asp Xaa
  1               5                  10                  15

Arg Ala Ala Gln Asp Phe Val Gln Xaa Leu Met Asp Thr Lys Lys
              20                  25                  30

<210> SEQ ID NO 47
<211> LENGTH: 31
<212> TYPE: PRT
<213> ORGANISM: Artificial sequence
<220> FEATURE:
<223> OTHER INFORMATION: Peptide 4699
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (10)..(10)
<223> OTHER INFORMATION: Lys conjugated to COCH2ONH2
<220> FEATURE:
<221> NAME/KEY: MISC_FEATURE
<222> LOCATION: (16)..(16)
<223> OTHER INFORMATION: Xaa is alpha-aminoisobutyric acid (Aib)

<400> SEQUENCE: 47

His Xaa Gln Gly Thr Phe Thr Ser Asp Lys Ser Lys Tyr Leu Asp Xaa
  1               5                  10                  15

Arg Ala Ala Gln Asp Phe Val Gln Trp Leu Met Asp Thr Lys Gln
              20                  25                  30

<210> SEQ ID NO 48
<211> LENGTH: 31
<212> TYPE: PRT
<213> ORGANISM: Artificial sequence
<220> FEATURE:
<223> OTHER INFORMATION: Peptide 4700
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
```

<222> LOCATION: (31)..(31)
<223> OTHER INFORMATION: Lys is conjugated to gammaE-COCH2ONH2

<400> SEQUENCE: 48

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr Lys Gln
            20                  25                  30

<210> SEQ ID NO 49
<211> LENGTH: 31
<212> TYPE: PRT
<213> ORGANISM: Artificial sequence
<220> FEATURE:
<223> OTHER INFORMATION: Peptide 4701
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (10)..(10)
<223> OTHER INFORMATION: Lys is conjugated to gammaE-gammaE-COCH2ONH2
<220> FEATURE:
<221> NAME/KEY: MISC_FEATURE
<222> LOCATION: (16)..(16)
<223> OTHER INFORMATION: Xaa is alpha-aminoisobutyric acid (Aib)

<400> SEQUENCE: 49

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr Lys Gln
            20                  25                  30

<210> SEQ ID NO 50
<211> LENGTH: 31
<212> TYPE: PRT
<213> ORGANISM: Artificial sequence
<220> FEATURE:
<223> OTHER INFORMATION: Peptide 4702
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (10)..(10)
<223> OTHER INFORMATION: Lys is conjugated to PEG2-COCH2ONH2
<220> FEATURE:
<221> NAME/KEY: MISC_FEATURE
<222> LOCATION: (16)..(16)
<223> OTHER INFORMATION: Xaa is alpha-aminoisobutyric acid (Aib)

<400> SEQUENCE: 50

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr Lys Gln
            20                  25                  30

<210> SEQ ID NO 51
<211> LENGTH: 31
<212> TYPE: PRT
<213> ORGANISM: Artificial sequence
<220> FEATURE:
<223> OTHER INFORMATION: Peptide 4703
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:

```
<221> NAME/KEY: MISC_FEATURE
<222> LOCATION: (10)..(10)
<223> OTHER INFORMATION: Lys is conjugated to PEG4-COCH2ONH2
<220> FEATURE:
<221> NAME/KEY: MISC_FEATURE
<222> LOCATION: (16)..(16)
<223> OTHER INFORMATION: Xaa is alpha-aminoisobutyric acid (Aib)

<400> SEQUENCE: 51

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr Lys Gln
            20                  25                  30

<210> SEQ ID NO 52
<211> LENGTH: 30
<212> TYPE: PRT
<213> ORGANISM: Artificial sequence
<220> FEATURE:
<223> OTHER INFORMATION: Pepetide 4896
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (10)..(10)
<223> OTHER INFORMATION: Lys is conjugated to gammaE-gammaE-palmitoyl
      (C15-CO-)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to COCH2ONH2

<400> SEQUENCE: 52

His Xaa Gln Gly Thr Phe Thr Ser Asp Lys Ser Lys Tyr Leu Asp Xaa
1               5                   10                  15

Arg Ala Ala Gln Asp Phe Val Lys Leu Met Asp Thr Lys Gln
            20                  25                  30

<210> SEQ ID NO 53
<211> LENGTH: 31
<212> TYPE: PRT
<213> ORGANISM: Artificial sequence
<220> FEATURE:
<223> OTHER INFORMATION: Peptide 4952
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (10)..(10)
<223> OTHER INFORMATION: Lys is conjugated to gammaE-gammaE-palmitoyl
      (C15-CO-)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG2-COCH2ONH2

<400> SEQUENCE: 53

His Xaa Gln Gly Thr Phe Thr Ser Asp Lys Ser Lys Tyr Leu Asp Xaa
1               5                   10                  15
```

Arg Ala Ala Gln Asp Phe Val Lys Trp Leu Met Asp Thr Lys Gln
            20                  25                  30

<210> SEQ ID NO 54
<211> LENGTH: 31
<212> TYPE: PRT
<213> ORGANISM: Artificial sequence
<220> FEATURE:
<223> OTHER INFORMATION: Peptide 4953
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (10)..(10)
<223> OTHER INFORMATION: Lys is conjugated to gammaE-gammaE-palmitoyl
      (C15-CO-)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG4-COCH2ONH2

<400> SEQUENCE: 54

His Xaa Gln Gly Thr Phe Thr Ser Asp Lys Ser Lys Tyr Leu Asp Xaa
1               5                   10                  15

Arg Ala Ala Gln Asp Phe Val Lys Trp Leu Met Asp Thr Lys Gln
            20                  25                  30

<210> SEQ ID NO 55
<211> LENGTH: 31
<212> TYPE: PRT
<213> ORGANISM: Artificial sequence
<220> FEATURE:
<223> OTHER INFORMATION: Peptide 5866
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 55

His Ser Gln Gly Thr Phe Thr Ser Asp Tyr Ser Lys Tyr Leu Asp Ser
1               5                   10                  15

Arg Ala Ala Gln Asp Phe Val Gln Trp Leu Met Asp Thr Lys Lys
            20                  25                  30

<210> SEQ ID NO 56
<211> LENGTH: 31
<212> TYPE: PRT
<213> ORGANISM: Artificial sequence
<220> FEATURE:
<223> OTHER INFORMATION: Peptide 6541
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Xaa is alpha-aminoisobutyric acid (Aib)

```
<220> FEATURE:
<221> NAME/KEY: MISC_FEATURE
<222> LOCATION: (28)..(28)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 56

His Xaa Gln Gly Thr Phe Thr Ser Asp Tyr Ser Lys Tyr Leu Asp Xaa
1               5                   10                  15

Arg Ala Ala Gln Asp Phe Val Xaa Trp Leu Met Xaa Thr Lys Lys
            20                  25                  30

<210> SEQ ID NO 57
<211> LENGTH: 31
<212> TYPE: PRT
<213> ORGANISM: Artificial sequence
<220> FEATURE:
<223> OTHER INFORMATION: Peptide 6542
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (12)..(12)
<223> OTHER INFORMATION: Xaa is is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Xaa is alpha-aminoisobutyric acid (Aib)
<220> FEATURE:
<221> NAME/KEY: MISC_FEATURE
<222> LOCATION: (28)..(28)
<223> OTHER INFORMATION: Xaa is is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 57

His Xaa Gln Gly Thr Phe Thr Ser Asp Tyr Ser Xaa Tyr Leu Asp Xaa
1               5                   10                  15

Arg Ala Ala Gln Asp Phe Val Xaa Trp Leu Met Xaa Thr Lys Lys
            20                  25                  30

<210> SEQ ID NO 58
<211> LENGTH: 31
<212> TYPE: PRT
<213> ORGANISM: Artificial sequence
<220> FEATURE:
<223> OTHER INFORMATION: Peptide 6543
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (16)..(16)
```

```
<223> OTHER INFORMATION: Xaa is alpha-aminoisobutyric acid (Aib)
<220> FEATURE:
<221> NAME/KEY: MISC_FEATURE
<222> LOCATION: (20)..(20)
<223> OTHER INFORMATION: Xaa is alpha-aminoisobutyric acid (Aib)
<220> FEATURE:
<221> NAME/KEY: MISC_FEATURE
<222> LOCATION: (28)..(28)
<223> OTHER INFORMATION: Xaa is is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG4-COCH2ONH2
<220> FEATURE:
<221> NAME/KEY: MISC_FEATURE
<222> LOCATION: (31)..(31)
<223> OTHER INFORMATION: C-terminal amide

<400> SEQUENCE: 58

His Xaa Gln Gly Thr Phe Thr Ser Asp Tyr Ser Lys Tyr Leu Asp Xaa
1               5                   10                  15

Arg Ala Ala Xaa Asp Phe Val Gln Trp Leu Met Xaa Thr Lys Lys
            20                  25                  30

<210> SEQ ID NO 59
<211> LENGTH: 31
<212> TYPE: PRT
<213> ORGANISM: Artificial sequence
<220> FEATURE:
<223> OTHER INFORMATION: Peptide 6544
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (12)..(12)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (20)..(20)
<223> OTHER INFORMATION: Xaa is alpha-aminoisobutyric acid (Aib)
<220> FEATURE:
<221> NAME/KEY: MISC_FEATURE
<222> LOCATION: (28)..(28)
<223> OTHER INFORMATION: Xaa is alpha-aminoisobutyric acid (Aib)
<220> FEATURE:
<221> NAME/KEY: MISC_FEATURE
<222> LOCATION: (31)..(31)
<223> OTHER INFORMATION: Lys is conjugated to PEG4-COCH2ONH2

<400> SEQUENCE: 59

His Xaa Gln Gly Thr Phe Thr Ser Asp Tyr Ser Xaa Tyr Leu Asp Xaa
1               5                   10                  15

Arg Ala Ala Xaa Asp Phe Val Gln Trp Leu Met Xaa Thr Lys Lys
            20                  25                  30

<210> SEQ ID NO 60
<211> LENGTH: 31
<212> TYPE: PRT
<213> ORGANISM: Artificial sequence
<220> FEATURE:
<223> OTHER INFORMATION: Peptide 6545
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
```

```
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (20)..(20)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG24-COCH2ONH2
<220> FEATURE:
<221> NAME/KEY: MISC_FEATURE
<222> LOCATION: (28)..(28)
<223> OTHER INFORMATION: Xaa is alpha-aminoisobutyric acid (Aib)

<400> SEQUENCE: 60

His Xaa Gln Gly Thr Phe Thr Ser Asp Tyr Ser Lys Tyr Leu Asp Xaa
 1               5                  10                  15

Arg Ala Ala Xaa Asp Phe Val Lys Trp Leu Met Xaa Thr Lys Gln
            20                  25                  30

<210> SEQ ID NO 61
<211> LENGTH: 31
<212> TYPE: PRT
<213> ORGANISM: Artificial sequence
<220> FEATURE:
<223> OTHER INFORMATION: Peptide 6546
<220> FEATURE:
<221> NAME/KEY: MISC_FEATURE
<222> LOCATION: (2)..(2)
<223> OTHER INFORMATION: Xaa is alpha-aminoisobutyric acid (Aib)
<220> FEATURE:
<221> NAME/KEY: MISC_FEATURE
<222> LOCATION: (12)..(12)
<223> OTHER INFORMATION: Xaa is alpha-aminoisobutyric acid (Aib)
<220> FEATURE:
<221> NAME/KEY: MISC_FEATURE
<222> LOCATION: (16)..(16)
<223> OTHER INFORMATION: Xaa is alpha-aminoisobutyric acid (Aib)
<220> FEATURE:
<221> NAME/KEY: MISC_FEATURE
<222> LOCATION: (20)..(20)
<223> OTHER INFORMATION: Xaa is alpha-aminoisobutyric acid (Aib)
<220> FEATURE:
<221> NAME/KEY: MISC_FEATURE
<222> LOCATION: (24)..(24)
<223> OTHER INFORMATION: Lys is conjugated to PEG24-COCH2ONH2
<220> FEATURE:
<221> NAME/KEY: MISC_FEATURE
<222> LOCATION: (28)..(28)
<223> OTHER INFORMATION: Xaa is alpha-aminoisobutyric acid (Aib)

<400> SEQUENCE: 61

His Xaa Gln Gly Thr Phe Thr Ser Asp Tyr Ser Xaa Tyr Leu Asp Xaa
 1               5                  10                  15

Arg Ala Ala Xaa Asp Phe Val Lys Trp Leu Met Xaa Thr Lys Gln
            20                  25                  30

<210> SEQ ID NO 62
<211> LENGTH: 31
<212> TYPE: PRT
<213> ORGANISM: Artificial sequence
<220> FEATURE:
<223> OTHER INFORMATION: GCCR-GLP1R Co-agonist
<220> FEATURE:
<221> NAME/KEY: MISC_FEATURE
<222> LOCATION: (1)..(31)
<223> OTHER INFORMATION: For any peptide only one of Xaa10, Xaa24, or
      Xaa31 can be Lys
<220> FEATURE:
<221> NAME/KEY: MISC_FEATURE
<222> LOCATION: (2)..(2)
<223> OTHER INFORMATION: Xaa is alpha-aminoisobutyric acid (aib) or
```

```
                            D-Ser
<220> FEATURE:
<221> NAME/KEY: MISC_FEATURE
<222> LOCATION: (10)..(10)
<223> OTHER INFORMATION: Xaa is Tyr when Xaa31 is Lys, or Lys if neither
      Xaa24 or Xaa31 is Lys, or Tyr or Lys if Xaa24 is Lys
<220> FEATURE:
<221> NAME/KEY: MISC_FEATURE
<222> LOCATION: (16)..(16)
<223> OTHER INFORMATION: Xaa is aib
<220> FEATURE:
<221> NAME/KEY: MISC_FEATURE
<222> LOCATION: (24)..(24)
<223> OTHER INFORMATION: Xaa is Gln when Xaa10 is Lys, or Gln or aib
      when Xaa31 is Lys, or Lys when Xaa10 and Xaa31 are Tyr and Gln,
      respectively, or Glu when Xaa28 is Lys,
<220> FEATURE:
<221> NAME/KEY: MISC_FEATURE
<222> LOCATION: (31)..(31)
<223> OTHER INFORMATION: Xaa31 is Lys or Gln when Xaa10 or Xaa24 is Lys

<400> SEQUENCE: 62

His Xaa Gln Gly Thr Phe Thr Ser Asp Xaa Ser Lys Tyr Leu Asp Xaa
1               5                   10                  15

Arg Ala Ala Gln Asp Phe Val Xaa Trp Leu Met Asp Thr Lys Gln
            20                  25                  30

<210> SEQ ID NO 63
<211> LENGTH: 31
<212> TYPE: PRT
<213> ORGANISM: Artificial sequence
<220> FEATURE:
<223> OTHER INFORMATION: GCCR-GLP1 Co-Agonist
<220> FEATURE:
<221> NAME/KEY: MISC_FEATURE
<222> LOCATION: (1)..(31)
<223> OTHER INFORMATION: one of Lys10, Lys24, or Lys31 is covalently
      linked at its epsilon amino group to an aminooxy acid residue
<220> FEATURE:
<221> NAME/KEY: MISC_FEATURE
<222> LOCATION: (1)..(31)
<223> OTHER INFORMATION: optionally, Lys10 may be conjugated at its
      epsilon amino group to palmitic acid if Lys24 is conjugated at its
      epsilon amino group to aminooxy acid (HOCOCH2ONH2)
<220> FEATURE:
<221> NAME/KEY: MISC_FEATURE
<222> LOCATION: (2)..(2)
<223> OTHER INFORMATION: Xaa2 is alpha-aminoisobutyric acid (aib) or
      D-Ser;
<220> FEATURE:
<221> NAME/KEY: MISC_FEATURE
<222> LOCATION: (10)..(10)
<223> OTHER INFORMATION: Xaa10 is Tyr when Xaa31 is Lys, or Lys if
      neither Xaa24 or Xaa31 is Lys, or Tyr or Lys if Xaa24 is Lys;
      optionally, Lys10 may be covalently linked at its epsilon amino
      group to a fatty acid if Lys24 is covalently linked to aminooxy
      acid residue
<220> FEATURE:
<221> NAME/KEY: MISC_FEATURE
<222> LOCATION: (12)..(12)
<223> OTHER INFORMATION: Xaa12 is Lys or aib when Xaa31 is Lys, with the
      proviso that when Xaa12 is aib, then either Xaa20 or Xaa24 is aib
      and Xaa10, Xaa25, Xaa26, Xaa25, Xaa27, Xaa28, and Xaa29 are Tyr,
      Trp, Leu, Met, Asp, and Thr, respectively;
<220> FEATURE:
<221> NAME/KEY: MISC_FEATURE
<222> LOCATION: (16)..(16)
<223> OTHER INFORMATION: Xaa2 is alpha-aminoisobutyric acid (aib)
<220> FEATURE:
<221> NAME/KEY: MISC_FEATURE
<222> LOCATION: (20)..(20)
<223> OTHER INFORMATION: Xaa20 is Gln or aib when Xaa24 or Xaa31 is Lys
      with the proviso that when Xaa20 is aib then Xaa10, Xaa24, Xaa25,
      Xaa26, Xaa25, Xaa27, Xaa28, and Xaa29 are Tyr, Gln, Trp, Leu, Met,
      Asp, and Thr, respectively
<220> FEATURE:
```

```
<221> NAME/KEY: MISC_FEATURE
<222> LOCATION: (24)..(24)
<223> OTHER INFORMATION: Xaa24 is Q when Xaa10 is K, or Q or aib when
      Xaa31 is K, or K when Xaa10 and Xaa31 are Y and Q, respectively,
      or E when Xaa28 is K; proviso when Xaa24 is aib then Xaa10, Xaa25,
      Xaa26, Xaa27, Xaa28, an Xaa29 are Y, W, L, M, D, and T,
      respectively
<220> FEATURE:
<221> NAME/KEY: MISC_FEATURE
<222> LOCATION: (25)..(25)
<223> OTHER INFORMATION: Xaa25 is W, Q, D, K, aib, aMePhe, aMeLeu,
      aMeTrp, bhoTrp, 5W(5OH), Bzt, AzTrp, 2Nap, 3Pyr, 3Qui, BIP, or
      NTrp(Me)
<220> FEATURE:
<221> NAME/KEY: MISC_FEATURE
<222> LOCATION: (25)..(25)
<223> OTHER INFORMATION: with the proviso that when Xaa25 is  Q, D, K,
      aib, aMePhe, aMeLeu, aMeTrp, bhoTrp, W(5OH), Bzt, AzTrp, 2Nap,
      3Pyr, 3Qui, BIP, or Trp(Me), then Xaa12, Xaa20, Xaa24, Xaa26, and
      Xaa27 are K, Q, Q, L, and M, respectively, and Xaa31 is K
<220> FEATURE:
<221> NAME/KEY: MISC_FEATURE
<222> LOCATION: (26)..(26)
<223> OTHER INFORMATION: Xaa26 is Leu, aib, or hexafluoroleucine (HFL)
      with the proviso that when Xaa26 is aib or HFL, then Xaa31 is Lys
      and Xaa12, Xaa20, Xaa24, Xaa25, and Xaa27 are Lys, Gln, Gln, Trp,
      and Met, respectively
<220> FEATURE:
<221> NAME/KEY: MISC_FEATURE
<222> LOCATION: (27)..(27)
<223> OTHER INFORMATION: Xaa27 is Met, M(O), hLeu, or hCha with the
      proviso that when Xaa27 is  methionine sulfoxide (M(O)),
      homoleucine (hLeu), or homocycloexylaline (hCha), then Xaa31 is
      Lys and Xaa12, Xaa20, Xaa24, Xaa25, Xaa26, Xaa28, Xaa29 are Lys,
      Gln, Gln, Trp, Leu,
<220> FEATURE:
<221> NAME/KEY: MISC_FEATURE
<222> LOCATION: (28)..(28)
<223> OTHER INFORMATION: Xaa28 is Asp or aib, or Lys when Xaa24 is Glu,
      with the proviso that when Xaa28 includes aib then Xaa24 is Lys
      and Xaa10, Xaa12, Xaa25, Xaa26, Xaa27, Xaa29 are Tyr, Lys, Trp,
      Leu, Met, and Thr, respectively
<220> FEATURE:
<221> NAME/KEY: MISC_FEATURE
<222> LOCATION: (29)..(29)
<223> OTHER INFORMATION: Xaa29 is Thr or aib with the proviso that when
      Xaa29 is aib then Xaa31 is Lys and Xaa10, Xaa12, Xaa25, Xaa26,
      Xaa27, Xaa28 are Tyr, Lys, Trp, Leu, Met, Asp, and Thr,
      respectively
<220> FEATURE:
<221> NAME/KEY: MISC_FEATURE
<222> LOCATION: (31)..(31)
<223> OTHER INFORMATION: Xaa31 is Lys or Gln when Xaa10 or Xaa24 is Lys
      with the proviso that for any peptide only one of Xaa10, Xaa24, or
      Xaa31 can be Lys

<400> SEQUENCE: 63

His Xaa Gln Gly Thr Phe Thr Ser Asp Xaa Ser Xaa Tyr Leu Asp Xaa
1               5                   10                  15

Arg Ala Ala Xaa Asp Phe Val Xaa Xaa Xaa Xaa Xaa Xaa Lys Xaa
            20                  25                  30

<210> SEQ ID NO 64
<211> LENGTH: 213
<212> TYPE: PRT
<213> ORGANISM: Artificial sequence
<220> FEATURE:
<223> OTHER INFORMATION: Palivizumab Light Chain

<400> SEQUENCE: 64

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30
```

-continued

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
     50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 65
<211> LENGTH: 446
<212> TYPE: PRT
<213> ORGANISM: Artificial sequence
<220> FEATURE:
<223> OTHER INFORMATION: Antibody heavy chain

<400> SEQUENCE: 65

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 66
<211> LENGTH: 446
<212> TYPE: PRT
<213> ORGANISM: Artificial sequence
<220> FEATURE:
<223> OTHER INFORMATION: Ambody heavy chain HS32
<220> FEATURE:
<221> NAME/KEY: MISC_FEATURE
<222> LOCATION: (32)..(32)
<223> OTHER INFORMATION: Xaa is pAcF

<400> SEQUENCE: 66

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Xaa
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val

```
                65                  70                  75                  80
Val Leu Lys Val Thr Asn Met Asp Pro Ala Asp Thr Ala Thr Tyr Tyr
                    85                  90                  95

Cys Ala Arg Ser Met Ile Thr Asn Trp Tyr Phe Asp Val Trp Gly Ala
                    100                 105                 110

Gly Thr Thr Val Thr Val Ser Ala Ser Thr Lys Gly Pro Ser Val
                    115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                    180                 185                 190

Ser Ser Ser Leu Gly Thr Lys Thr Tyr Thr Cys Asn Val Asp His Lys
                    195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                    245                 250                 255

Pro Glu Val Thr Cys Val Val Val Asp Val Ser Gln Glu Asp Pro Glu
                    260                 265                 270

Val Gln Phe Asn Trp Tyr Val Asp Gly Val Glu Val His Asn Ala Lys
                    275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                    325                 330                 335

Ser Lys Ala Lys Gly Gln Pro Arg Glu Pro Gln Val Tyr Thr Leu Pro
                    340                 345                 350

Pro Ser Gln Glu Glu Met Thr Lys Asn Gln Val Ser Leu Thr Cys Leu
                    355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                    405                 410                 415

Trp Gln Glu Gly Asn Val Phe Ser Cys Ser Val Met His Glu Ala Leu
                    420                 425                 430

His Asn His Tyr Thr Gln Lys Ser Leu Ser Leu Ser Leu Gly
            435                 440                 445

<210> SEQ ID NO 67
<211> LENGTH: 446
<212> TYPE: PRT
<213> ORGANISM: Artificial sequence
<220> FEATURE:
<223> OTHER INFORMATION: Ambody heavy chain HQ16
<220> FEATURE:
```

<221> NAME/KEY: MISC_FEATURE
<222> LOCATION: (16)..(16)
<223> OTHER INFORMATION: Xaa is pAcF

<400> SEQUENCE: 67

```
Gln Val Thr Leu Arg Glu Ser Gly Pro Ala Leu Val Lys Pro Thr Xaa
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

-continued

```
                385                 390                 395                 400
Asp Gly Ser Phe Phe Leu Tyr Ser Arg Leu Thr Val Asp Lys Ser Arg
                    405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly
                435                 440                 445

<210> SEQ ID NO 68
<211> LENGTH: 446
<212> TYPE: PRT
<213> ORGANISM: Artificial sequence
<220> FEATURE:
<223> OTHER INFORMATION: ambody heavy chain HG33
<220> FEATURE:
<221> NAME/KEY: MISC_FEATURE
<222> LOCATION: (33)..(33)
<223> OTHER INFORMATION: Xaa is pAcF

<400> SEQUENCE: 68

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Xaa Met Ser Val Gly Trp Ile Arg Gln Pro Pro Gly Lys Ala Leu Glu
                35                  40                  45

Trp Leu Ala Asp Ile Trp Trp Asp Asp Lys Lys Asp Tyr Asn Pro Ser
        50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
                100                 105                 110

Gly Thr Thr Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285
```

-continued

```
Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 69
<211> LENGTH: 446
<212> TYPE: PRT
<213> ORGANISM: Artificial sequence
<220> FEATURE:
<223> OTHER INFORMATION: Ambody heavy chain HD56
<220> FEATURE:
<221> NAME/KEY: MISC_FEATURE
<222> LOCATION: (56)..(56)
<223> OTHER INFORMATION: Xaa is pAcF

<400> SEQUENCE: 69

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Xaa Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

```
<210> SEQ ID NO 70
<211> LENGTH: 446
<212> TYPE: PRT
<213> ORGANISM: Artificial sequence
<220> FEATURE:
<223> OTHER INFORMATION: Ambody heavy chain HT114
<220> FEATURE:
<221> NAME/KEY: MISC_FEATURE
<222> LOCATION: (114)..(114)
<223> OTHER INFORMATION: Xaa is pAcF

<400> SEQUENCE: 70
```

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr

```
                    85                  90                  95

Cys Ala Arg Ser Met Ile Thr Asn Trp Tyr Phe Asp Val Trp Gly Ala
            100                 105                 110

Gly Xaa Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 71
<211> LENGTH: 213
<212> TYPE: PRT
<213> ORGANISM: Artificial sequence
<220> FEATURE:
<223> OTHER INFORMATION: Ambody light chain LK125
<220> FEATURE:
<221> NAME/KEY: MISC_FEATURE
<222> LOCATION: (125)..(125)
<223> OTHER INFORMATION: Xaa is pAcF
```

<400> SEQUENCE: 71

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Xaa Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 72
<211> LENGTH: 213
<212> TYPE: PRT
<213> ORGANISM: Artificial sequence
<220> FEATURE:
<223> OTHER INFORMATION: Ambody light chain LE142
<220> FEATURE:
<221> NAME/KEY: MISC_FEATURE
<222> LOCATION: (142)..(142)
<223> OTHER INFORMATION: Xaa is pAcF

<400> SEQUENCE: 72

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Xaa Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 73
<211> LENGTH: 446
<212> TYPE: PRT
<213> ORGANISM: Artificial sequence
<220> FEATURE:
<223> OTHER INFORMATION: Ambody heavy chain HS179
<220> FEATURE:
<221> NAME/KEY: MISC_FEATURE
<222> LOCATION: (179)..(179)
<223> OTHER INFORMATION: Xaa is pAcF

<400> SEQUENCE: 73

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Xaa Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val

-continued

```
            225                 230                 235                 240
        Phe Leu Phe Pro Pro Lys Pro Lys Asp Thr Leu Met Ile Ser Arg Thr
                        245                 250                 255

Pro Glu Val Thr Cys Val Val Asp Val Ser Gln Glu Asp Pro Glu
                        260                 265                 270

Val Gln Phe Asn Trp Tyr Val Asp Gly Val Glu Val His Asn Ala Lys
                        275                 280                 285

Thr Lys Pro Arg Glu Glu Gln Phe Asn Ser Thr Tyr Arg Val Val Ser
                290                 295                 300

Val Leu Thr Val Leu His Gln Asp Trp Leu Asn Gly Lys Glu Tyr Lys
        305                 310                 315                 320

Cys Lys Val Ser Asn Lys Gly Leu Pro Ser Ser Ile Glu Lys Thr Ile
                        325                 330                 335

Ser Lys Ala Lys Gly Gln Pro Arg Glu Pro Gln Val Tyr Thr Leu Pro
                        340                 345                 350

Pro Ser Gln Glu Glu Met Thr Lys Asn Gln Val Ser Leu Thr Cys Leu
                        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Arg Leu Thr Val Asp Lys Ser Arg
                        405                 410                 415

Trp Gln Glu Gly Asn Val Phe Ser Cys Ser Val Met His Glu Ala Leu
                        420                 425                 430

His Asn His Tyr Thr Gln Lys Ser Leu Ser Leu Ser Leu Gly
                        435                 440                 445

<210> SEQ ID NO 74
<211> LENGTH: 446
<212> TYPE: PRT
<213> ORGANISM: Artificial sequence
<220> FEATURE:
<223> OTHER INFORMATION: Ambody heavy chain HT198
<220> FEATURE:
<221> NAME/KEY: MISC_FEATURE
<222> LOCATION: (198)..(198)
<223> OTHER INFORMATION: Xaa is pAcF

<400> SEQUENCE: 74

Gln Val Thr Leu Arg Glu Ser Gly Pro Ala Leu Val Lys Pro Thr Gln
        1               5                   10                  15

Thr Leu Thr Leu Thr Cys Thr Phe Ser Gly Phe Ser Leu Ser Thr Ser
                        20                  25                  30

Gly Met Ser Val Gly Trp Ile Arg Gln Pro Pro Gly Lys Ala Leu Glu
                    35                  40                  45

Trp Leu Ala Asp Ile Trp Trp Asp Asp Lys Lys Asp Tyr Asn Pro Ser
            50                  55                  60

Leu Lys Ser Arg Leu Thr Ile Ser Lys Asp Thr Ser Lys Asn Gln Val
        65                  70                  75                  80

Val Leu Lys Val Thr Asn Met Asp Pro Ala Asp Thr Ala Thr Tyr Tyr
                        85                  90                  95

Cys Ala Arg Ser Met Ile Thr Asn Trp Tyr Phe Asp Val Trp Gly Ala
                    100                 105                 110

Gly Thr Thr Val Thr Val Ser Ser Ala Ser Thr Lys Gly Pro Ser Val
                    115                 120                 125
```

```
Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Xaa Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 75
<211> LENGTH: 446
<212> TYPE: PRT
<213> ORGANISM: Artificial sequence
<220> FEATURE:
<223> OTHER INFORMATION: Ambody heavy chain HN211
<220> FEATURE:
<221> NAME/KEY: MISC_FEATURE
<222> LOCATION: (211)..(211)
<223> OTHER INFORMATION: Xaa is pAcF

<400> SEQUENCE: 75

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30
```

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Xaa Thr Lys Val Asp Lys Arg Val Glu Ser Lys Tyr Gly Pro
            210                 215                 220

Pro Cys Pro Pro Cys Pro Ala Pro Glu Phe Glu Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
            435                 440                 445

What is claimed:

1. An antibody peptide conjugate comprising:

an antibody having a light chain having the amino acid sequence of SEQ ID NO:64 and a heavy chain having the amino acid sequence of SEQ ID NO:65 conjugated to a peptide having the amino acid sequence (SEQ ID NO: 62)
His-Xaa²-Gln-Gly-Thr-Phe-Thr-Ser-Asp-Tyr-Ser-Lys- Tyr-Leu-Asp-Xaa¹⁶-Arg-Ala-Ala-Gln-Asp-Phe-Val-Gln- Trp-Leu-Met-Asp-Thr-Lys-Gln wherein Xaa² is α-aminoisobutyric acid (aib) or D-Ser; Xaa¹⁶ is aib; at least one of the amino acids at position 10, 24, or 31 is substituted with a Lys or the amino acids at positions 10 and 24 are each substituted with a Lys; and optionally the peptide comprises up to three additional amino acid substitutions;

wherein the heavy chain includes a substitution of the amino acid at position 16, 32, 33, 56, 114, 179, 198, or 211 with a para-acetylphenylalanine (pAcF) or the light chain includes a substitution of the amino acid at position 125 or 142 with pAcF;

wherein the peptide comprises either (i) an aminooxy acid residue covalently linked to the epsilon amino group of the Lys at position 10, 24, or 31 or (ii) an aminooxy acid residue covalently linked to the epsilon amino group of the Lys at position 10, 24, or 31 via a polyethylene glycol (PEG) spacer, a γGlu spacer, or a γGlu-γGlu spacer;

wherein the pAcF residue is covalently linked to the aminooxy acid residue; and wherein the antibody peptide conjugate is an agonist of the glucagon receptor and the glucagon-like peptide 1 receptor.

2. The antibody peptide conjugate of claim 1, wherein the peptide comprises a fatty acid covalently linked to the epsilon amino group of the Lys at position 10 via a γGlu-γGlu spacer.

3. The antibody peptide conjugate of claim 2, wherein the fatty acid comprises a C14, C15, C16, C17, C18, C19, or C20 fatty acid.

4. The antibody peptide conjugate of claim 3, wherein the fatty acid comprises the C14 fatty acid.

5. The antibody peptide conjugate of claim 1, comprising the polyethylene glycol spacer that comprises 2, 4, 6, 8, 24, or 36 ethoxy units.

6. The antibody peptide conjugate of claim 1 wherein:
the antibody has a light chain having the amino acid sequence of SEQ ID NO:64, SEQ ID NO:71, or SEQ ID NO:72 and a heavy chain having the amino acid sequence of SEQ ID NO:65, SEQ ID NO:66, SEQ ID NO:67, SEQ ID NO:68, SEQ ID NO:69, SEQ ID NO:70, SEQ ID NO:73, SEQ ID NO:74, or SEQ ID NO:75 conjugated to a peptide comprising the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:43, SEQ ID NO:44, SEQ ID NO:45, SEQ ID NO:46, SEQ ID NO:47, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, or SEQ ID NO:61, wherein the aminooxy acid residue of the peptide is covalently linked to the paracetylphenylalanine (pAcF) residue of the light chain or heavy chain, with the proviso that if the light chain has the amino acid sequence of SEQ ID NO:64 then heavy chain does not have the amino acid sequence of SEQ ID NO:65 and if the light chain has the amino acid sequence of SEQ ID NO:71 or 72 then the heavy chain has the amino acid sequence of SEQ ID NO:65.

7. A pharmaceutical composition comprising the antibody peptide conjugate of claim 1 and a pharmaceutically acceptable carrier.

8. A method for treating a metabolic disease or disorder in a patient, comprising administering to a patient in need the pharmaceutical composition of claim 1 to treat the metabolic disease or disorder.

9. The method of claim 8, wherein the metabolic disease or disorder comprises diabetes, non-alcoholic fatty liver disease (NAFLD), non-alcoholic steatohepatitis (NASH), or obesity.

10. The method of claim 9, wherein the diabetes comprises Type 1 diabetes, Type II diabetes, or gestational diabetes.

* * * * *